US011814631B2

(12) United States Patent
Nuccio et al.

(10) Patent No.: US 11,814,631 B2
(45) Date of Patent: Nov. 14, 2023

(54) MODIFIED EXCISABLE MON89034 TRANSGENIC MAIZE INSECT RESISTANCE LOCUS

(71) Applicant: INARI AGRICULTURE TECHNOLOGY, INC., Cambridge, MA (US)

(72) Inventors: Michael Lee Nuccio, Salem, NH (US); Michael Andreas Kock, Rheinfelden (DE); Joshua L. Price, Cambridge, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

(21) Appl. No.: 18/058,073

(22) Filed: Nov. 22, 2022

(65) Prior Publication Data
US 2023/0200336 A1 Jun. 29, 2023

Related U.S. Application Data

(63) Continuation of application No. PCT/US2021/043851, filed on Jul. 30, 2021.

(60) Provisional application No. 63/203,137, filed on Jul. 9, 2021, provisional application No. 63/202,569, filed on Jun. 16, 2021, provisional application No. 63/201,030, filed on Apr. 9, 2021, provisional application No. 63/201,029, filed on Apr. 9, 2021, provisional application No. 63/199,951, filed on Feb. 4, 2021, provisional application No. 63/199,949, filed on Feb. 4, 2021, provisional application No. 63/199,930, filed on Feb. 3, 2021, provisional application No. 63/059,916, filed on Jul. 31, 2020, provisional application No. 63/059,860, filed on Jul. 31, 2020, provisional application No. 63/059,813, filed on Jul. 31, 2020, provisional application No. 63/059,963, filed on Jul. 31, 2020.

(51) Int. Cl.
| | |
|---|---|
| *C12N 15/82* | (2006.01) |
| *C12Q 1/6895* | (2018.01) |
| *C12N 9/22* | (2006.01) |
| *C12N 15/11* | (2006.01) |
| *A01H 6/54* | (2018.01) |
| *A01H 5/10* | (2018.01) |
| *C12Q 1/6834* | (2018.01) |
| *A01H 6/46* | (2018.01) |
| *C07K 14/415* | (2006.01) |

(52) U.S. Cl.
CPC .......... *C12N 15/8201* (2013.01); *A01H 5/10* (2013.01); *A01H 6/4684* (2018.05); *A01H 6/542* (2018.05); *C07K 14/415* (2013.01); *C12N 9/22* (2013.01); *C12N 15/11* (2013.01); *C12N 15/8213* (2013.01); *C12N 15/8286* (2013.01); *C12Q 1/6834* (2013.01); *C12Q 1/6895* (2013.01); *C12N 2310/20* (2017.05); *C12N 2800/80* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,632,985 B2 | 12/2009 | Malven et al. | |
| 8,062,840 B2 * | 11/2011 | Anderson | C12N 15/8286 536/22.1 |
| 8,232,456 B2 | 7/2012 | Long et al. | |
| 8,450,561 B2 | 5/2013 | Beazley et al. | |
| 8,455,720 B2 | 6/2013 | Long et al. | |
| 8,466,346 B2 | 6/2013 | Deframond et al. | |
| 8,575,434 B2 | 11/2013 | Diehn et al. | |
| 9,428,765 B2 | 8/2016 | Anderson et al. | |
| 9,540,655 B2 | 1/2017 | Cui et al. | |
| 11,041,172 B2 | 6/2021 | Cermak | |
| 11,214,811 B1 | 1/2022 | Nuccio et al. | |
| 11,242,534 B1 | 2/2022 | Nuccio et al. | |
| 11,326,177 B2 | 5/2022 | Price et al. | |
| 11,359,210 B2 | 6/2022 | Price et al. | |
| 11,369,073 B2 | 6/2022 | Price et al. | |
| 2010/0162428 A1 | 6/2010 | Brown et al. | |
| 2011/0191899 A1 | 8/2011 | Ainley et al. | |
| 2014/0196169 A1 | 7/2014 | D'Halluin et al. | |
| 2015/0059010 A1 | 2/2015 | Cigan et al. | |
| 2015/0082478 A1 | 3/2015 | Cigan et al. | |
| 2016/0333363 A1 | 11/2016 | Srivastava | |

(Continued)

FOREIGN PATENT DOCUMENTS

| | | |
|---|---|---|
| CN | 104830860 A | 8/2015 |
| WO | 2022026375 A1 | 2/2022 |

(Continued)

OTHER PUBLICATIONS

Begemann et al., "Precise insertion and guided editing of higher plant genomes using Cpf1 CRISP nucleases," Scientific Reports, Sep. 14, 2017, vol. 7, No. 11606, pp. 1-6.

Begemann et al., Supplementary Data—Precise insertion and guided editing of higher plant genomes using Cpf1 CRISPR nucleases, Scientific Reports, Sep. 14, 2017, vol. 7, No. 11606, 18 pages.

Danilo et al., "The DFR locus: A smart landing pad for targeted transgene insertion in tomato," PLoS One, Dec. 6, 2018, vol. 13, No. 12, pp. 1-14.

(Continued)

*Primary Examiner* — Matthew R Keogh
(74) *Attorney, Agent, or Firm* — McKee, Voorhees & Sease, PLC

(57) ABSTRACT

Transgenic INIR11 maize plants comprising modifications of the MON89034 maize locus which provide for facile excision of the modified MON89034 transgenic locus or portions thereof, methods of making such plants, and use of such plants to facilitate breeding are disclosed.

Figure 1:
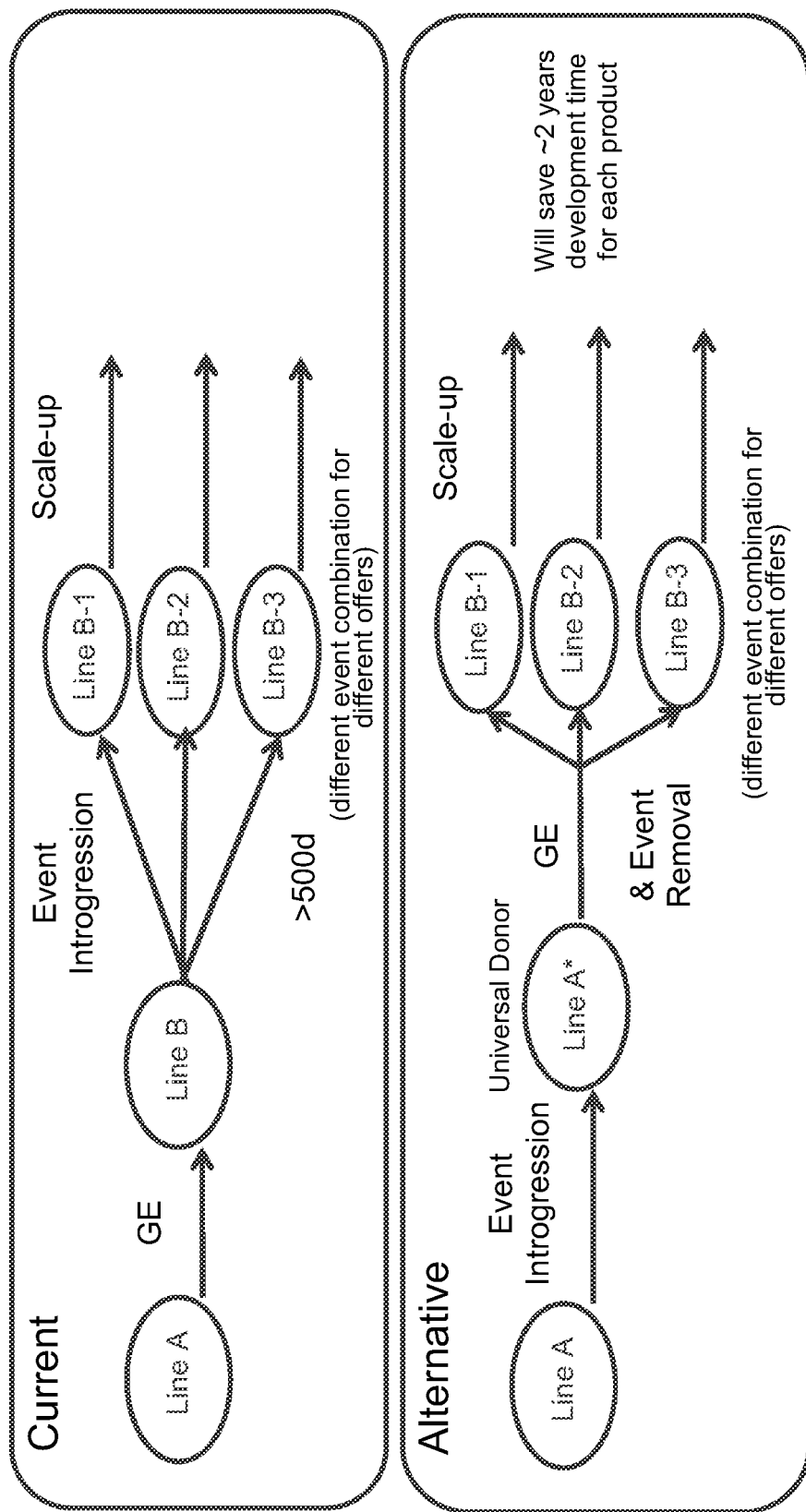

13 Claims, 4 Drawing Sheets
Specification includes a Sequence Listing.

(56) References Cited

U.S. PATENT DOCUMENTS

| | | |
|---|---|---|
| 2017/0166912 A1 | 6/2017 | Brower-Toland et al. |
| 2018/0163218 A1 | 6/2018 | Corbin et al. |
| 2019/0112614 A1 | 4/2019 | Russell et al. |
| 2019/0136249 A1 | 5/2019 | Sakai et al. |
| 2019/0320607 A1 | 10/2019 | Christensen et al. |
| 2019/0352655 A1 | 11/2019 | Niu et al. |
| 2020/0157554 A1 | 5/2020 | Cigan et al. |
| 2020/0405649 A1 | 12/2020 | Wang et al. |
| 2022/0030806 A1 | 2/2022 | Price et al. |
| 2022/0030822 A1 | 2/2022 | Nuccio et al. |
| 2022/0033833 A1 | 2/2022 | Gilbertson et al. |
| 2022/0033836 A1 | 2/2022 | Price et al. |
| 2022/0098602 A1 | 3/2022 | Nuccio et al. |
| 2022/0154194 A1 | 5/2022 | Nuccio et al. |
| 2022/0251584 A1 | 8/2022 | Nuccio et al. |
| 2022/0364105 A1 | 11/2022 | Price et al. |
| 2023/0077473 A1 | 3/2023 | Price et al. |
| 2023/0078387 A1 | 3/2023 | Kock et al. |
| 2023/0083144 A1 | 3/2023 | Nuccio et al. |
| 2023/0087222 A1 | 3/2023 | Kock et al. |
| 2023/0147013 A1 | 5/2023 | Nuccio et al. |
| 2023/0203514 A1 | 6/2023 | Price et al. |

FOREIGN PATENT DOCUMENTS

| | | |
|---|---|---|
| WO | 2022026379 A1 | 2/2022 |
| WO | 2022026390 A1 | 2/2022 |
| WO | 2022026395 A2 | 2/2022 |
| WO | 2022026403 A2 | 2/2022 |

OTHER PUBLICATIONS

Eaglesham et al., "New DNA-Editing Approaches: Methods, Applications & Policy for Agriculture," North American Agricultural Biotechnology Council, Oct. 8-9, 2014, 255 pages.

Gleditzsch et al., "PAM identification by CRISPR-Cas effector complexes: diversified mechanisms and structures," RNA Biology, Apr. 2019, vol. 16, No. 4, pp. 504-517.

International Search Report in PCT/US2021/043161, dated Jan. 5, 2022, 6 pages.

International Search Report in PCT/US2021/043170, dated Jan. 5, 2022, 6 pages.

International Search Report in PCT/US2021/043187, dated Jan. 6, 2022, 6 pages.

International Search Report in PCT/US2021/043192, dated Jan. 27, 2022, 7 pages.

International Search Report in PCT/US2021/043207, dated Jan. 27, 2022, 6 pages.

International Search Report in PCT/US2021/043851, dated Dec. 30, 2021, 6 pages.

International Search Report in PCT/US2021/043919, dated Jan. 20, 2022, 8 pages.

International Search Report in PCT/US2021/043933, dated Dec. 30, 2021, 6 pages.

International Search Report in PCT/US2021/044198, dated Jan. 19, 2022, 6 pages.

Non-Final Office Action in U.S. Appl. No. 17/302,110, dated May 24, 2023, 27 pages.

Non-Final Office Action in U.S. Appl. No. 17/650,031, dated May 26, 2023, 11 pages.

Non-Final Office Action in U.S. Appl. No. 18/057,860, dated Jun. 1, 2023, 49 pages.

Non-Final Office Action in U.S. Appl. No. 18/057,867, dated Jun. 7, 2023, 17 pages.

Non-Final Office Action in U.S. Appl. No. 18/058,081, dated Apr. 11, 2023, 19 pages.

Non-Final Office Action in U.S. Appl. No. 18/058,144, dated Jun. 7, 2023, 49 pages.

Non-Final Office Action in U.S. Appl. No. 18/058,156, dated May 19, 2023, 24 pages.

Non-Final Office Action in U.S. Appl. No. 18/058,161, dated Apr. 11, 2023, 15 pages.

Non-Final Office Action in U.S. Appl. No. 18/162,134, dated Jun. 21, 2023, 28 pages.

Shi et al., "ARGOS8 variants generated by CRISPR-Cas9 improve maize grain yield under field drought stress conditions," Plant Biotechnology Journal, Feb. 2017, vol. 15, pp. 207-216.

Yau et al., "Less is more: strategies to remove marker genes from transgenic plants," BMC Biotechnology, Apr. 2013, vol. 13, No. 36, pp. 1-23.

Zhang et al., "Off-target Effects in CRISPR/Cas9-mediated Genome Engineering," Molecular Therapy—Nucleic Acids, Nov. 17, 2015, vol. 4, pp. 1-8.

Zhong et al., "Plant Genome Editing Using FnCpf1 and LbCpf1 Nucleases at Redefined and Altered PAM Sites," Molecular Plant, Jul. 2018, vol. 11, No. 7, pp. 999-1002.

Zhong et al., "Supplementary Data—Plant Genome Editing Using FnCpf1 and LbCpf1 Nucleases at Redefined and Altered PAM Sites," Molecular Plant, Jul. 2018, vol. 11, No. 7, 36 pages.

Baliga et al., "Investigation of direct repeats, spacers and proteins associated with clustered regularly interspaced short palindromic repeat (CRISPR) system of Vibrio parahaemolyticus," Molecular Genetics and Genomics, Oct. 24, 2018, vol. 294, pp. 253-262.

Biopesticides Registration Action Document, "Bacillus thuringiensis Vip3Aa20 Insecticidal Protein and the Genetic Material Necessary for Its Production (via Elements of Vector pNOV1300) in Event MIR162 Maize (OECD Unique Identifier: SYN-IR162-4)," PC Code: 006599, U.S. Environmental Protection Agency, Office of Pesticide Programs, Biopesticides and Pollution Prevention Division, Mar. 2009, 175 pages.

Bissler, J.J., "Triplex DNA and human disease," Frontiers in Bioscience, May 1, 2007, vol. 12, pp. 4536-4546.

Bortesi et al., "The CRISPR/Cas9 system for plant genome editing and beyond," Biotechnology Advances, Dec. 20, 2014, vol. 33, Issue 1, pp. 41-52.

Charpentier et al., "Biogenesis pathways of RNA guides in archaeal and bacterial CRISPR-Cas adaptive Immunity," FEMS Microbiology Reviews, May 19, 2015, vol. 39, Issue 3, pp. 428-441.

Cho et al., "Nonallelic homologous recombination events responsible for copy number variation within an RNA silencing locus," Plant Direct, vol. 3, Aug. 27, 2019, 16 pages.

Du et al., "Construction of Marker-Free Genetically Modified Maize Using a Heat-Inducible Auto-Excision Vector," Genes, May 17, 2019, vol. 10, No. 374, 17 pages.

Du et al., "Infection of Embryonic Callus with Agrobacterium Enables High-Speed Transformation of Maize," International Journal of Molecular Sciences, Jan. 11, 2019, vol. 20, No. 279, 15 pages.

Finnigan et al., "mCAL: A New Approach for Versatile Multiplex Action of Cas9 Using One sgRNA and Loci Flanked by a Programmed Target Sequence," G3: Genes, Genomes, Genetics, Jul. 1, 2016, vol. 6, pp. 2147-2156.

Gurusaran et al., "RepEx: Repeat extractor for biological sequences," Genomics, Jul. 21, 2013, vol. 102, pp. 403-408.

International Searching Authority in connection with PCT/US21/43897 filed Jul. 30, 2021, "Invitation to Pay Additional Fees and, Where Applicable, Protest Fee," dated Oct. 27, 2021, 3 pages.

International Searching Authority in connection with PCT/US21/43935 filed Jul. 30, 2021, "Invitation to Pay Additional Fees and, Where Applicable, Protest Fee," dated Oct. 26, 2021, 3 pages.

International Searching Authority in connection with PCT/US21/43945 filed Jul. 30, 2021, "Invitation to Pay Additional Fees and, Where Applicable, Protest Fee," dated Oct. 27, 2021, 3 pages.

Kim et al., "CRISPR/Cpf1-mediated DNA-free plant genome editing," Nature Communications, Feb. 16, 2017, vol. 8, Article No. 14406, 7 pages.

Li et al., "Expanding the Scope of CRISPR/Cpf1-Mediated Genome Editing in Rice," Molecular Plant, Jul. 2, 2018, vol. 11, No. 7, pp. 995-998, 14 pages.

Luo et al., "Improperly Terminated, Unpolyadenylated mRNA of Sense Transgenes is Targeted by RDR6-Mediated RNA Silencing in Arabidopsis," The Plant Cell, Mar. 23, 2007, vol. 19, pp. 943-958.

(56) References Cited

OTHER PUBLICATIONS

Malzahn et al., "Application of CRISPR-Cas12a temperature sensitivity for improved genome editing in rice, maize, and *Arabidopsis*," BMC Biology, Jan. 31, 2019, vol. 17, No. 9, 14 pages.
Non-Final Office Action in U.S. Appl. No. 17/248,936, dated Mar. 25, 2021, 25 pages.
Non-Final Office Action in U.S. Appl. No. 17/249,640, dated Jun. 29, 2021, 10 pages.
Non-Final Office Action in U.S. Appl. No. 17/302,110, dated Jun. 29, 2021, 22 pages.
Non-Final Office Action in U.S. Appl. No. 17/302,121, dated Jul. 8, 2021, 10 pages.
Non-Final Office Action in U.S. Appl. No. 17/302,739, dated Aug. 3, 2021, 24 pages.
Notice of Allowance in U.S. Appl. No. 17/249,640, dated Sep. 22, 2021, 7 pages.
Que et al., "Maize transformation technology development for commercial event generation," Frontiers in Plant Science, Aug. 5, 2014, vol. 5, Article No. 379, 19 pages.
Srivastava et al., "Gene Stacking by recombinases," Plant Biotechnology Journal, Feb. 2016, vol. 14, pp. 471-482.
Srivastava, et al., "Dual-targeting by CRISPR/Cas9 for precise excision of transgenes from rice genome," Plant Cell Tissue and Organ Culture, Jan. 20, 2017, vol. 129, pp. 153-160.
Ward et al., "Petition for Determination of Nonregulated Status for Insect-Resistant MIR162 Maize," Syngenta Biotechnology, Inc., Aug. 31, 2007, 271 pages.
"What is a CRISPR-Cas system?," CRISPR-CAS++, Universite Paris-Saclay, accessed Nov. 2, 2021. Retrieved from the Internet <URL:https://crisprcas.i2bc.paris-saclay.fr/Home/About>, 2 pages.
Xing et al., "Revealing frequent alternative polyadenylation and widespread low-level transcription read-through of hovel plant transcription terminators," Plant Biotechnology Journal, Sep. 2010, vol. 8, pp. 772-782.
Young et al., "CRISPR-Cas9 Editing in Maize: Systematic Evaluation of Off-target Activity and Its Relevance in Crop Improvement," Scientific Reports, Apr. 30, 2019, vol. 9, No. 6729, 11 pages.

\* cited by examiner

MODIFIED EXCISABLE MON89034 TRANSGENIC MAIZE INSECT RESISTANCE LOCUS

CROSS-REFERENCE TO RELATED APPLICATIONS

This is a continuation application of International Application No. PCT/US2021/043,851, filed on Jul. 30, 2021, which claims the benefit of priority to U.S. Provisional Patent Application No. 63/203,137, filed on Jul. 9, 2021, U.S. Provisional Patent Application No. 63/202,569, filed on Jun. 16, 2021, U.S. Provisional Patent Application Nos. 63/201,030 and 63/201,029, filed on Apr. 9, 2021, U.S. Provisional Patent Application Nos. 63/199,951 and 63/199,949, filed on Feb. 4, 2021, U.S. Provisional Patent Application No. 63/199,930, filed on Feb. 3, 2021, and U.S. Provisional Patent Application Nos. 63/059,813, 63/059,860, 63/059,916, and 63/059,963, filed on Jul. 31, 2020, each of which are incorporated herein by reference in their entireties.

REFERENCE TO SEQUENCE LISTING SUBMITTED ELECTRONICALLY

The instant application contains a Sequence Listing which has been submitted electronically in XML formatted and is herein incorporated by reference in its entirety. Said XML copy, created on Nov. 21, 2022, is named "P13646US00_SequenceListing.xml" and is 173,445 bytes in size.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An example of a selected transgenic corn event which confers lepidopteran insect pest tolerance is the MON89034 transgenic maize event disclosed in U.S. Pat. No. 9,428,765. MON89034 transgenic maize plants express Cry2Ab2 as well as cry1A.105 proteins which can confer resistance to) lepidopteran insect infestations (e.g., Fall armyworm (*Spodoptera frugiperda*), European corn borer (*Ostrinia nubilalis*), corn earworm (*Helicoverpa zea*), and southwestern corn borer (*Diatraea Grandiosella*).

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015,1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic maize plant cells comprising an INIR11 transgenic locus comprising an originator guide RNA recognition site (OgRRS) in a first DNA junction polynucleotide of a MON89034 transgenic locus and a cognate guide RNA recognition site (CgRRS) in a second DNA junction polynucleotide of the MON89034 transgenic locus are provided. Transgenic maize plant cells comprising an INIR11 transgenic locus comprising an insertion and/or substitution in a DNA junction polynucleotide of a MON89034 transgenic locus of DNA comprising a cognate guide RNA recognition site (CgRRS) are provided. In certain embodiments, the MON89034 transgenic locus is set forth in SEQ ID NO:1, is present in seed deposited at the ATCC under accession No. PTA-7455 is present in progeny thereof, is present in allelic variants thereof, or is present in other variants thereof. INIR11 transgenic maize plant cells, transgenic maize plant seeds, and transgenic maize plants all comprising a transgenic locus set forth in SEQ ID NO: 2, 3, 17, 23, 26, 27, 28, 29, 30, 31, or an allelic variant thereof are provided. Transgenic maize plant parts including seeds and transgenic maize plants comprising the maize plant cells are also provided.

Methods for obtaining a bulked population of inbred seed comprising selfing the aforementioned transgenic maize plants and harvesting seed comprising the INIR11 transgenic locus from the selfed maize plant are also provided.

Methods of obtaining hybrid maize seed comprising crossing the aforementioned transgenic maize plants to a second maize plant which is genetically distinct from the first maize plant and harvesting seed comprising the INIR11 transgenic locus from the cross are provided. Methods for obtaining a bulked population of seed comprising selfing a transgenic maize plant comprising the transgenic locus set forth in SEQ ID NO: 2, 3, 17, 23, 26, 27, 28, 29, 30, 31, or an allelic variant thereof and harvesting transgenic seed comprising the transgenic locus set forth in SEQ ID NO: 2, 3, 17, 23, 26, 27, 28, 29, 30, 31, or an allelic variant thereof are provided.

A DNA molecule comprising SEQ ID NO: 2, 3, 8, 9, 10, 11, 16, 17, 23, 24, 25, 26, 27, 28, 29, 30, 31 or an allelic variant thereof is provided. Processed transgenic maize plant products and biological samples comprising the DNA molecules are provided. Nucleic acid molecules adapted for detection of genomic DNA comprising the DNA molecules, wherein said nucleic acid molecule optionally comprises a detectable label are provided. Methods of detecting a maize plant cell comprising the INIR11 transgenic locus of any one of claims 1 to 3, comprising the step of detecting a DNA molecule comprising SEQ ID NO: 2, 3, 8, 9, 10, 11, 16, 17, 23, 24, 25, 26, 27, 28, 29, 30, 31 or an allelic variant thereof are provided.

Methods of excising the INIR11 transgenic locus from the genome of the aforementioned maize plant cells comprising the steps of: (a) contacting the edited transgenic plant genome of the plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR11 transgenic locus flanked by the OgRRS and the CgRRS has been excised.

BRIEF DESCRIPTION OF THE DRAWINGS/FIGURES

FIG. 1 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 1, "GE" refers to genome editing (e.g., including introduction of targeted genetic changes with genome editing molecules and "Event Removal" refers to excision of a transgenic locus (i.e., an "Event") with genome editing molecules.

Figure 2A:
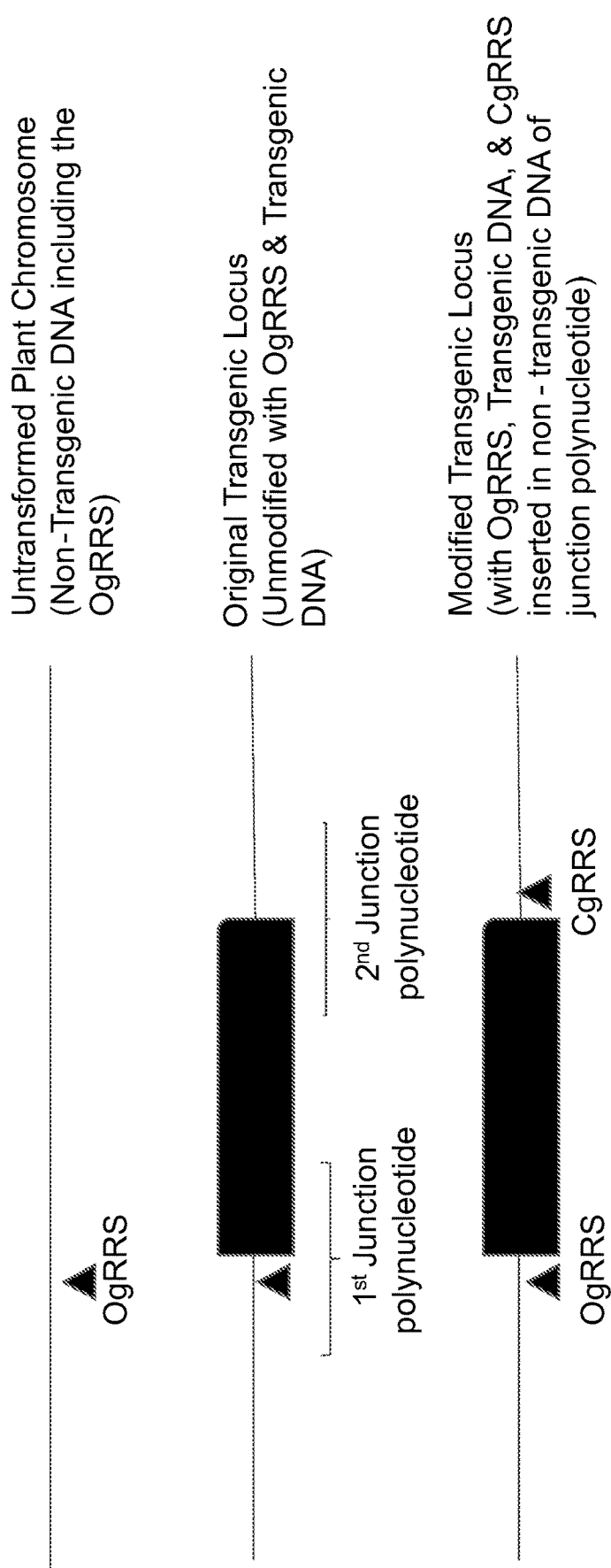
Figure 2B:
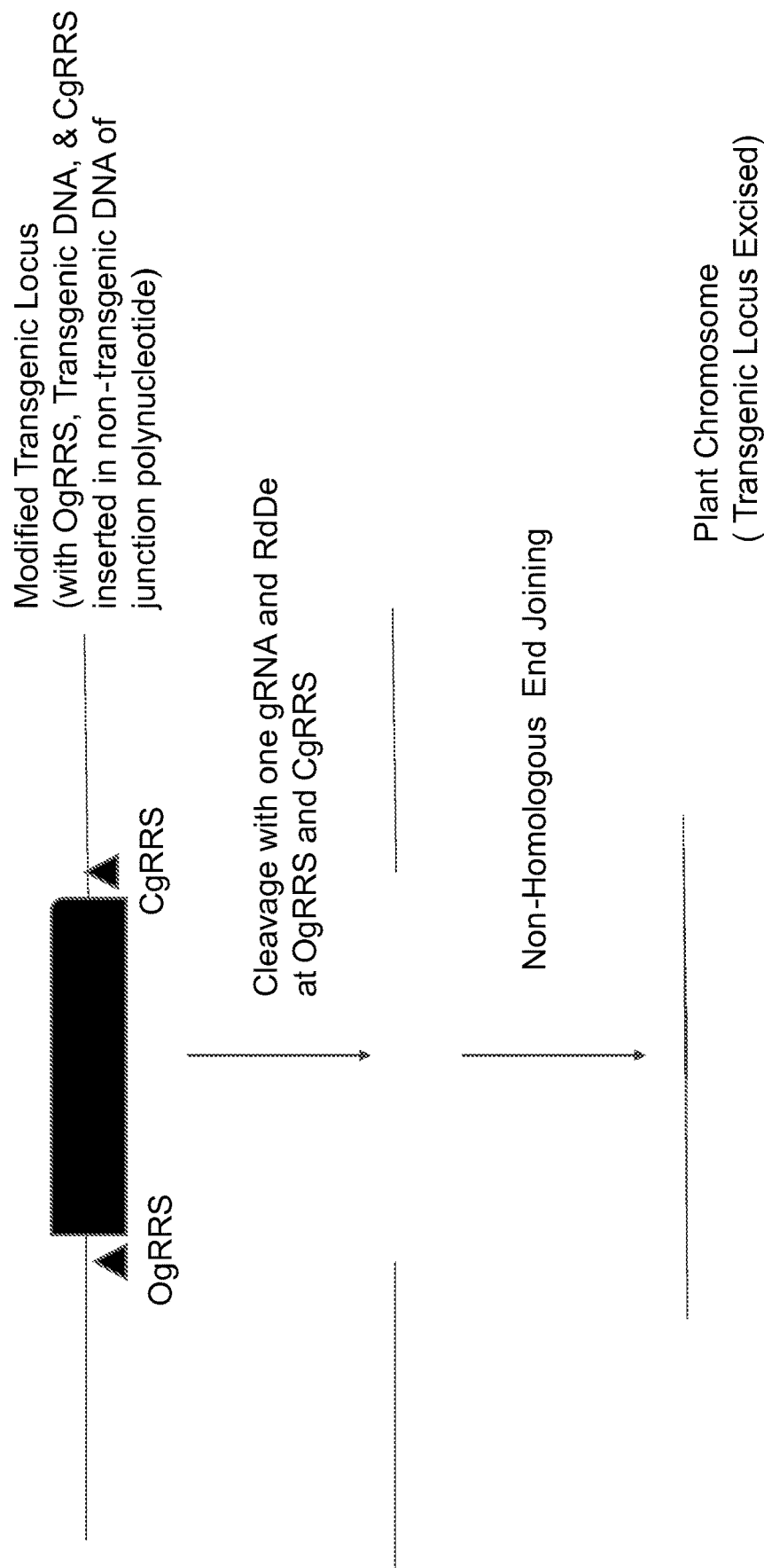
Figure 2C:
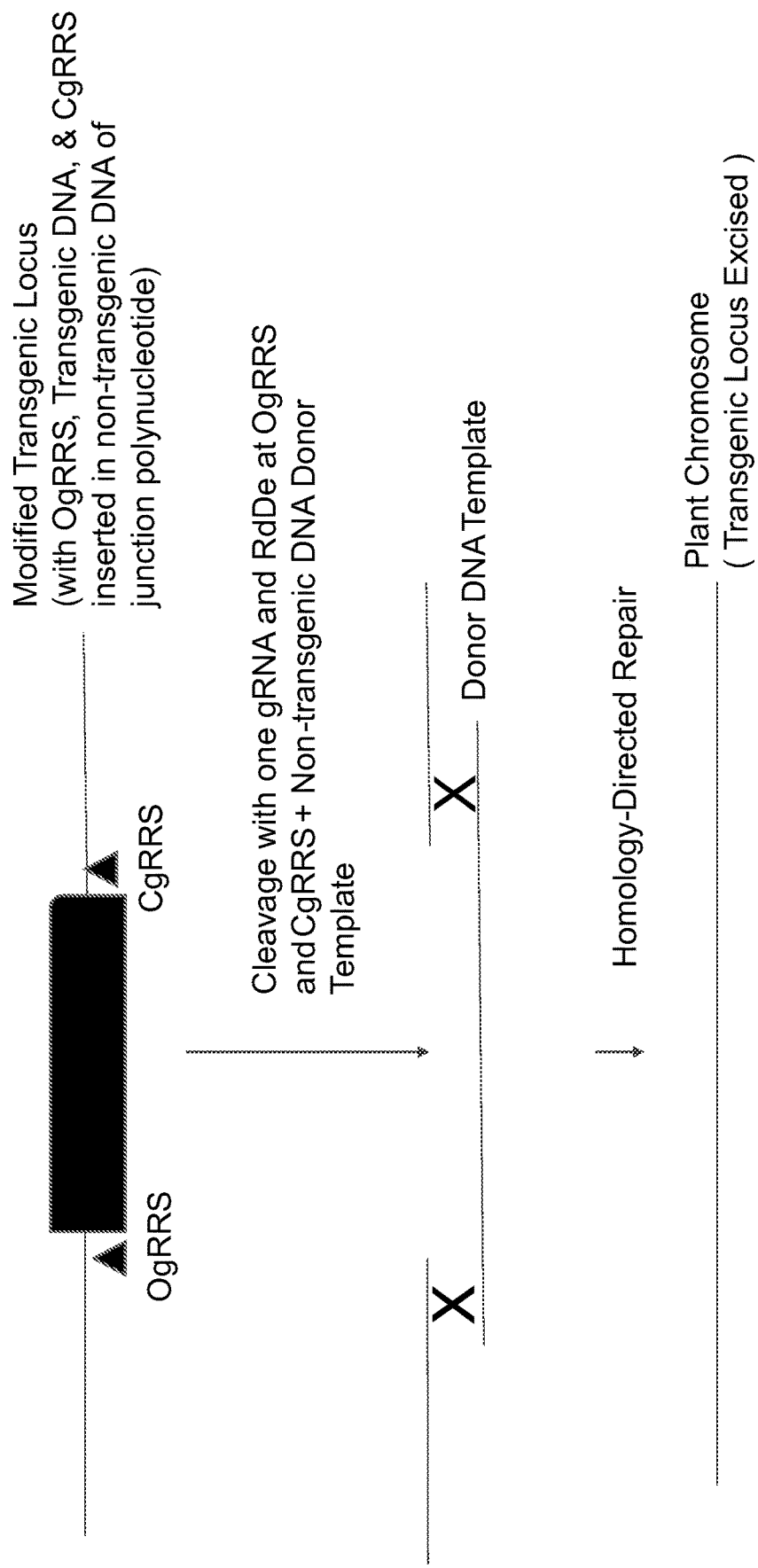

FIG. 2A, B, C. FIG. 2A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the $1^{st}$ junction polynucleotide (middle); and (iii) the modified transgenic locus with a cognate guide RNA inserted into the non-transgenic DNA of the $2^{nd}$ junction polynucleotide (bottom). FIG. 2B shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 2C shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template. In FIG. 2C, cleavage of the modified transgenic locus in the presence of the donor DNA template which has homology to non-transgenic DNA but lacks the OgRRS in the $1^{st}$ and $2^{nd}$ junction polynucleotides followed by homology-directed repair processes to provide a plant chromosome where the transgenic locus is excised and non-transgenic DNA present in the untransformed plant chromosome is at least partially restored.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). A Cas12a protein provided herein includes the protein of SEQ ID NO: 21.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the term "MON89034" is used to refer to any of a transgenic maize locus, transgenic maize plants and parts thereof including seed set forth in U.S. Pat. No. 9,428,765, which is incorporated herein by reference in its entirety. Representative MON89034 transgenic maize seed have been deposited with American Type Culture Collection (ATCC, Manassas, Va. 20110-2209 USA) under Accession No. PTA-7455. MON89034 transgenic loci include loci having the sequence of SEQ ID NO:1, the sequence of the MON89034 locus in the deposited seed of Accession No. PTA-7455 and any progeny thereof, as well as allelic variants and other variants of SEQ ID NO:1

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g., inbred or doubled haploid. Elite crop plants can include inbred lines used as is or used as pollen donors or pollen recipients in hybrid seed production (e.g., used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' DNA junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g., DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INIR11" is used to refer either individually collectively to items that include any or all of the MON89034 transgenic maize loci which have been modified as disclosed herein, modified MON89034 transgenic maize plants and parts thereof including seed, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS are operably linked to junction polynucleotides when they can be recognized by a gRNA and an RdDe to provide for excision of the transgenic locus or portion thereof flanked by the junction polynucleotides.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site. In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site, where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Various sequences set forth in the sequence listing are described in the following table.

TABLE 1

Description of sequences.

| SEQ ID NO | Description |
|---|---|
| 1 | MON89034 Complete Transgenic Locus comprising 5' flanking plant genomic DNA, 5' junction, cry1A.105 expression cassette, cry2Ab2 expression cassette, 3' junction, and 3' flanking plant genomic DNA. The 5' flanking plant genomic DNA comprises nucleotides 1-2061 of SEQ ID NO: 1, the transgenic insert spans nucleotides 2062-11378 of SEQ ID NO: 1, and the 3' flanking plant genomic DNA comprises nucleotides 11379-12282 of SEQ ID NO: 1. |
| 2 | INIR11-1 (with gRNA-1 Cut resulting in a deletion of nucleotides in a MON89034 5' junction polynucleotide sequence) |
| 3 | INIR11-2 (Insertion of 27 bp CgRRS with gRNA-2 and gRNA-3 cuts with SEQ ID NO: 25 donor DNA template) |
| 4 | gRNA-1 coding |
| 5 | gRNA-2 coding |
| 6 | gRNA-3 coding |
| 7 | OgRRS |
| 8 | CgRRS + Flanking DNA (G1 Insert) |
| 9 | CgRRS + Flanking DNA (G1 and G3 Insert) |
| 10 | CgRRS + Flanking DNA (G2 and G3 Insert) |
| 11 | MON89034 CgRRS DNA donor template sequence containing the SEQ ID NO: 8 CgRRS |
| 12 | MON89034 5' target insertion site |
| 13 | MON89034 -gRNA spacer coding sequence that targets CgRRS of SEQ ID NO: 8, 9, 10 and OgRRS of SEQ ID NO: 7 |
| 14 | MON89034 5' primer |
| 15 | MON89034 3' primer |
| 16 | MON89034 CgRRS and flank PCR amplicon from SEQ ID NO: 17 template using SEQ ID NO: 14 and 15 primers |
| 17 | INIR11-3 (Insertion of 27 bp CgRRS with gRNA-1 cut and SEQ ID NO: 11 donor DNA template) |
| 18 | (Cas12a Nuclease) (>sp|U2UMQ6|CS12A_ACISB CRISPR-associated endonuclease Cas12a OS = Acidaminococcus sp. (strain BV3L6) OX = 1111120 GN = cas12a PE = 1 SV = 1) |
| 19 | MON89034 transgenic locus 5' Junction Polynucleotide |
| 20 | MON89034 transgenic locus 5' plant genomic flanking |
| 21 | MON89034 transgenic locus 3' Junction Polynucleotide |
| 22 | MON89034 transgenic locus 3' plant genomic flanking |
| 23 | INIR11-4 (Insertion of 27 bp CgRRS with gRNA-1 and gRNA-3 cuts with SEQ ID NO: 24 donor DNA template) |

TABLE 1-continued

Description of sequences.

| SEQ ID NO | Description |
|---|---|
| 24 | MON89034 CgRRS DNA donor template for generating INIR11-4 containing the SEQ ID NO: 9 CgRRS |
| 25 | MON89034 CgRRS DNA donor template for generating INIR11-2 containing the SEQ ID NO: 10 CgRRS |
| 26 | INIR11-5 (gRNA-1 and gRNA-3 cuts resulting in a deletion of nucleotides in a MON89034 5' junction polynucleotide sequence) |
| 27 | INIR11-6 (gRNA-2 and gRNA-3 cuts resulting in a deletion of nucleotides in a MON89034 5' junction polynucleotide sequence) |
| 28 | INIR11-7 (gRNA-1 cut resulting in a deletion of nucleotides in a MON89034 5' junction polynucleotide sequence) |
| 29 | INIR11-8 (gRNA-1 cut resulting in a deletion of nucleotides in a MON89034 5' junction polynucleotide sequence) |
| 30 | INIR11-9 (gRNA-1 cut resulting in a deletion of nucleotides in a MON89034 5' junction polynucleotide sequence) |
| 31 | INIR11-10 (gRNA-1 cut resulting in a deletion of nucleotides in a MON89034 5' junction polynucleotide sequence) |

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as maize and soybean include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel). Provided herein are methods whereby targeted genetic changes are efficiently combined with desired subsets of transgenic loci in elite progeny plant lines (e.g., elite inbreds used for hybrid seed production or for inbred varietal production). Also provided are plant genomes containing modified transgenic loci which can be selectively excised with a single gRNA molecule. Such modified transgenic loci comprise an originator guide RNA recognition site (OgRRS) which is identified in non-transgenic DNA of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus with a single guide RNA. An originator guide RNA recognition site (OgRRS) comprises endogenous DNA found in untransformed plants and in endogenous non-transgenic DNA of junction polynucleotides of transgenic plants containing a modified or unmodified transgenic locus. The OgRRS located in non-transgenic DNA of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from endogenous non-transgenic DNA found in junction sequences of transgenic plants containing an unmodified transgenic locus. Also provided are unique transgenic locus excision sites created by excision of such modified transgenic loci, DNA molecules comprising the modified transgenic loci, unique transgenic locus excision sites and/or plants comprising the same, biological samples containing the DNA, nucleic acid markers adapted for detecting the DNA molecules, and related methods of identifying the elite crop plants comprising unique transgenic locus excision sites.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 1. In certain embodiments, INIR11 transgenic loci provided here are characterized by polynucleotide sequences that can facilitate as necessary the removal of the INIR11 transgenic loci from the genome. Useful applications of such INIR11 transgenic loci and related methods of making include targeted excision of a INIR11 transgenic locus or portion thereof in certain breeding lines to facilitate recovery of germplasm with subsets of transgenic traits tailored for specific geographic locations and/or grower preferences. Other useful applications of such INIR11 transgenic loci and related methods of making include removal of transgenic traits from certain breeding lines when it is desirable to replace the trait in the breeding line without disrupting other transgenic loci and/or non-transgenic loci. In certain embodiments, maize genomes containing INIR11 transgenic loci or portions thereof which can be selectively excised with one or more gRNA molecules and RdDe (RNA dependent DNA endonucleases) which form gRNA/target DNA complexes. Such selectively excisable INIR11 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 2A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. Examples of OgRRS polynucleotide sequences in or near a 3' junction polynucleotide in an MON89034 transgenic locus include SEQ ID NO: 7. OgRRS polynucleotide sequences located in a first junction polynucleotide can be introduced into the second junction polynucleotide using donor DNA templates as illustrated in FIG. 2A and as elsewhere described herein. A donor DNA template for introducing the SEQ ID NO: 7 OgRRS into the 5' junction polynucleotide of an MON89034 locus includes the donor DNA template of SEQ ID NO: 11 which comprises the SEQ ID NO: 8 CgRRS. Similar donor DNA templates comprising the SEQ ID NO: 9 or SEQ ID NO: 10 CgRRS elements and similar homology arms that target the MON89034 5' junction polynucleotide target sequence (e.g. SEQ ID NO: 12) can be used to obtain INIR11 transgenic loci comprising the SEQ ID NO: 9 or SEQ ID NO: 10 CgRRS elements. Double stranded breaks in a 5' junction polynucleotide of SEQ ID NO: 1 can be introduced with gRNAs encoded by SEQ ID NO: 4, 5, and/or 6 and a Cas12a nuclease. Integration of the SEQ ID NO: 11 or other donor DNA template comprising the CgRRS sequence set forth in SEQ ID NO: 9 or 10 into the 5' junction polynucleotide of an MON89034 locus at the double stranded breaks introduced by the gRNAs encoded by SEQ ID NO: 4, 5, and/or 6 and a Cas12a nuclease can provide an INIR11 locus comprising the CgRRS sequence set forth in SEQ ID NO: 8, 9, or 10. Double stranded breaks in a 5' junction polynucleotide of SEQ ID NO: 1 can be introduced with gRNAs encoded by SEQ ID NO: 4, 5, and/or 6. Another donor DNA template adapted for insertion of the OgRRS of SEQ ID NO: 7 in a 5' junction polynucleotide of a MON89034 transgenic locus can comprise SEQ ID NO: 24 or 25. Double stranded breaks in a 5' junction polynucleotide of SEQ ID NO: 1 can be introduced with gRNAs encoded by SEQ ID NO: 4 and a Cas12a nuclease. A donor DNA template of SEQ ID NO: 11 or the equivalent thereof having longer or shorter homology arms can be used to obtain the CgRRS insertion in the 5' junction polynucleotide that is set forth in SEQ ID NO: 16. An INIR11-3 transgenic locus containing this CgRRS insertion is set forth in SEQ ID NO: 17. An INIR11-4 transgenic locus containing the CgRRS insertion of SEQ ID NO: 9 is set forth in SEQ ID NO: 23. The INIR11-4 transgenic locus of SEQ ID NO: 23 can be obtained by using gRNA-1 (SEQ ID NO: 4) and gRNA-3 (SEQ ID NO: 6) with a Cas12A nuclease and the donor DNA template of SEQ ID NO: 24. An INIR11-2 transgenic locus containing the CgRRS insertion of SEQ ID NO: 10 is set forth in SEQ ID NO: 26. The INIR11-2 transgenic locus of SEQ ID NO: 26 can be obtained by using gRNA-2 (SEQ ID NO: 5) and gRNA-3 (SEQ ID NO: 6) with a Cas12A nuclease and the donor DNA template of SEQ ID NO: 25.

Also provided are unique transgenic locus excision sites created by excision of INIR11 transgenic loci or selectively excisable INIR11 transgenic loci, DNA molecules comprising the INIR11 transgenic loci or unique fragments thereof (i.e., fragments of an INIR11 locus which are not found in an MON89034 transgenic locus), INIR11 plants comprising the same, biological samples containing the DNA, nucleic acid markers adapted for detecting the DNA molecules, and related methods of identifying maizew plants comprising unique INIR11 transgenic locus excision sites and unique fragments of a INIR11 transgenic locus. DNA molecules comprising unique fragments of an INIR11 transgenic locus are diagnostic for the presence of an INIR11 transgenic locus or fragments thereof in a maize plant, maize cell, maize seed, products obtained therefrom (e.g., seed meal or stover), and biological samples. DNA molecules comprising unique fragments of an INIR11 transgenic locus include DNA molecules comprising Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the maize MON89034 transgenic locus. The maize MON89034 transgenic locus and its transgenic junction sequences are also set forth in table 1. Maize plants comprising the MON89034 transgenic locus and seed thereof have been cultivated, been placed in commerce, and have been described in a variety of publications by various governmental bodies. Databases which have compiled descriptions of the MON89034 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of the MON89034 transgenic locus which can be improved by the methods provided herein are set forth or otherwise provided in SEQ ID NO: 1, U.S. Pat. No. 9,428,765, the sequence of the MON89034 locus in the deposited seed of ATCC accession No. PTA-7455, and elsewhere in this disclosure. In certain embodiments provided herein, the MON89034 transgenic locus set forth in SEQ ID NO: 1 or present in the deposited seed of ATCC accession No. PTA-7455 is referred to as an "original MON89034 transgenic locus." Allelic or other variants of the sequence set forth SEQ ID NO: 1, the patent references set forth therein and incorporated herein by reference in their entireties, and elsewhere in this disclosure which may be present in certain variant MON89034 transgenic plant loci (e.g., progeny of deposited seed of accession No. PTA-7455 which contain allelic variants of SEQ ID NO:1 or progeny originating from transgenic plant cells comprising the original MON89034 transgenic locus set forth in U.S. Pat. No. 9,428,765) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, or 12,282 nucleotides of SEQ ID NO: 1. Also provided are plants, plant parts including seeds, genomic DNA, and/or DNA obtained from INIR11 plants which comprise one or more modifications (e.g., via insertion of a CgRRS in a junction polynucleotide sequence) which provide for selective excision of the INIR11 transgenic locus or a portion thereof. Also provided herein are methods of detecting plants, genomic DNA, and/or DNA obtained from plants comprising a INIR11 transgenic locus which contains one or more of a CgRRS, deletions of selectable marker genes, deletions of non-essential DNA, and/or a transgenic locus excision site. A first junction polynucleotide of a MON89034 transgenic locus can comprise either one of the junction polynucleotides found at the 5' end or the 3' end of any one of the sequences set forth in SEQ ID NO: 1, allelic variants thereof, or other variants thereof. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INIR11 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the MON89034 transgenic locus of SEQ ID NO: 1, allelic variants thereof, or other variants thereof to obtain an INIR11 transgenic locus. In other embodiments, the OgRRS is found in non-transgenic DNA or transgenic DNA of the 3' junction polynucleotide of the MON89034 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INIR11 transgenic locus.

Also provided herein are allelic variants of any of the INIR11 transgenic loci and DNA molecules provided herein. In certain embodiments, such allelic variants of INIR11 transgenic loci include sequences having at least 85%, 90%, 95%, 98%, or 99% sequence identity across the entire length or at least 20, 40, 100, 500, 1,000, 2,000, 4,000, or nucleotides of SEQ ID NO: 2, 3, 17, 23, 26, 27, 28, 29, 30, and 31. In certain embodiments, such allelic variants of INIR11 DNA molecules include sequences having at least 85%, 90%, 95%, 98%, or 99% sequence identity across the entire length of 2, 3, 17, 23, 26, 27, 28, 29, 30, and 31.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INIR11 transgenic locus, in transgenic DNA of a DNA junction polynucleotide of an INIR11 transgenic locus, or can span the junction of the transgenic and non-transgenic DNA of a DNA junction polynucleotide of an INIR11 transgenic locus. An OgRRS can likewise be located in non-transgenic plant genomic DNA of a DNA junction polynucleotide of an INIR11 transgenic locus, in transgenic DNA of a DNA junction polynucleotide of an INIR11 transgenic locus, or can span the junction of the transgenic and non-transgenic DNA of a DNA junction polynucleotide of an INIR11 transgenic locus Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INIR11 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 1 (bottom "Alternative" panel), where two or more of the transgenic loci ("Event" in FIG. 1) are provided in Line A and then moved into elite crop plant germplasm by introgression. In the non-limiting FIG. 1 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g., Line A+ in FIG. 1) comprising two or more of the modified transgenic loci. This elite germplasm containing the modified transgenic loci (e.g., "Universal Donor" of FIG. 1) can then be subjected to genome editing molecules which can excise at least one of the transgenic loci ("Event Removal" in FIG. 1) and introduce other targeted genetic changes ("GE" in FIG. 1) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 1). In certain embodiments, it is also desirable to bulk up populations of inbred elite crop plants or their seed comprising the subset of transgenic loci and a transgenic locus excision site by selfing. In certain embodiments, inbred progeny of the selfed maize plants comprising the INIR11 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. Techniques for effecting genome editing in crop plants (e.g., maize) include use of morphogenic factors such as Wuschel (WUS), Ovule Development Protein (ODP), and/or Babyboom (BBM) which can improve the efficiency of recovering plants with desired genome edits. In some aspects, the morphogenic factor comprises WUS1, WUS2, WUS3, WOX2A, WOX4, WOX5, WOX9, BBM2, BMN2, BMN3, and/or ODP2. In certain embodiments, compositions and methods for using WUS, BBM, and/or ODP, as well as other techniques which can be adapted for effecting genome edits in elite crop plant and other germplasm, are set forth in US 20030082813, US 20080134353, US 20090328252, US 20100100981, US 20110165679, US 20140157453, US 20140173775, and US 20170240911, which are each incorporated by reference in their entireties. In certain embodiments, the genome edits can be effected in regenerable plant parts (e.g., plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INIR11 transgenic locus comprising an OgRRS in non-transgenic DNA of a 1st junction polynucleotide sequence and a CgRRS in a 2nd junction polynucleotide sequence is deleted with a gRNA and RdDe that recognize the OgRRS and the CgRRS to produce an INIR11 transgenic locus excision site. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INIR11 transgenic loci excision sites are provided herein.

In other embodiments, a segment comprising a INIR11 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS and replaced with DNA comprising the endogenous non-transgenic plant genomic DNA present in the genome prior to transgene insertion. A non-limiting example of such replacements can be visualized in FIG. 2C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of trans-gene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene.

In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a MON89034 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INIR11 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the maize plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS are created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS. A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides and repaired by NHEJ is depicted in FIG. 2B. In the depicted example set forth in FIG. 2B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are partially or essentially restored.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a $1^{st}$ junction polynucleotide and a $2^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 6,040,497, 8,759,618, 7,157,281, 6,852,915, 7,705,216, 10,316,330, 8,618,358, 8,450,561, 8,212,113, 9,428,765, 7,897,748, 8,273,959, 8,093,453, 8,901,378, 9,994,863, 7,928,296, and 8,466,346, each of which are incorporated herein by reference in their entireties.

In certain embodiments, INIR11 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 1, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by example, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/ home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target maize genes that can be subjected to targeted gene edits to confer useful traits include: (a) ZmIPK1 (herbicide tolerant and phytate reduced maize; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMS5 (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including maize which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to US Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to US Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) Science, 339:819-823; Ran et al. (2013) Nature Protocols, 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) Cell, 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) Science, 339:819-823; Xing et al. (2014) BMC Plant Biol., 14:327-340. Chemically modified sgRNAs have been demonstrated to be effective in genome editing; see, for example, Hendel et al. (2015) Nature Biotechnol., 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) Nature, 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., Sci Adv. 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) Nature 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) Nature Rev. Genet., 11:636-646; Mohanta et al. (2017)

Genes vol. 8,12: 399; Ramirez et al. Nucleic Acids Res. (2012); 40(12): 5560-5568; Liu et al. (2013) *Nature Communications,* 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as Fok1. This endonuclease must dimerize to cleave DNA. Thus, cleavage by Fok1 as part of a ZFN requires two adjacent and independent binding events, which must occur in both the correct orientation and with appropriate spacing to permit dimer formation. The requirement for two DNA binding events enables more specific targeting of long and potentially unique recognition sites. Fok1 variants with enhanced activities have been described and can be adapted for use in the methods described herein; see, e.g., Guo et al. (2010) *J. Mol. Biol.,* 400:96-107.

Transcription activator like effectors (TALEs) are proteins secreted by certain Xanthomonas species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as Fok1, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) *Genes vol.* 8,12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e. g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor polynucleotide and include the donor DNA template set forth in SEQ ID NO: 11 and equivalents thereof with longer or shorter homology arms. In certain embodiments, a donor DNA template can comprise an adapter molecule with cohesive ends which can anneal to an overhanging cleavage site (e.g., introduced by a Cas12a nuclease and suitable gRNAs). In certain embodiments, integration of the donor DNA templates can be facilitated by use of a bacteriophage lambda exonuclease, a bacteriophage lambda beta SSAP protein, and an E. coli SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor polynucleotide.

Various treatments are useful in delivery of gene editing molecules and/or other molecules to a MON89034 or INIR11 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature,* 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g., herbicide tolerance, insect resistance, and/or male sterility) are introduced into a MON89034 or INIR11 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD(P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from maize, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA, and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the MON89034 or INIR11 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www [dot]openwetware[dot]org/images/d/d3/Haploid_Arabidopsis_protocol[dot]pdf; (Ravi et al. (2014) *Nature Communications*, 5:5334, doi: 10.1038/ncomms6334). Haploids can also be obtained in a wide variety of monocot plants (e.g., maize, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the MON89034 or INIR11 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the MON89034 or INIR11 plant cells in used in the methods provided herein can include dividing cells. Dividing cells can include those cells found in various plant tissues including leaves, meristems, and embryos. These tissues include dividing cells from young maize leaf, meristems and scutellar tissue from about 8 or 10 to about 12 or 14 days after pollination (DAP) embryos. The isolation of maize embryos has been described in several publications (Brettschneider, Becker, and Lorz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INIR11 plant from a INIR11 plant cell that had been subjected to the gene editing or from a regenerable plant structure obtained from that INIR11 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INIR11 plant or its seeds, including: (a) maize seed meal (defatted or non-defatted); (b) extracted proteins, oils, sugars, and starches; (c) fermentation products; (d) animal feed or human food products (e.g., feed and food comprising maize seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

Embodiments

Various embodiments of the plants, genomes, methods, biological samples, and other compositions described herein are set forth in the following sets of numbered embodiments.

1a. A transgenic maize plant cell comprising an INIR11 transgenic locus comprising an originator guide RNA recognition site (OgRRS) in a first DNA junction polynucleotide of a MON89034 transgenic locus and a cognate guide RNA recognition site (CgRRS) in a second DNA junction polynucleotide of the MON89034 transgenic locus.

1b. A transgenic maize plant cell comprising an INIR11 transgenic locus comprising an insertion and/or substitution of DNA in a DNA junction polynucleotide of a MON89034 transgenic locus with DNA comprising a cognate guide RNA recognition site (CgRRS).

2. The transgenic maize plant cell of embodiment 1a or 1b, wherein said CgRRS comprises the DNA molecule set forth in SEQ ID NO: 8, 9, or 10; and/or wherein said MON89034 transgenic locus is set forth in SEQ ID NO:1, is present in seed deposited at the ATCC under accession No.

PTA-7455 is present in progeny thereof, is present in allelic variants thereof, or is present in other variants thereof.

3. The transgenic maize plant cell of embodiments 1a, 1b, or 2, wherein said INIR11 transgenic locus comprises the DNA molecule set forth in SEQ ID NO: 2, 3, 17, 23, 26, 27, 28, 29, 30, or 31.

4. A transgenic maize plant part comprising the maize plant cell of any one of embodiments 1a, 1b, 2, or 3, wherein said maize plant part is optionally a seed.

5. A transgenic maize plant comprising the maize plant cell of any one of embodiments 1a, 1b, 2, or 3.

6. A method for obtaining a bulked population of inbred seed comprising selfing the transgenic maize plant of embodiment 5 and harvesting seed comprising the INIR11 transgenic locus from the selfed maize plant.

7. A method of obtaining hybrid maize seed comprising crossing the transgenic maize plant of embodiment 5 to a second maize plant which is genetically distinct from the first maize plant and harvesting seed comprising the INIR11 transgenic locus from the cross.

8. A DNA molecule comprising SEQ ID NO: 2, 3, 8, 9, 10, 11, 16, 17, 23, 24, 25, 26, 27, 28, 29, 30, or 31.

9. A processed transgenic maize plant product comprising the DNA molecule of embodiment 8.

10. A biological sample containing the DNA molecule of embodiment 8.

11. A nucleic acid molecule adapted for detection of genomic DNA comprising the DNA molecule of embodiment 8, wherein said nucleic acid molecule optionally comprises a detectable label.

12. A method of detecting a maize plant cell comprising the INIR11 transgenic locus of any one of embodiments 1a, 1b, 2, or 3, comprising the step of detecting DNA molecule comprising SEQ ID NO: 2, 3, 8, 9, 10, 11, 16, 17, 23, 24, 25, 26, 27, 28, 29, 30 or 31.

13. A method of excising the INIR11 transgenic locus from the genome of the maize plant cell of any one of embodiments 1a, 1b, 2, or 3, comprising the steps of:
    (a) contacting the edited transgenic plant genome of the plant cell of embodiment 5 with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and,
    (b) selecting a transgenic plant cell, transgenic plant part, or transgenic plant wherein the INIR11 transgenic locus flanked by the OgRRS and the CgRRS has been excised.

14. The method of embodiment 13, wherein the INIR11 transgenic locus of the maize plant cell of claim 1 comprises the CgRRS of SEQ ID NO: 8, 9, or 10 and the guide RNA comprises an RNA sequence encoded by SEQ ID NO: 13.

15. The method of embodiment 14, wherein the maize plant cell comprises the INIR11 transgenic locus of SEQ ID NO: 3, 17, 23, or an allelic variant thereof.

EXAMPLES

Example 1. Introduction of a CgRRS in a 5' Junction Polynucleotides of a MON89034 Transgenic Locus Transgenic plant genomes containing one or more of the following transgenic loci (events) are contacted with:
    (i) an ABE or CBE and guide RNAs which recognize the indicated target DNA sites (protospacer (guide RNA coding) plus PAM site) in the 5' or 3' junction polynucleotides of the event to introduce a CgRRS in the junction polynucleotide;
    (ii) an RdDe and guide RNAs which recognize the indicated target DNA site (guide RNA coding plus PAM site) in the 5' or 3' junction polynucleotides of the event as well as a donor DNA template spanning the double stranded DNA break site in the junction polynucleotide to introduce a CgRRS in a junction polynucleotide.

Plant cells, callus, parts, or whole plants comprising the introduced CgRRS in the transgenic plant genome are selected.

TABLE 1

Examples of OgRRS and CgRRS in MON89034

| CORN EVENT NAME | OgRRS | CgRRS |
|---|---|---|
| MON89034 | (SEQ ID NO: 7; located in 3' junction polynucleotide of SEQ ID NO: 1) | (SEQ ID NO: 8; inserted into 5' junction polynucleotide) |
| | | (SEQ ID NO: 9; inserted into 5' junction polynucleotide) |
| | | (SEQ ID NO: 10; inserted into 5' junction polynucleotide) |

Example 2. Insertion of a CgRRS Element in the 5'-Junction of the MON89034 Event Two plant gene expression vectors are prepared. Plant expression cassettes for expressing a bacteriophage lambda exonuclease, a bacteriophage lambda beta SSAP protein, and an *E. coli* SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by example. DNA sequences encoding the c2 NLS-Exo, c2 NLS lambda beta SSAP, and c2NLS-SSB fusion proteins are operably linked to a OsUBI1, ZmUBI1, OsACT promoter and a OsUbi1, ZmUBI1, OsACT polyadenylation site respectively, to provide the exonuclease, SSAP, and SSB plant expression cassettes.

A DNA donor template sequence (SEQ ID NO: 11) that targets the 5'-T-DNA junction polynucleotide of the MON89034 event (SEQ ID NO:1) for HDR-mediated insertion of a base pair OgRRS sequence (SEQ ID NO: 7) that is identical to a Cas12a recognition site at the 3'-junction polynucleotide of the MON89034 T-DNA insert is constructed. The DNA donor sequence includes a replacement template with desired insertion region (27 base pairs long) flanked on both sides by homology arms about 500 to about 600 bp in length. The homology arms match (i.e., are homologous to) gDNA (genomic DNA) regions flanking the target gDNA insertion site (SEQ ID NO: 12). The replacement template region comprising the donor DNA is flanked at each end by DNA sequences identical to the MON89034

5'-T-DNA junction polynucleotide sequence recognized by a Cas12a RNA-guided nuclease and a gRNA (e.g., encoded by SEQ ID NO: 4).

A plant expression cassette that provides for expression of the RNA-guided sequence-specific Cas12a endonuclease is constructed. A plant expression cassette that provides for expression of a guide RNA (e.g., encoded by SEQ ID NO: 4) complementary to sequences adjacent to the insertion site is constructed. An *Agrobacterium* superbinary plasmid transformation vector containing a cassette that provides for the expression of the phosphinothricin N-acetyltransferas-esynthase (PAT) protein is constructed. Once the cassettes, donor sequence and *Agrobacterium* superbinary plasmid transformation vector are constructed, they are combined to generate two maize transformation plasmids.

A maize transformation plasmid is constructed with the PAT cassette, the RNA-guided sequence-specific endonuclease cassette, the guide RNA cassette, and the MON89034 5'-T_DNA junction sequence DNA donor sequence into the *Agrobacterium* superbinary plasmid transformation vector (the control vector).

A maize transformation plasmid is constructed with the PAT cassette, the RNA-guided sequence-specific endonuclease cassette, the guide RNA cassette, the SSB cassette, the lambda beta SSAP cassette, the Exo cassette, and the MON89034 5'-T DNA junction sequence donor DNA template sequence (SEQ ID NO: 11) into the *Agrobacterium* superbinary plasmid transformation vector (the lambda red vector).

All constructs are transformed into *Agrobacterium* strain LBA4404.

Maize transformations are performed based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination. Embryos are placed in an *Agrobacterium* suspension made with infection medium at a concentration of OD 600=1.0. Acetosyringone (200 µM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produced callus are transferred to Selection 1 medium with 7.5 mg/L phosphinothricin (PPT) and cultured for an additional 7 days. Callused embryos are placed on Selection 2 medium with 10 mg/L PPT and cultured for 14 days at 27-28° C. Growing calli resistant to the selection agent are transferred to Pre-Regeneration media with 10 mg/L PPT to initiate shoot development. Calli remained on Pre-Regeneration media for 7 days. Calli beginning to initiate shoots are transferred to Regeneration medium with 7.5 mg/L PPT in Phytatrays and cultured in light at 27-28° C. Shoots that reached the top of the Phytatray with intact roots are isolated into Shoot Elongation medium prior to transplant into soil and gradual acclimatization to greenhouse conditions.

When a sufficient amount of viable tissue is obtained, it can be screened for insertion at the MON89034 junction sequence, using a PCR-based approach. The PCR primer on the 5'-end is set forth in (SEQ ID NO: 14). The PCR primer on the 3'-end is set forth in SEQ ID NO: 15. The above primers that flank donor DNA homology arms are used to amplify the MON89034 5'-junction polynucleotide sequence. The correct donor sequence insertion will produce a bp product. A unique DNA fragment comprising the CgRRS in the MON89034 5' junction polynucleotide is set forth in SEQ ID NO: 16. Amplicons can be sequenced directly using an amplicon sequencing approach or ligated to a convenient plasmid vector for Sanger sequencing. Those plants in which the MON89034 junction sequence now contains the intended Cas12a recognition sequence are selected and grown to maturity. The T-DNA encoding the Cas12a reagents can be segregated away from the modified junction sequence in a subsequent generation. The resultant INIR11-3 transgenic locus (SEQ ID NO: 17) comprising the CgRRS and OgRRS (e.g., which each comprise SEQ ID NO: 7) can be excised using Cas12a and a suitable gRNA (e.g., comprising the gRNA encoded by SEQ ID NO: 13) which hybridizes to DNA comprising SEQ ID NO: 7 at both the OgRRS and the CgRRS.

The breadth and scope of the present disclosure should not be limited by any of the above-described embodiments.

What is claimed is:

1. A transgenic maize plant cell comprising an INIR11 transgenic locus comprising a DNA molecule having at least 95% sequence identity across the entire length of SEQ ID NO: 3, wherein the INIR11 transgenic locus comprises an originator guide RNA recognition site (OgRRS) and a cognate guide RNA recognition site (CgRRS), and wherein said CgRRS comprises the DNA molecule set forth in SEQ ID NO: 10.

2. The transgenic maize plant cell of claim 1, wherein said INIR11 transgenic locus comprises the DNA molecule set forth in SEQ ID NO: 3.

3. A transgenic maize plant part comprising the maize plant cell of claim 1.

4. The transgenic maize plant part of claim 3, wherein said maize plant part is a seed.

5. A transgenic maize plant comprising the maize plant cell of claim 1.

6. A method for obtaining a bulked population of inbred seed comprising selfing the transgenic maize plant of claim 5 and harvesting seed comprising the INIR11 transgenic locus from the selfed maize plant.

7. A method of obtaining hybrid maize seed comprising crossing the transgenic maize plant of claim 5 to a second maize plant which is genetically distinct from the first maize plant and harvesting seed comprising the INIR11 transgenic locus from the cross.

8. A DNA molecule comprising SEQ ID NO: 3.

9. A processed transgenic maize plant product comprising the DNA molecule of claim 8.

10. A biological sample containing the DNA molecule of claim 8.

11. A method of detecting a maize plant cell comprising the INIR11 transgenic locus of claim 1, comprising the step of detecting DNA molecule comprising SEQ ID NO: 10.

12. A method of excising the INIR11 transgenic locus from the genome of the maize plant cell of claim 1, comprising the steps of:
  (a) contacting the edited transgenic plant genome of the plant cell with: (i) an RNA dependent DNA endonuclease (RdDe); and (ii) a guide RNA (gRNA) capable of hybridizing to the guide RNA hybridization site of the OgRRS and the CgRRS of SEQ ID NO: 3; wherein the RdDe recognizes a OgRRS/gRNA and a CgRRS/gRNA hybridization complex; and
  (b) selecting a plant cell, plant part, or plant wherein the INIR11 transgenic locus flanked by the OgRRS and the CgRRS has been excised.

13. The method of claim 12, wherein the guide RNA comprises an RNA sequence encoded by SEQ ID NO: 13.

* * * * *

SEQUENCE LISTING

```
Sequence total quantity: 31
SEQ ID NO: 1           moltype = DNA   length = 12282
FEATURE                Location/Qualifiers
source                 1..12282
                       mol_type = other DNA
                       organism = synthetic construct
SEQUENCE: 1
aatatttaaa aatggaagta atactatatt aaaatgattc atgtggaact cctgcgcttc   60
tttttgaagt ttcaaaaggg agctttcagg gtcgcttaga gtttgtttgg ttggaaatac  120
aagcgaaaag agagctaatg aggggacat ccatatttc tatggtgttt gaataagagt   180
cacgcgggaa taagatgaac accgaaacaa ttttttttgta gctacgtggt tccaaaaaat  240
cgagtagacg gtgtcgcttc cacctcatac tacttcaacc tcaaaccaca catccttacg  300
cgcccgccgg tgtctccgtc gtctcaagtt ctcaacatac ctacacatgt aaccactacc  360
ggtctttgtc atgtttcgaa agaagattac aggtcctcta gaagagagga cgcggggtgg  420
cgagaaagct ggggaagaaa aaggctagta catatgattg gtctgtgaac ctgtgaggtg  480
ggtaggtagg taggtggaga tttttgttaa ctggtgttgt tgacgactc gaacggggcc   540
gggcgtgtgg tgtggctagc tgtggtggtt tgctcgccaa ccagccagcc acacatcagc  600
gagcatgcag agcttaagca tgtatgtacg gatcggcttg cttagcggtt aagggtgtgt  660
ttggtttggc ttttggcttt ggcttttgcc ccctaaaagc caaaagccaa ccaagggtgt  720
atttggtttg acttttggct tttggctttt gtccctaaa agccaaaagc caaacaaagg  780
gttagatcta ggaagcagct ttttctaaaa gctggctttc tcacagtgca aatctgaaag  840
```

```
caccccctgaa cctgctttta gtggcttttc gaatggaact gtgaaaacat atatcgaaga    900
acttttaacg acttttagtg gtttccacca aacagtttag cttttttaacg gcttacagcc    960
tacaacagct ttttccacag ctcacagccc acagcaactt ttttcacagc cacagcccaa   1020
ccaaacagac cccaaagggc tgaatccagg aagcagcttt ttctaaaagc cgactttctc   1080
gtagtgtaaa actgaaaaca cccctggacc tgcttttgag ggcttttgga tggaactgtg   1140
aaaacatata tcgaagaact tttaacgact tttagtggtt tccaccaaac gatttctagc   1200
ttttttaacag cacacagcct acaacagctt ttttcacagc tcacagccca caacaacttt   1260
ttctacagcc acaacccaac caaacggacc ctaaggcggc cgagcgagcg caaagcgtcg   1320
tcagctttga ttgccatgcc atctcctgct ccacttgtct ctctggccgt cgtcagccac   1380
catccaacaa ggccggtgct actggcggct cctaggtaga cgacgacgac gacgacacct   1440
ccaccgttcg ccgccgtcca ctcaccaatc aacacggaac gcccaaaaca cacacacacg   1500
cacgctgggg agggaaaaaa aggcagagac atatgcgtgc gtcgctgcat tattgtacgc   1560
gatcgaatgg catctctctc actctctctc ctcccttat taatctggta ctggctagct   1620
ggtccggcga caccgacgtg tcagctccgt cgcgcgcgtc cgtccgtccg ctggagcgga   1680
cacggaccgc ggcgtctgtc gatcgccggc tcgccgcagc gcagctacct agcacgctca   1740
cgcatgctac actgcctaca cgcacacggc cggcccaaaa gcgttccctg ccgcctgccg   1800
gccggctttt ttattattat tggaacatga ggctatttct cctcccacac gggctacgac   1860
gtgagcacga gtactgggat ccccgagatcc gccctcctg tccctgctgc tactccagca   1920
actgaaatgt tgtcagatga aacagcagag ccgatctccg cacggaaacc catgcacggc   1980
cattcaaatt caggtgccca cgtacgtcag ggtgctgctg ctactactat caagccaata   2040
aaaggatggt aatgagtatg atggatcagc aatgagtatg atggtcaata tggagaaaaa   2100
gaaagagtaa ttaccaattt tttttcaatt caaaaatgta gatgtccgca gcgttattat   2160
aaaatgaaag tacattttga taaaacgaca aattacgatc cgtcgtattt ataggcgaaa   2220
gcaataaaca aattattcta attcggaaat ctttatttcg acgtgtctac attcacgtcc   2280
aaatgggggc ttagatgaga aacttcacga tttggcgcgc caaagcttgg tcgagtggaa   2340
gctagcttc cgatcctacc tgtcacttca tcaaaaggac agtagaaaag gaaggtggct   2400
cctacaaatg ccatcattgc gataaaggaa aggccatcgt tgaagatgcc tctgccgaca   2460
gtggtcccaa agatggaccc ccacccacga ggagcatcgt ggaaaaagaa gacgttccaa   2520
ccacgtcttc aaagcaagtg gattgatgtg atatctccac tgacgtaagg gatgacgcac   2580
aatcccacta tccttcgcaa gacccttcct ctatataagg aagttcattt catttggaga   2640
ggacacgctg acaagctgac tctagcagat cctctagaac catcttccac acactcaagc   2700
cacactattg agaacacac agggacaaca caccataaga tccaagggag gcctccgccg   2760
ccgccggtaa ccaccccgcc cctctcctct ttctttctcc gttttttttt ccgtctcggt   2820
ctcgatcttt ggccttggta gtttgggtgg gcgagaggcg gcttcgtgcg cgcccagatc   2880
ggtgcgcggg aggggcggga tctcgcggct ggggctctcg ccggcgtgga tccggcccgg   2940
atctcgcggg gaatgggggct ctcggatgta gatctgcgat ccgccgttgt tgggggagat   3000
gatgggggt ttaaaattc cgccgtgcta aacaagatca ggaagagggg aaaagggcac   3060
tatggtttat atttttatat atttctgctg cttcgtcagg cttagatgtg ctagatcttt   3120
ctttctctt tttgtgggta gaatttgaat ccctcagcat tgttcatcgg tagtttttct   3180
tttcatgatt tgtgacaaat gcagcctcgt gcggagcttt tttgtaggta gaagtgatca   3240
accatggaca acaacccaaa catcaacgag tgcatcccgt acaactgcct cagcaaccct   3300
gaggtcgagg tgctcggcgg tgagcgcatc gagaccggtt acaccccccat cgacatctcc   3360
ctctccctca cgcagttcct gctcagccga ttcgtgccag gcgctggctt cgtcctgggc   3420
ctcgtggaca tcatctgggg catctttggc ccctcccagt gggacgcctt cctggtgcaa   3480
atcgagcagc tcatcaacca gaggatcgag gagttcgcca ggaaccaggc catcagccgc   3540
ctggagggcc tcagcaacct ctaccaaatc tacgctgaga gcttccgcga gtgggaggcc   3600
gaccccacta acccagctct ccgcgaggag atggcatcca agttcaacga catgaacagc   3660
gccctgacca ccgccatccc actcttcgcc gtccagaact accaagtccc gctcctgtcc   3720
gtgtacgtcc aggccgccaa cctgcacctc agcgtgctga gggacgtcag cgtgtttggc   3780
cagaggtggg gcttcgacgc cgccaccatc aacagccgct acaacgacct caccaggctg   3840
atcggcaact acaccgacca cgctgtccgc tggtacaaca ctggcctgga gcgcgtcggg   3900
ggccctgatt ctagagactg gattcgctac aaccagttca ggcgcgagct gaccctcacc   3960
gtcctggaca ttgtgtccct cttcccgaac tacgactccc gcacctaccc gatccgcacc   4020
gtgtcccaac tgacccgcga aatctacacc aaccccgtcc tggagaactt cgacggtagc   4080
ttcagggggca gcgcccaggg catcgagggc tccatcagga gcccacacct gatggacatc   4140
ctcaacagca tcactatcta caccgatgcc caccgcggcg agtactactg gtccggccac   4200
cagatcatgg cctccccggt cggcttcagc ggccccgagt ttaccttttcc tctctacggc   4260
acgatgggca acgccgctcc acaacaacgc atcgtcgctc agctgggcca gggcgtctac   4320
cgcacccctga gctccaccct gtaccgcagg cccttcaaca tcggtatcaa caaccagcag   4380
ctgtccgtcc tggatggcac tgagttcgcc tacggcacct cctccaacct gcccctccgct   4440
gtctaccgca agagcggcac ggtggattcc ctggacgaga tcccaccaca gaacaacaat   4500
gtgcccccca ggcagggttt ttcccacagg ctcagccacg tgtccatgtt ccgctccggc   4560
ttcagcaact cgtccgtgag catcatcaga gctcctatgt tctcttggat acaccgtagt   4620
gctgagttca acaacatcat tcatccgac agcattactc aaataccctt ggtgaaagca   4680
catacacttc agtcaggtac tactgttgtc agaggtccag ggtttacagg aggagacatt   4740
cttcgtcgca caagtggagg acccttgct tacactattg ttaacatcaa tggccaattg   4800
ccccaaaggt atcgtgcaag aatccgctat gcctctacta caaatctcag gatctacgtg   4860
actgttgcag gtgaaaggat ctttgctggt cagttcaaca agactatgga taccggtgac   4920
cctttgacat tccaatcttt tagctacgca actatcaaca cagcttttac attcccaatg   4980
agccagagta gcttcacagt aggtgctgac actttcagct cagggaatga agtttacatc   5040
gacaggtttg aattgattcc agttactgca accctcgagg ctgagtacaa ccttgagaga   5100
gcccagaagg ctgtgaacgc cctctttacc tccaccaatc agcttggctt gaaaactaac   5160
gttactgact atcacattga ccaagtgtcc aacttggtca cctaccttag cgatgagttc   5220
tgcctgcacg agaagcgtga actctccgag aaagttaaca acaggcagcc agaacgtggt   5280
gagaggaatc tcttgcaaga ctccaacttc aaagacatca acaggcagcc agaacgtggt   5340
tgggggtggaa gcacccggggat caccatccaa ggaggcgacg atgtgttcaa ggagaactac   5400
gtcacccctct ccggaacttt cgacgagtgc taccctacct acttgtacca agatcgat   5460
gagtccaaac tcaaagcctt caccaggtat caacttagag gctacatcga agacagccaa   5520
gaccttgaaa tctactcgat caggtacaat gccaagcacg agaccgtgaa tgtcccaggt   5580
```

```
actggttccc tctggccact ttctgcccaa tctcccattg ggaagtgtgg agagcctaac    5640
agatgcgctc cacaccttga gtggaatcct gacttggact gctcctgcag ggatggcgag    5700
aagtgtgccc accattctca tcacttctcc ttggacatcg atgtgggatg tactgacctg    5760
aatgaggacc tcggagtctg ggtcatcttc aagatcaaga cccaagacgg acacgcaaga    5820
cttggcaacc ttgagtttct cgaagagaaa ccattggtcg gtgaagctct cgctcgtgtg    5880
aagagagcag agaagaagtg gagggacaaa cgtgagaaac tcgaatggga aactaacatc    5940
gtttacaagg aggccaaaga gtccgtggat gctttgttcg tgaactccca atatgatcag    6000
ttgcaagccg caccaacat cgccatgatc cacgccgcag acaaacgtgt gcacagcatt    6060
cgtgaggctt acttgcctga gttgtccgtg atccctggtg tgaacgctgc catcttcgag    6120
gaacttgagg gacgtatctt taccgcattc tccttgtacg atgccagaaa cgtcatcaag    6180
aacggtgact tcaacaatgg cctcagctgc tggaatgtga aaggtcatgt ggacgtggag    6240
gaacagaaca atcagcgttc cgtcctggtt gtgcctgagt gggaagctga agtgtcccaa    6300
gaggttagag tctgtccagg tagaggctac attctccgtg tgaccgctta caaggaggga    6360
tacggtgagg gttgcgtgac catccacgag atcgagaaca acaccgacga gcttaagttc    6420
tccaactgcg tcgaggaaga aatctatccc aacaacaccg ttacttgcaa cgactacact    6480
gtgaatcagg aagagtacgg aggtgcctac actagccgta acagaggtta caacgaagct    6540
ccttccgttc ctgctgacta tgcctccgtg tacgaggaga atcctacac agatggcaga    6600
cgtgagaacc cttgcgagtt caacagaggt tacagggact acacaccact tccagttggc    6660
tatgttacca aggagcttga gtactttcct gagaccgaca aagtgtggat cgagatcggt    6720
gaaaccgagg gaaccttcat cgtggacagc gtggagcttc tcttgatgga ggaataatga    6780
gatctatcga ttctagaagg cctgaattct gcatgcgttt ggacgtatgc tcattcaggt    6840
tggagccaat ttggttgatg tgtgtgcgag ttcttgcgga catctctgta    6900
ttgtgttttct ttccccagtg ttttctgtac ttgtgtaatc ggctaatcgc caacagattc    6960
ggcgatgaat aaatgagaaa taaattgttc tgattttgag tgcaaaaaaa aaggaattag    7020
atctgtgtgt gttttttgga tccccggggc ggccgcgtta caagcttga gctcaggatt    7080
tagcagcatt ccagattggg ttcaatcaac aagtacgag ccatatcact ttattcaaat    7140
tggtatcgcc aaaaccaaga aggaactccc atcctcaaag gtttgtaagg aagaattctc    7200
agtccaaagc ctcaacaagg tcagggtaca gagtctccaa accattagcc aaaagctaca    7260
ggagatcaat gaagaatctt caatcaaagt aaactactgt tccagcacat gcatcatggt    7320
cagtaagttt cagaaaaaga catccaccga agactttaag ttagtgggca tctttgaaag    7380
taatcttgtc aacatcgagc agctggcttg tggggaccag acaaaaaagg aatggtgcag    7440
aattgttagg cgcacctacc aaaagcatct ttgcctttat tgcaaagata aagcagattc    7500
ctctagtaca agtggggaac aaaataacgt ggaaagagc tgtcctgaca gcccactcac    7560
taatgcgtat gacgaacgca gtgacgacca caaaagaatt ccctctatat aagaaggcat    7620
tcattcccat ttgaaggatc atcagatact caaccaatcc ttctaggatc taccgtcttc    7680
ggtacgcgct cactccgccc tctgcctttg ttactgccac gttttctga atgctctctt    7740
gtgtggtgat tgctgagagt ggtttagctg gatctagaat tacactctga aatcgtgttc    7800
tgcctgtgct gattacttgc cgtccttttgt agcagcaaaa tatagggaca tggtagtacg    7860
aaacgaagat agaacctaca cagcaatacg agaaatgtgt aatttggtgc ttagcggtat    7920
ttatttaagc acatgttggt gttatagggc acttggattc agaagtttgc tgttaattta    7980
ggcacaggct tcatactaca tgggtcaata gtataggggat tcatattata ggcgatacta    8040
taataattg ttcgtctgca gagcttatta tttgccaaaa ttagatattc ctattctgtt    8100
tttgtttgtg tgctgttaaa ttgttaacgc ctgaaggaat aaatataaat gacgaaattt    8160
tgatgtttat ctctgctcct ttattgtgac cataagtcaa gatcagatgc acttgttta    8220
aatattgttg tctgaagaaa taagtactga cagtattttg atgcattgat ctgcttgttt    8280
gttgtaacaa aatttaaaa taaagagttt ccttttttgtt gctctcctta cctcctgatg    8340
gtatctagta tctaccaact gacactatat tgcttctctt tacatacgta tcttgctcga    8400
tgccttctcc ctagtgttga ccagtgttac tcacatagtc tttgctcatt tcattgtaat    8460
gcagatacca agcggcctct agaggatcag catggcgccc accgtgatga tggcctcgtc    8520
ggccaccgcc gtcgctccgt tccagggggct caagtccacc gccagcctcc ccgtcgcccg    8580
ccgtcctcc agaagcctcg gcaacgtcag caacggcgga aggatccggt gcatgcaggt    8640
aacaaatgca tcctagctag tagttctttg cattgcagca gctgcagcta gcgagttagt    8700
aataggaagg gaactgatga tccatgcatg gactgatgtg tgttgcccat cccatcccat    8760
ttcccaaccc caaacgaacc aaaacacacg tactacgtgc aggtgtggcc ggcctacggc    8820
aacaagaagt tcgagacgct gtcgtacctg ccgccgctgt cgaccggcgg gcgcatccgc    8880
tgcatgcagg ccatggacaa ctccgtcctg aactctggtc gcaccaccat ctgcgacgct    8940
tacaacgtcg cggcgcatga tccattcagc ttccagcaca agagcctcga cactgttcag    9000
aaggagtgga cggagtggaa gaagaacaac cacagcctgt acctggaccc catcgtcggc    9060
acggtggcca gcttccttct caagaaggtc ggctctctcg tcgggaagcg catcctctcg    9120
gaactccgca acctgatctt tccatctggc tccaccaacc tcatgcaaga catcctcagg    9180
gagaccgaga agtttctcaa ccagcgcctc aacactgata cccttgctcg cgtcaacgct    9240
gagctgacgg gtctgcaagc aaacgtggag gagttcaacc gccaagtgga caacttcctc    9300
aaccccaacc gcaatgcggt gcctctgtcc atcacttctt ccgtgaacac catgcaacaa    9360
ctgttcctca accgcttgcc tcagttccag atgcaaggct accagctgct cctgctgcca    9420
ctctttgctc aggctgccaa cctgcacctc tccttcattc gtgacgtgat cctcaacgct    9480
gacgagtggg gcatctctgc agccacgctg aggacctacc gcgactacct gaagaactac    9540
accagggact actccaacta ttgcatcaac acctaccagt cggccttcaa gggcctcaat    9600
acgaggcttc acgacatgct ggagttcagg acctacatgt tcctgaacgt gttcgagtac    9660
gtcagcatct ggtcgctctt caagtaccag agcctgcagg tgtccagcgg cgccaactc    9720
tacgccagcg gctctggtcc ccaacaaact cagagcttca ccagccagga ctggccattc    9780
ctgtattcgt tgttccaagt caactccaac tacgtcctca acggcttctc tggtgctcgc    9840
ctctccaaca ccttccccaa cattgttggc ctccccggct ccaccacaac tcatgctctg    9900
cttgctgcca gagtgaacta ctccggcggc atctcgagcg gcgacattgg tgcatcgccg    9960
ttcaaccaga acttcaactg ctccacctc ctgccgccgc tgctcacccc gttcgtgagg    10020
tcctggctcg acagcggctc cgaccgcgag ggcgtggcca ccgtcaccaa ctggcaaacc    10080
gagtccttcg agaccaccct tggctccgg agcggcgcct tcacggcgcg tggaaattct    10140
aactacttcc ccgactactt catcaggaac atctctggtc ttcctctcgt cgtccgcaac    10200
gaggacctcc gccgtccact gcactacaac gagatcagga acatcgcctc tccgtccggg    10260
acgcccggag gtgcaagggc gtacatggtg agcgtccata acaggaagaa caacatccac    10320
```

-continued

```
gctgtgcatg agaacggctc catgatccac ctggcgccca atgattacac cggcttcacc  10380
atctctccaa tccacgccac ccaagtgaac aaccagacac gcaccttcat ctccgagaag  10440
ttcggcaacc agggcgactc cctgaggttc gagcagaaca acaccaccgc caggtacacc  10500
ctgcgcggca acggcaacag ctacaacctg tacctgcgcg tcagctccat ggcaactcc   10560
accatcaggg tcaccatcaa cgggagggtg tacacagcca ccaatgtgaa cacgacgacc  10620
aacaatgatg gcgtcaacga caacggcgcc cgcttcagcg acatcaacat ggcaacgtg   10680
gtggccagca gcaactccga cgtcccgctg gacatcaacg tgaccctgaa ctctggcacc  10740
cagttcgacc tcatgaacat catgctggtg ccaactaaca tctcgccgct gtactgatag  10800
gagctctgat ccccatggga attcccgatc gttcaaacat ttggcaataa agtttcttaa  10860
gattgaatcc tgttgccggt cttgcgatga ttatcatata atttctgttg aattacgtta  10920
agcatgtaat aattaacatg taatgcatga cgttatttat gagatgggtt tttatgatta  10980
gagtcccgca attatacatt taatacgcga tagaaaacaa aatatagcgc gcaaactagg  11040
ataaattatc gcgcgcggtg tcatctatgt tactagatcg gggatatccc cggggcggcc  11100
gcggggaatt cggtaccaag cttggcgcg ccaaatcgtg aagttctca tctaagcccc   11160
catttggacg tgaatgtaga cacgtcgaaa taaagatttc cgaattagaa taatttgttt  11220
attgctttcg cctataaata cgacggatcg taatttgtcg tttatcaaa atgtactttc   11280
atttttataat aacgctgcgg acatctacat ttttgaattg aaaaaaaatt ggtaattact  11340
cttctttttt ctccatattg accatcatac tcattgcatc cccggaaatt atgttttttt  11400
aaaaaccacg gtattataga taccgtgtta tttttgagt attggaaatt tcatttcaac   11460
ccaaagtttc ttcatggcac atctagcttt tgcctaatac catgtagggc tacatcttaa   11520
aaatctatac tactatatta aagctgcagg gtagcctgt ctccacctgg ttctgcctcg    11580
agccaatcta aaccgtccat ctatatccat caaatccggtc cgtcccgtc cgtcgcgacc  11640
tcctctcccg ctattcagtt gcatacttgc agcaggttct ccctcctcac catttcctct   11700
gcctcctctc tcgctcactg gtcagattca tcctgcctct cccgcatgcg ctccctcccc   11760
atgccccgtc tcgcactatc gccacacctc accgcgggga gacgaagacg gtggacgcat  11820
cctcacctcc tccgctcagtt gtcgctcttc catcctcttc aacaacttct acataaggag 11880
aggcggttcg gcgtcccgac gccgccgctt ctccctccc catggaggac gagaacatcg   11940
acctcggcgg cggggggcgat gcctccgctc tgcatagagg agggttgtag tggcaagcag  12000
caatgccaac accgaggcgg gccaagacta ggcaacaata ggacggcacg cccggttgtc   12060
agcgaggtgg cggcatcgtg tgccgctacc gaacaacatc tccggcgctg gagtcggtga  12120
gttactgcgc cacccggacg ccctcaatgc actgatatct acccggtctc catcgccgcc  12180
cttcctccct tccctctccc tgtgcctccc tctcttgccc tctcccttcc aactgctccc   12240
gccccagccc tagcccaacc acctcccgcg cagggtcacc aa                     12282
```

```
SEQ ID NO: 2           moltype = DNA   length = 12275
FEATURE                Location/Qualifiers
source                 1..12275
                       mol_type = other DNA
                       organism = synthetic construct
SEQUENCE: 2
aatatttaaa aatggaagta atactatatt aaaatgattc atgtggaact cctgcgcttc   60
tttttgaagt ttcaaaaggg agctttcagg gtcgcttaga gtttgtttgg ttggaaatac   120
aagcgaaaag agagctaatg aggggacat ccatatttc tatgtgtttt gaataagagt     180
cacgcgggaa taagatgaac accgaaacaa tttttttgta gctacgtggt tccaaaaaat   240
cgagtagacg gtgtcgcttc cacctcatac tacttcaacc tcaaaccaca catccttacg   300
cgcccgccgg tgtctccgtc gtctcaagtt ctcaacatac ctacacatgt aaccactacc   360
ggtcttttgtc atgtttcgaa agaagattac aggtcctcca gaagagagga cgcggggtgg  420
cgagaaagct ggggaagaaa aaggctagta catatgattg gtctgtgaac ctgtgaggtg   480
ggtaggtagg taggtggaga ttttttgttaa ctggtgttgt tgacggactc gaacggggcc   540
gggcgtgtgg tgtggctagc tgtggtggtt tgctcgccag ccagccagcc acacatcagc   600
gagcatgcag agcttaagca tgtatgtacg gatcggcttg cttagcggtt aagggtgtgg   660
ttggttttggc ttttggcttt ggcttttgcc cctaaaagc caaaagccaa ccaagggtgt    720
atttggtttg acttttggct tttggctttt gtccccaaaa agccaaaagc caaacaaagg   780
gttagatcta ggaagcagct ttttctaaaa gctggctttc tcacagtgca aatctgaaag   840
cacccctgaa cctgcttta gtggcttttc gaattgaaaat atatcgaaga                900
actttttaacg acttttagtg gtttccacca aacagtttag cttttttaacg gcttacagcc  960
tacaacagct ttttccacag ctcacagccc acagcaactt ttttcacagc cacagcccaa   1020
ccaaacagac cccaaagggc tgaatccagg aagcagcttt ttctaaaagc cgactttctc   1080
gtagtgtaaa actgaaaaca cccctggacc tgctttttagt ggcttttgga tggaactgtg  1140
aaaacatata tcgaagaact tttaacgact tttagtggtt tccaccaaac gattctagc    1200
tttttaacag cacacagcct acaacagctt ttttcacagc tcacagccca caacaacttt   1260
ttctacagcc acaacccaac caaacgacc ctaaggcggc cgagcgagcg caaagcgtcg   1320
tcagctttga ttgccatgcc atctcctgct ccacttgtct ctctggccgt cgtcagccac  1380
catccaacaa ggccggtgct actggcggct cctaggtaga cgacgacgac gacgacctt    1440
ccaccgttcg ccgccgtcca ctcaccaatc aacacggaac gcccaaaaca cacacacacg   1500
cacgctgggg agggaaaaa aggcagagac atatgcgtgc gtcgctgcat tattgtacgc   1560
gatcgaatgc catctctctc actctctctc ctcccttat taatctggta ctggctagct    1620
ggtccggcga caccgacgtg tcagctccgt cgcgcgcgtc cgtccgtccg ctggagcgga   1680
cacggaccgc ggcgtctgtc gatcgccggc tcgccgcagc gcagctactt agcacgctca   1740
cgcatgctac actgcctaca cgcacacggc cggcccaaaa gcgttccctg ccgcctgcca   1800
gccggctttt ttattattat tggaaacatga ggctatttct cctcccacac gggctacgac   1860
gtgagcacga gtactgggat ccccggatcc gccctctctg tccctgctgc tactccagcc  1920
actgaaatgt tgtcagatga aacagcagag ccgatctccg cacggaaacc catgcacggc   1980
cattcaaatt caggtgccca cgtactgtcag ggtgctgtgc tctactactat caagccaata  2040
aaaggatgt aatgagtatg atggatcagc atgatggtca atatggagaa aaagaaaagag  2100
taattaccaa ttttttttca attcaaaaat gtagatgtcc gcagcgttat tataaaaatga  2160
aagtacattt tgataaaacg acaaaatacg atccgtcgta tttataggcg aaagcaataa   2220
acaaattatt ctaattcgga aatctttatt tcgacgtgtc tacattcacg tccaaatggg    2280
ggcttagatg agaaacttca cgatttggcg cgccaaagct tggtcgagtg gaagctagct   2340
```

```
ttccgatcct acctgtcact tcatcaaaag gacagtagaa aaggaaggtg gctcctacaa  2400
atgccatcat tgcgataaag gaaaggccac cgttgaagat gcctctgccg acagtggtcc  2460
caaagatgga cccccaccca cgaggagcat cgtggaaaaa gaagacgttc aaccacgtc   2520
ttcaaagcaa gtggattgat gtgatatctc cactgacgta agggatgacg cacaatccca  2580
ctatccttcg caagacccttt cctctatata aggaagttca tttcatttgg agaggacacg  2640
ctgacaagct gactctagca gatcctctag aaccatcttc cacacactca agccacacta  2700
ttggagaaca cacagggaca acacaccata agatccaagg gaggcctccg ccgccgccgg  2760
taaccacccc gcccctctcc tctttctttc tccgtttttt tttccgtctc ggtctcgatc  2820
tttggccttg gtagtttggg tgggcgagag gcggcttcgt gcgcgcccag atcggtgcgc  2880
gggaggggcg ggatctcgcg gctggggctc tcgccggcgt ggatccggcc cggatccgca  2940
ggggaatggg gctctcggat gtagatctgc gatccgccgt tgttgggga gatgatgggg   3000
ggtttaaaat ttccgccgtg ctaaacaaga tcaggaagag gggaaaaggg cactatggtt  3060
tatatttta tatatttctg ctgcttcgtc aggcttagat gtgctagatc tttctttctt   3120
cttttttgtgg gtagaatttg aatccctcag cattgttcat cggtagtttt tcttttcatg  3180
atttgtgaca aatgcagcct cgtgcgagc tttttgtag gtagaagtga tcaaccatgg   3240
acaacaaccc aaacatcaac gagtgcatcc cgtacaactg cctcagcaac cctgaggtcg  3300
aggtgctcgg cggtgagcgc atcgagaccg gttacacccc catcgacatc tccctctccc  3360
tcacgcagtt cctgctcagc gagttcgtgc caggcgctgg cttcgtcctg ggcctcggca  3420
acatcatctg gggcatcttt ggcccctccc agtgggacgt cttcctggtg caaatcgagc  3480
agctcatcaa ccagaggatc gaggagttcg ccaggaacca ggccatcagc cgcctggagg  3540
gcctcagcaa cctctaccaa atctacgctg agagcttccg cgagtgggag gccgacccca  3600
ctaacccagc tctccgcgag gagatgcgca tccagttcaa cgacatgaac agcgccctga  3660
ccaccgccat cccactcttc gccgtccaga actaccaagt cccgctcctg tccgtgtacg  3720
tccaggccgc caacctgcac ctcagcgtgc tgagggacgt cagcgtgttt ggccagaggt  3780
ggggcttcga cgccgccacc atcaacagcc gctacaacga cctcaccagg ctgatcggca  3840
actacaccga ccacgctgtc cgctggtaca acactgcgtc ggagcgcgtc tgggccctgg  3900
attctagaga ctggattcgc tacaaccagt tcaggcgcga gctgaccctc accgtcctga  3960
acattgtgtc cctcttcccg aactacgact cccgcaccta cccgatccgc accgtgtccc  4020
aactgacccg cgaaatctac accaacccg tcctggagaa cttcgacggt agcttcaggg  4080
gcagcgccca gggcatcgag ggctccatca ggagcccaca cctgatggac atcctcaaca  4140
gcatcactat ctacaccgat gcccaccgcg gcgagtacta ctggtccggc caccagatca  4200
tggcctcccc ggtcggcttc agcggcccg agtttacctt tcctctctac ggcacgatgg  4260
gcaacgccgc tccacaacaa cgcatcgtcg ctcagctggg ccaggcgtc taccgcaccc  4320
tgagctccac cctgtaccgc aggccttca acatcggtat caacaaccag cagctgtccg  4380
tcctggatgg cactgagttc gcctacggca cctcctccaa cctgccctcc gctgtctacc  4440
gcaagagcgg cacggtggat tccctggacg agatcccacc acagaacaac aatgtgcccc  4500
ccaggcaggg ttttttccac aggctcagcc acgtgtccat gttccgctcc ggcttcagca  4560
actcgtccgt gagcatcatc agagctccta tgttctcttg gatacaccgt agtgctgagt  4620
tcaacaacat cattgcatcc gacagcatta ctcaaatacc cttggtgaaa gcacatacac  4680
ttcagtcagg tactactgtt gtcagaggtc cagggtttaa aggaggagac attcttcgtc  4740
gcacaagtgg aggacccttt gcttacacta ttgttaacat caatgccaa ttgccccaaa   4800
ggtatcgtgc aagaatccgc tatgcctcta ctacaaatct caggatctac gtgactgttg  4860
caggtgaaag gatctttgct ggtcagttca acaagactag caacaccggt gaccctttga  4920
cattccaatc ttttagctac gcaactatca acacagcttt tacattccca atgagccaga  4980
gtagcttcac agtaggtgct gacactttca gctcagggaa tgaagtttac atcgacaggt  5040
ttgaattgat tccagttact gcaaccctcg aggctgagta caaccttgag agagcccaga  5100
aggctgtgaa cgccctcttt acctccacca atcagcttgg cttgaaaact aacgttactg  5160
actatcacat tgaccaagtg tccaacttgg tcacctacct tagcgatgag ttctgcctcg  5220
acgagaagcg tgaactctcc gagaaagtta aacacgccaa gcgtctcagc gacgagagga  5280
atctcttgca agactccaac ttcaaagaca tcaacaggca gccagaacgt ggttgggtg   5340
gaagcaccgg gatcaccatc caaggaggcg acgatgtgtt caaggagaac tacgtcaccg  5400
tctccggaac tttcgacgag tgctacccta cctacttgta ccagaagatc gatgagtcca  5460
aactcaaagc cttcaccagg tatcaactta gaggctacat cgaagacagc caagaccttg  5520
aaatctactc gatcaggtac aatgccaagc acgagaccgt gaatgtccca ggtactggtt  5580
ccctctggcc actttctgcc caatctccca ttgggaagtg tggagagcct aacagatgga  5640
ctccacacct tgagtggaat cctgacttgg actgctcctg cagggatggc gagaagtgtg  5700
cccaccattc tcatcacttc tccttggaca tcgatgtggg atgtactgac ctgaatgagg  5760
acctcggagt ctgggtcatc ttcaagatca agacccaaga cggacacgca agacttggca  5820
accttgagtt tctcgaagag aaaccattgg tcggtgaagc tctcgctcgt gtgaagagag  5880
cagagaagaa gtggagggac aaacgtaaga aactcgaatg ggaaactaac atcgtttaca  5940
aggaggccaa agagtccgtg gatgctttgt tcgtgaactc ccaatatgat cagttgcaag  6000
ccgacaccaa catcgccatg atccacgccg cagacaaacg tgtgcacagc attcgtgagg  6060
cttacttgcc tgagttgtcc gtgatccctg tgtgtaacgc tgccatcttc gaggaacttg  6120
agggacgtat ctttaccgca ttctcttgt acgatgccag aaacgtcatc aagaacgtga  6180
acttcaacaa tggcctcagc tgctggaatg tgaaaggtca tgtcgacgtg gaggaacaga  6240
acaatcagct ttccgtcctg gttgtgcctg agtgggaagc tgaagtgtcc aagaggtta   6300
gagtctgtcc aggtagaggc tacattctcc gtgtgaccgc ttacaaggag ggatacggtg  6360
agggttcgt gaccatccac gagatcgaga acaacaccgga cgagcttaag ttctccaact  6420
gcgtcgagga agaaatctat cccaacaaca ccgttacttg caacgactac actgtgaatc  6480
aggaagagta cggaggtgcc tacactagcc gtaacagagg ttaacaacgaa gctccttccg  6540
ttcctgctga ctatgcctcc gtgtacgagg agaaatccta cacagatggc agacgtgaga  6600
acccttgcga gttcaacaga ggttacaggg actacacacc acttccagtt ggctatgtta  6660
ccaaggagct tgagtacttt cctgagaccg acaaagtgtg gatcgagatc ggtgaaaccg  6720
agggaacctt catcgtggac agcgtggagc ttctcttgat ggaggaataa tgagatctat  6780
cgattctaga aggcctgaat tctgcatgcg tttggacgta tgctcattca ggttggagcc  6840
aatttggttg atgtgtgtgc gagttcttgc gagtctgatg agacatctct gtattgtgtt  6900
tctttcccca gtgtttctg tacttgtgta atcggctaat cgccaacaga ttcggcgatg  6960
aataaatgag aaataaattg ttctgatttt gagtgcaaaa aaaaggaat tagatctgtg  7020
tgtgtttttt ggatccccgg ggcggccgcg ttaacaagct tgagctcagg atttagcagc  7080
```

```
attccagatt gggttcaatc aacaaggtac gagccatatc actttattca aattggtatc   7140
gccaaaacca agaaggaact cccatcctca aaggtttgta aggaagaatt ctcagtccaa   7200
agcctcaaca aggtcagggt acagagtctc caaaccatta gccaaaagct acaggagatc   7260
aatgaagaat cttcaatcaa agtaaactac tgttccagca catgcatcat ggtcagtaag   7320
tttcagaaaa agacatccac cgaagactta aagttagtgg gcatctttga aagtaatctt   7380
gtcaacatcg agcagctggc ttgtggggac cagacaaaaa aggaatggtg cagaattgtt   7440
aggcgcacct accaaaagca tctttgcctt tattgcaaag ataaagcaga ttcctcctagt  7500
acaagtgggg aacaaaataa cgtggaaaag agctgtcctg acagcccact cactaatgcg   7560
tatgacgaac gcagtgacga ccacaaaaga attccctcta tataagaagg cattcattcg   7620
catttgaagg atcatcagat actcaaccaa tccttctagg atctaccgtc ttcggtacgc   7680
gctcactccg ccctctgcct ttgttactgc cacgtttctc tgaatgctct cttgtgtggt   7740
gattgctgag agtggtttag ctggatctag aattacactc tgaaatcgtg ttctgcctgt   7800
gctgattact tgccgtcctt tgtagcagca aaatataggg acatggtagt acgaaacgaa   7860
gataaacct acacagcaat acgagaaatg tgtaatttgg tgcttagcgg tatttattta    7920
agcacatgtt ggtgttatag ggcacttgga ttcagaagtt tgctgttaat ttaggcacag   7980
gcttcatact acatgggtca atagtatagg gattcatatt ataggcgata ctataataat   8040
ttgttcgtct gcagagctta ttatttgcca aaattagata ttcctattct gttttttgttt  8100
gtgtgctgtt aaattgttaa cgcctgaagg aataaatata aatgacgaaa ttttgatgtt   8160
tatctctgct cctttattgt gaccataagt caagatcaga tgcacttgtt ttaaatattg   8220
ttgtctgaag aaataagtac tgacagtatt ttgatgcatt gatctgcttg tttgttgtaa   8280
caaaatttaa aaataaagag tttccttttt gttgctctcc ttacctcctg atggtatcta   8340
gtatctacca actgacacta tattgcttct ctttacatac gtatcttgct cgatgcctc    8400
tccctagtgt tgaccagtgt tactcacata gtctttgctc atttcattgt aatgcagata   8460
ccaagcggcc tctagaggat cagcatggcg cccaccgtga tgatggcctc gtcggccacc   8520
gccgtcgctc cgttccaggg gctcaagtcc accgccagcc tccccgtcgc ccgccgctcc   8580
tccagaagcc tcggcaacgt cagcaacggc ggaaggatcc ggtgcatgca ggtaacaaat   8640
gcatcctagc tagtagttct ttgcattgca gcagctgcag ctagcgagtt agtaatagga   8700
agggaactga tgatccatgc atggactgat gtgtgttgcc catcccatcc catttcccaa   8760
ccccaaacga accaaaacac acgtactacg tgcaggtgtg gccggcctac ggcaacaaga   8820
agttcgagac gctgtcgtac ctgccgccgc tgtcgacgg cccggcgcatc cgctgcatgc   8880
aggccatgga caactccgtc ctgaactctg gtcgcaccac catctgcgac gcctacaacg   8940
tcgcggcgca tgatccattc agcttccagc acaagagcct cgacactgtt cagaaggagt   9000
ggacggagtg gaagaagaac aaccacagcc tgtacctgga ccccatcgtc ggcacggtgg   9060
ccagcttcct tctcaagaag gtcggctctc tcgtcgggaa gcgcatcctc tcggaactcc   9120
gcaacctgat ctttccatct ggctccacca acctcatgca agacatcctc agggagaccg   9180
agaagtttct caaccagcgc ctcaacactg atacccttgc tcgcgtcaac gctgagctga   9240
cgggtctgca agcaaacgtg gaggagttca accgccaagt ggacaacttc ctcaaccccca  9300
accgcaatgc ggtgcctctg tccatcactt cttccgtgaa caccatgcaa caactgttcc   9360
tcaacccgctt gcctcagttc cagatgcaag gctaccagct gctcctgctg ccactctttg  9420
ctcaggctgc caacctgcac ctctccttca ttcgtgacgt gatcctcaac gctgacgagt   9480
ggggcatctc tgcagccacg ctgaggacct accgcgacta cctgaagaac tacaccaggg   9540
actactccaa ctattgcatc aacacctacc agtcggcctt caagggcctc aatacgaggc   9600
ttcacgacat gctggagttc cagacca tgttcctgaa cgtgttcgag tacgtcagca     9660
tctggtcgct cttcaagtac cagagcctgc tggtgtccag cggcgccaac ctctacgcca   9720
gcggctctgg tccccaacaa actcagagct tcaccagcca ggactggcca ttcctgtatt   9780
cgttgttcca agtcaactcc aactacgtcc tcaacgcctt ctctggtgct cgcctctcca   9840
acaccttccc caacattgtt ggcctccccg gctccaccac aactcatgct ctgcttgctg   9900
ccagagtgaa ctactccggc ggcatctcga gcgcgacat tggtgcatcg ccgttcaacc    9960
agaacttcaa ctgctccacc ttcctgccgc gctgctcac cccgttcgtg aggtcctggc   10020
tcgacagcgc ctccgaccgc gagggcgtgg ccaccgtcac caactggcaa accgagtcct   10080
tcgagaccac ccttggcctc cggagcggcg ccttcacgg gcgtgaaat tctaactact   10140
tccccgacta cttcatcagg aacatcctg gtgttcctct cgtcgtccgc aacgaggacc   10200
tccgccgtcc actgcactac aacgagatca ggaacatcgc ctctccgtcc gggacgcccg   10260
gaggtgcaag ggcgtacatg gtgagcgtcc ataacaggaa gaacaacatc cacgctgtgc   10320
atgagaacgg ctccatgatc cacctggcgc ccaatgatta caccggcttc accatctctc   10380
caatccacgc cacccaagtg aacaaccaga cacgcacctt catctccgag aagttcggca   10440
accagggcga ctccctgagg ttcgagcaga acaacaccac cgccaggtac accctcgcgc   10500
gcaacggcaa cagctacaac ctgtacctgc gcgtcagctc cattggcaac tccaccatca   10560
gggtcaccat caacggggagg gtgtgcacag ccaccaatgt gaacacgacg accaacaatg   10620
atgccgtcaa cgacaacggc gcccgcttca gcgacatcaa cattggcaac gtggtggcca   10680
gcagcaactc cgacgtcccg ctggacatca acgtgaccct gaactctggc acccagttcg   10740
acctcatgaa catcatgctg gtgccaacta acatctcgcc gctgtactga taggagctct   10800
gatccccatg ggaattcccg atcgttcaaa catttggcaa taaagtttct taagattgaa   10860
tcctgttgcc ggtcttgcga tgattatcat ataatttctg ttgaattacg ttaagcatgt   10920
aataattaac atgtaatgca tgacgttatt tatgagatgg gtttttatga ttagagtccc   10980
gcaattatac atttaatacg cgatagaaaa caaaatatag cgcgcaaact aggataaatt   11040
atcgcgcgcg gtgtcatcta tgttactaga tcggggatat ccccgggggcg gccgcgggga  11100
attcggtacc aagcttttgg gcgcaaaatc gtgaagtttc tcatctaagc cccccattgg   11160
acgtgaatgt agacacgtcg aaataaagat ttccgaatta gaataatttg tttattgctt  11220
tcgcctataa atacgacgga tcgtaatttg tcgttttatc aaaatgtact tcattttta    11280
aataacgctg cggacatcta cattttgaa ttgaaaaaaa attgtaatt actctttctt     11340
tttctccata ttgaccatca tactcattgc atccccggaa attatgtttt tttaaaaacc   11400
acggtattat agataccgtg ttatttttg agtattggaa atttcatttc aacccaaagt    11460
ttcttcatgg cacatctagc tttttgcctaa taccatgtag ggctacatct taaaaatcta   11520
tactactata ttaaagctgc agggggtagcc tgtctccacc tggttctgcc tcgagcaat    11580
ctaaaccgtc catctatatc catcaaatca gcaccgtccg gtccgtgcgc acctcctctc   11640
ccgctattca gttgcatact tgcagcaggt tctccctcct caccatttcc tctgcctcct   11700
ctctcgctca ctggtcagat tcatcctgcc tctcccgcat gcgctccctc ccatgcccc    11760
gtctcgcact atcgccacac ctcaccgcgg ggagacgaag acggtggacg catcctcacc   11820
```

```
tcctccgcta gttgtcgctc ttccatcctc ttcaacaact tctacatagg gagaggcggt    11880
tcggcgtccc gacgccgccg cttctcccct ccccatggag gacgagaaca tcgacctcgg    11940
cggcggggc gatgcctccg ctctgcatag aggaggttg tagtggcaag cagcaatgcc     12000
aacaccgagg cgggccaaga ctaggcaaca ataggacggc acgcccggtt gtcagcgagg    12060
tggcggcatc gtgtgccgct accgaacaac atctccggcg ctggagtcgg tgagttactg    12120
cgccacccgg acgccctcaa tgcactgata tctaccggt ctccatcgcc gcccttcctc     12180
ccttccctct ccctgtgcct ccctctcttg ccctctccct tccaactgct cccgcccag     12240
ccctagccca accacctccc gcgcagggtc accaa                               12275

SEQ ID NO: 3          moltype = DNA    length = 12240
FEATURE               Location/Qualifiers
source                1..12240
                      mol_type = other DNA
                      organism = synthetic construct
SEQUENCE: 3
aatatttaaa aatggaagta atactatatt aaaatgattc atgtggaact cctgcgcttc    60
ttttttgaagt ttcaaaaggg agctttcagg gtcgcttaga gtttgtttgg ttggaaatac   120
aagcgaaaag agagctaatg aggggggacat ccatattttc tatggtgttt gaataagagt   180
cacgcgggaa taagatgaac accgaaacaa ttttttttgta gctacgtggt tccaaaaaat   240
cgagtagacg gtgtcgcttc cacctcatac tacttcaacc tcaaaccaca catccttacg    300
cgcccgccgg tgtctccgtc gtctcaagtt ctcaacatac ctacacatgt aaccactacc    360
ggtcttttgtc atgtttcgaa agaagattac aggtcctgca gaagagagga cgcggggtag   420
cgagaaagct ggggaagaaa aaggctagta catatgattg gtctgtgaac ctgtgaggtg    480
ggtaggtagg taggtggaga ttttttgttaa ctggtgttgt tgacggactc gaacggggcc   540
gggcgtgtg tgtggctagc tgtggtggtt tgctcgccag ccagccagcc acacatcagc    600
gagcatgcag agcttaagca tgtatgtacg gatcggcttg cttagcggtt aagggtgtgt   660
ttggtttggc ttttggcttt ggcttttgcc ccctaaaagc caaaagccaa ccaagggtgt   720
atttggtttg acttttggct tttggctttt gtccctaaa agccaaaagc caaacaaagg    780
gttagatcta ggaagcagct ttttctaaaa gctggctttc tcacagtgca aatctgaaag   840
caccccctga cctgcttta gtggcttttc gaatgaaact gtgaaaacat atatcgaaga   900
acttttaacg acttttagtg gtttccacca aacagtttag cttttttaacg gcttacagcc   960
tacaacagct ttttccacag ctcacagccc acagcaactt ttttcacagc cacagcccaa   1020
ccaaacagac cccaaagggc tgaatccagg aagcagcttt ttctaaaagc cgactttctc   1080
gtagtgtaaa actgaaaaca cccctggacc tgcttttagt ggcttttgga tggaactgtg   1140
aaaacatata tcgaagaact tttaacgact tttagtggtt tccaccaaac gatttctagc   1200
ttttttaacag cacacagcct acaacagctt ttttcacagc tcacagccca caacaacttt   1260
ttctacagcc acaacccaac caaacggacc ctaaggcggc cgagcgagcg caaagcgtcg   1320
tcagctttga ttgccatgcc atctcctgct ccacttgtct ctctggccgt cgtcagccac   1380
catccaacaa ggccggtgct actggcggct cctaggtaga cgacgacgac cgacacacct   1440
ccaccgttcg ccgccgtcca ctcaccaatc aacacggaac gcccaaaaca cacacacacg   1500
cacgctgggg agggaaaaaa aggcagagac atatgcgtgc gtcgctgcat tattgtacgc    1560
gatcgaatgg catctctctc actctctctc ctcccttttat taatctggta ctggctagct    1620
ggtccggcga caccgacgtg tcagctccgt cgcgcgcgtc cgtccgtccg ctggagcgga    1680
cacggaccgc ggcgtctgtc gatcgccggc tcgccgcagc gcagctacct agcacgctca    1740
cgcatgctac actgcctaca cgcacacggc cggcccaaaa gcgttccctg ccgcctgccg    1800
gccggctttt ttattattat tggaacatga ggctatttct cctcccacac gggctacgac    1860
gtgagcacga gtactgggat cccgagatcc gccctctctg tccctgctgc tactccagcc    1920
actgaaatgt tgtcagatga aacagcagag ccgatctccg cacggaaacc catgcacggc    1980
cattcaaatt caggtgccca cgtacgtcag ggtgtttcca atactcaaaa ataacacgg    2040
tgtcaatatg gagaaaaaga aagagtaatt accaattttt tttcaattca aaaatgtaga    2100
tgtccgcagc gttattataa aatgaaagta cattttgata aaacgacaaa ttacgatccg    2160
tcgtatttat aggcgaaagc aataaacaaa ttattctaat tcggaaatct ttatttcgac    2220
gtgtctacat tcacgtccaa atgggggctt agatgagaaa cttcacgatt tggcgcgcca    2280
aagcttggtc gagtggaagc tagctttccg atcctacctg tcacttcatc aaaaggacag    2340
tagaaaagga aggtggctcc tacaaatgcc atcattgcga taaaggaaag gccatcgttg    2400
aagatgcctc tgccgacagt ggtcccaaag atggaccccc acccacgagg agcatcgtgg    2460
aaaaagaaga cgttccaacc acgtcttcaa agcaagtgga ttgatgtgat atctccactg    2520
acgtaaggga tgacgcacaa tcccactatc cttcgcaaga cccttcctct atataaggaa    2580
gttcatttca tttggagagg acacgctgac aagctgcatc tagcagatcc tctagaacca    2640
tcttccacac actcaagcca cactattgga gaacacacag ggacaacaca ccataagatc    2700
caagggaggc ctccgccgcc gcggtaacc accccgcccc tctcctcttt ctttctccgt     2760
ttttttttcc gtctcggtct cgatctttgg ccttggtagt ttgggtgggc gagaggcggc    2820
ttcgtgcgcg cccagatcgg tgcgcgggag gggcgggatc tcgcggctgg ggctctcgcc    2880
ggcgtggatc cggcccggat ctcgcgggga atgggcgtct cggatgtgaa tctgcgatcc    2940
gccgttgttg ggggagatga tggggggttt aaaatttccg ccgtgctaaa caagatcagg    3000
aagagggaa aagggcacta tggtttatat ttttatatat ttctgctgct tcgtcaggct    3060
tagatgtgct agatctttct ttcttctttt tgtgggtaga atttgaatcc ctcagcattg    3120
ttcatcggta gtttttctttt tcatgatttg tgacaaatgc agcctcgtgc ggagctttt   3180
tgtaggtaga agtgatcaac catggacaac aacccaaaca tcaacgagtg catcccgtac    3240
aactgcctca gcaaccctga ggtcgaggtg ctcggcggtg agcgcatcga gaccggttac    3300
accccccatcg acatctcccct ctccctcacg cagttcctgc tcagcgagtt cgtgccaggc    3360
gctggcttcc tcctgggcct cgtggacatc atctgggca tctttggccc ctcccagtgg    3420
gacgcctttc tggtgcaaat cgagcagctc atcaaccaga ggatcgagga gttcgccagg    3480
aaccaggcca tcagccgcct ggaggggtcc agcaacctct accaaatcta cgtcgagagc    3540
ttccgcgagt ggaggccga ccccactaac ccagctctcc gcgaggagat gcgcatccag    3600
ttcaacgaca tgaacagcgc cctgaccacc gccatcccac tcttcgccgt ccagaactac    3660
caagtcccgc tcctgtccgt gtacgtccag gccgccaacc tgcacctcag cgtgctgagg    3720
gacgtcagcg tgtttggcca gaggtggggc ttcgacgccg ccaccatcaa cagccgctac    3780
aacgacctca ccaggctgat cggcaactac accgaccacg ctgtccgctg gtacaacact    3840
```

```
ggcctggagc gcgtctgggg ccctgattct agagactgga ttcgctacaa ccagttcagg   3900
cgcgagctga ccctcaccgt cctggacatt gtgtccctct tcccgaacta cgactcccgc   3960
acctaccega tccgcaccgt gtcccaactg acccgcgaaa tctacaccaa ccccgtcctg   4020
gagaacttcg acgtagctt caggggcagc gcccagggca tcgagggctc catcaggagc   4080
ccacacctga tggacatcct caacagcatc actatctaca ccgatgccca ccgcggcgag   4140
tactactggt ccggccacca gatcatggcc tccccggtcg gcttcagcgg ccccgagttt   4200
acctttcctc tctacggcac gatgggcaac gccgctccac aacaacgcat cgtcgctcag   4260
ctgggccagg gcgtctaccg caccctgagc tccaccctgt accgcaggcc cttcaacatc   4320
ggtatcaaca accagcagct gtccgtcctg gatggcactg agttcgccta cggcacctcc   4380
tccaacctgc cctccgctgt ctaccgcaag agcggcacgg tggattccct ggacgagatc   4440
ccaccacaga acaacaatgt gccccccagg cagggttttt cccacaggct cagccacgtg   4500
tccatgttcc gctccggctt cagcaactcg tccgtgagca tcatcagagc tcctatgttc   4560
tcttggatac accgtagtgc tgagttcaac aacatcattg catccgacag cattactcaa   4620
atacccttgg tgaaagcaca tacacttcag tcaggtacta ctgttgtcag aggtccaggg   4680
tttacaggag gagacattct tcgtcgcaca agtggaggac cctttgctta cactattgtt   4740
aacatcaatg gccaattgcc ccaaaggtat cgtgcaagaa tccgctatgc ctctactaca   4800
aatctcagga tctacgtgac tgttgcaggt gaaaggatct ttgctggtca gttcaacaag   4860
actatggata ccggtgaccc tttgacattc caatctttta gctacgcaac tatcaacaca   4920
gcttttacat tcccaatgag ccagagtagc ttcacagtag gtgctgacac tttcagctca   4980
gggaatgaag tttacatcga caggtttgaa ttgattccag ttactgcaac cctcgaggct   5040
gagtacaacc ttgagagagc ccagaaggct gtgaacgccc tctttacctc caccaatcag   5100
cttggcttga aaactaacgt tactgactat cacattgacc aagtgtccaa cttggtcacc   5160
taccttagcg atgagttctg cctcgacgag aagcgtgaac tctccgagaa agttaaacac   5220
gccaagcgtc tcagcgacga gaggaatctc ttgcaagact ccaacttcaa agacatcaac   5280
aggcagccag aacgtggttg gggtggaagc accgggatca ccatccaagg aggcgacgat   5340
gtgttcaagg agaactacgt cacccctctc ggaactttcg gaagtgcta ccctacctac   5400
ttgtaccaga agatcgatga gtccaaactc aaagccttca ccaggtatca acttagaggc   5460
tacatcgaag acagccaaga ccttgaaatc tactcgatca ggtacaatgc caagcacgag   5520
accgtgaatg tcccaggtac tggttccctc tggccacttt ctgcccaatc tcccattggg   5580
aagtgtggag agcctaacag atgcgctcca caccttgagt ggaatcctga cttggactgc   5640
tcctgcaggg atggcgagaa gtgtgcccac cattctcatc acttctcctt ggacatcgat   5700
gtgggatgta ctgacctgaa tgaggacctc ggagtctggg tcatcttcaa gatcaagacc   5760
caagacggac acgcaagact tggcaacctt gagtttctcg aagagaaacc attggtcggt   5820
gaagctctcg ctcgtgtgaa gagagcagag aagagtgga gggacaaactg tgagaaactc   5880
gaatgggaaa ctaacatcgt ttacaaggag gccaaagagt ccgtggatgc tttgttcgtg   5940
aactcccaat atgatcagtt gcaagccgac accaacatcg ccatgatcca cgccgcagac   6000
aaacgtgtgc acagcattcg tgaggcttac ttgcctgagt tgtccgtgat ccctggtgtg   6060
aacgctgcca tctccgagga acttgaggga cgtatcttta ccgcattctc cttgtacgat   6120
gccagaaacg tcatcaagaa cggtgacttc aacaatgcc tcagctgctg gaatgtgaaa   6180
ggtcatgtgg acgtggagga acagaacaat cagcgttccg tcctggttgt gcctgagtgg   6240
gaagctgaag tgtcccaaga ggtagagtc tgtccaggta gaggctacat tctccgtgtg   6300
accgcttaca aggagggata cggtgagggt tgcgtgacca tccacgagat cgagaacaac   6360
accgacgagc ttaagttctc caactgcgtc gaggaagaaa tctatcccaa caacaccgtt   6420
acttgcaacg actacactgt gaatcaggaa gagtacggag gtgcctacac tagccgtaac   6480
agaggttaca acgaagctcc ttccgttcct gctgactatg cctccgtgta cgaggagaaa   6540
tcctacacag atggcagacg tgagaaccct tgcgagttca cagaggtta cagggactac   6600
acaccactc cagttggcta tgttaccaag gagcttgagt actttcctga gaccgacaaa   6660
gtgtggatcg atcggtga aaccgaggga accttcatcg tggacagcgt ggagcttctc   6720
ttgatggagg aataatgaga tctatcgatt ctagaaggcc tgaattctgc atgcgtttgg   6780
acgtatgctc attcaggttg gagccaattt ggttgatgtg tgtgcgagtt cttgcgagtc   6840
tgatgagaca tctctgtatt gtgttcttt ccccagtgtt ttctgtactt gtgtaatcag   6900
ctaatcgcca acagattcgg cgatgaataa atgagaaata aattgttctg attttgagtg   6960
caaaaaaaaa ggaattagat ctgtgtgtgt tttttggatc cccggggcgg ccgcgttaac   7020
aagcttgagc tcaggattta gcagcattcc agattgggtt caatcaacaa ggtacgagcc   7080
atatcacttt attcaaattg gtatcgccaa aaccaagaag gaactcccat cctcaaaggt   7140
ttgtaaggaa gaattctcag tccaaagcct caacaaggtc agggtacaga gtctccaaac   7200
cattagccaa aagctacagg agatcaatga agaatcttca atcaaagtaa actactgttc   7260
cagcacatgc atcatggtca gtaagtttca gaaaaagaca tccaccgaag acttaaagtt   7320
agtgggcatc tttgaaagta tcttgtcaa catcgagcag ctgccttgtg gggaccagac   7380
aaaaaaggaa tggtgcagaa ttgttaggcg cacctaccaa aagcatcttt gcctttattg   7440
caaagataaa gcagattcct ctagtacaag tggggaacaa aataacgtgg aaaagagctg   7500
tcctgacagc ccactcacta atgcgtatga cgaacgcagt gacgaccaca aaagaattcc   7560
ctctatataa gaaggcattc attcccattt gaaggatcat cagatactca accaatcctt   7620
ctaggatcta ccgtcttcgg tacgcgtca ctccgccctc tgcctttgtt actgccacgt   7680
ttctctgaat gctctcttgt gtggtgattg ctgagagtgg tttagctgga tctagaatta   7740
cactctgaaa tcgtgttctg cctgtgctga ttacttgccg tcctttgtag cagcaaaata   7800
tagggacatg gtagtacgaa acgaagatag aacctacaca gcaatacgag aaatgtgtaa   7860
tttggtgctt agcggtattt atttaagcac atgttggtgt tataggacac ttggattcga   7920
aagtttgctg ttaatttagg cacaggcttc atactacatg ggtcaatagt ataggattc   7980
atattataga cgatactata ataatttgtt cgtctgcaga gcttattatt tgccaaaatt   8040
agatattcct attctgtttt tgtttgtgtg ctgttaaatt gttaacgcct gaaggaataa   8100
atataaatga cgaatttttg atgtttatct ctgctccttt attgtgacca taagtcaaga   8160
tcagatgcac ttgtttttaaa tattgttgtc tgaagaaata agtactgaca gtattttgat   8220
gcattgatct gcttgtttgt tgtaacaaaa tttaaaaata aagagtttct tttttgttgc   8280
tctccttacc tcctgatggt atctagtatc taccaactga cactatattg cttctcttta   8340
catacgtatc ttgctcgatg cctctccct agtgttgacc agtgttactc acatagtctt   8400
tgctcatttc attgtaatgc agataccaag cggcctctag aggatcagca tggcgcccac   8460
cgtgatgatg gcctcgtcgg ccaccgccgt cgctccgttc caggggctca gtccaccgc   8520
cagcctcccc gtcgcccgcc gctcctccag aagcctcggc aacgtcagca acggcggaag   8580
```

```
gatccggtgc atgcaggtaa caaatgcatc ctagctagta gttctttgca ttgcagcagc    8640
tgcagctagc gagttagtaa taggaaggga actgatgatc catgcatgga ctgatgtgtg    8700
ttgcccatcc catcccattt cccaacccca aacgaaccaa aacacacgta ctacgtgcag    8760
gtgtggccgg cctacggcaa caagaagttc gagacgctgt cgtacctgcc gccgctgtcg    8820
accggcgggc gcatccgctg catgcaggcc atggacaact ccgtcctgca ctctggtcgc    8880
accaccatct gcgacgccta caacgtcgcg gcgcatgatc cattcagctt ccagcacaag    8940
agcctcgaca ctgttcagaa ggagtggacg gagtggaaga agaacaacca cagcctgtac    9000
ctggacccca tcgtcggcac ggtggccagc ttccttctca agaaggtcgg ctctctcgtc    9060
gggaagcgca tcctctcgga actccgcaac ctgatctttc catctggctc caccaacctc    9120
atgcaagaca tcctcaggga gaccgagaag tttctcaacc agcgcctcaa cactgatacc    9180
cttgctcgcg tcaacgctga gctgacgggt ctgcaagcaa acgtggagga gttcaaccgc    9240
caagtggaca acttcctcaa ccccaaccgc aatgcggtgc ctctgtccat cacttcttcc    9300
gtgaacacca tgcaacaact gttcctcaac cgcttgcctc agttccagat gcaaggctac    9360
cagctgctcc tgctgccact ctttgctcag gctgccaacc tgcacctctc cttcattcgt    9420
gacgtgatcc tcaacgctga cgagtggggc atctctgcag ccacgctgag gacctaccgc    9480
gactacctga agaactacac cagggactac tccaactatt gcatcaacac ctaccagtcg    9540
gccttcaagg gcctcaatac gaggcttcac gacatgctgg agttcaggac ctacatgttc    9600
ctgaacgtgt tcgagtacgt cagcatctgg tcgctcttca agtaccagag cctgctggtg    9660
tccagcggcg ccaacctcta cgccagcggc tctggtcccc aacaaactca gagcttcacc    9720
agccaggact ggccattcct gtattcgttg ttccaagtca actccaacta cgtcctcaac    9780
ggcttctctg tgctcgcct ctccaacacc ttccccaaca ttgttggcct ccccggctcc    9840
accaacaactc atgctctgct tgctgccaga gtgaactact ccggcgggcat ctcgagcggc    9900
gacattggtg catcgccgtt caaccagaac ttcaactgct ccaccttcct gccgccgctg    9960
ctcaccccgt tcgtgaggtc ctggctcgac agcggctccg accgcgaggg cgtggccacc   10020
gtcaccaact ggcaaaccga gtccttgag accacccttg gcctcggag cggcgccttc   10080
acggcgcgtg gaaattctaa ctacttcccc gactacttca tcaggaacat ctctggtgtt   10140
cctctcgtcg tccgcaacga ggacctccgc cgtccactgc actacaacga gatcaggaac   10200
atcgcctctc cgtccgggac gcccggaggt gcaagggcgt acatggtgag cgtccataac   10260
aggaagaaca acatccacgc tgtgcatgag aacggctcca tgatccacct ggcgcccaat   10320
gattacaccg gcttcaccat ctctccaatc cacgccaccc aagtgaacaa ccagacacgc   10380
accttcatct ccgagaagtt cggcaaccag ggcgactccc tgaggttcga gcagaacaac   10440
accaccgcca ggtacacctt gcgcggcaac ggcaacagct acaacctgta cctgcgcgtc   10500
agctccattg gcaactccac catcagggtc accatcaacg ggagggtgta cacagccacc   10560
aatgtgaaca cgacgaccaa caatgatggc gtcaacgaca acggcgcccg cttcagcgac   10620
atcaacattg gcaacgtggt ggccagcagc aactccgacg tcccgctgga catcaacgtg   10680
accctgaact ctggcaccca gttcgacctc atgaacatca tgctggtgcc aactaacatc   10740
tcgccgctgt actgatagga gctctgatcc ccatgggaat tccgatcgt tcaaacattt   10800
ggcaataaag tttcttaaga ttgaatcctg ttgccggtct tgcgatgatt atcatataat   10860
ttctgttgaa ttacgttaag catgtaataa ttaacatgta atgcatgacg ttatttatga   10920
gatgggtttt tatgattaga gtcccgcaat tatacattta atacgcgata gaaaacaaaa   10980
tatagcgcgc aaactaggat aaattatcgc gcgcggtgtc atctatgtta ctagatcggg   11040
gatatccccg gggcggccgc ggggaattcg gtaccaagct ttggcgcgcc aaatcgtgaa   11100
gtttctcatc taagccccca tttggacgtg aatgtagaca cgtcgaaata aagatttccg   11160
aattagaata atttgtttat tgctttcgcc tataaatacg acggatcgta atttgtcgtt   11220
ttatcaaaat gtactttcat tttataataa cgctgcggac atctacttt ttgaattgaa   11280
aaaaaattgg taattactct ttctttttct ccatattgac catcatactc attgcatccc   11340
cggaaattat gttttttaa aaaccacggt attatagata ccgtgttatt ttttgagtat   11400
tggaaatttc atttcaaccc aaagtttctt catggcacat ctagcttttg cctaataccca   11460
tgtagggcta catcttaaaa atctatacta ctatattaaa gctgcagggg tagcctgtct   11520
ccacctggtt ctgcctcgag ccaatctaaa ccgtccatct atatccatca aatcagcacc   11580
gtccggtccg tgcgcacctc ctctcccgct attcagttgc atacttgag caggttctcc   11640
ctcctcacca tttcctctgc ctcctctctc gctcactggt cagattcatc ctgcctctcc   11700
cgcatgcgct ccctccccat gcccgtctc gcactatcgc cacacctcac cgcggggaga   11760
cgaagacggt ggacgcatcc tcacctcctc cgctagttgt cgctcttcca tcctcttcaa   11820
caacttctac atagggagag gcggttcggc gtcccgaccc cgccgcttct cccctcccca   11880
tggaggacga gaacatcgac ctcggcggcg ggggcgatgc ctccgctctg catagaggag   11940
ggttgtagtg gcaagcagca atgccaacac cgaggcgggc caagactagg caacaatagg   12000
acggcacgcc cggttgtcag cgaggtggcg gcatcgtgtg ccgctaccga acaacatctc   12060
cggcgctgga gtcggtgagt tactgcgcca cccggacgcc ctcaatgcac tgatatctac   12120
ccggtctcca tcgccgccct tcctcccttc cctctccctg tgcctccctc tcttgccctc   12180
tccccttccaa ctgctcccgc cccagcccta gcccaaccag ctccgcgca gggtcaccaa   12240

SEQ ID NO: 4           moltype = DNA   length = 27
FEATURE                Location/Qualifiers
source                 1..27
                       mol_type = other DNA
                       organism = synthetic construct
SEQUENCE: 4
tttctccata ttgaccatca tactcat                                            27

SEQ ID NO: 5           moltype = DNA   length = 27
FEATURE                Location/Qualifiers
source                 1..27
                       mol_type = other DNA
                       organism = synthetic construct
SEQUENCE: 5
tttctttttc tccatattga ccatcat                                            27

SEQ ID NO: 6           moltype = DNA   length = 27
```

```
FEATURE                 Location/Qualifiers
source                  1..27
                        mol_type = other DNA
                        organism = synthetic construct
SEQUENCE: 6
tttattggct tgatagtagt agcagca                                              27

SEQ ID NO: 7            moltype = DNA  length = 27
FEATURE                 Location/Qualifiers
source                  1..27
                        mol_type = other DNA
                        organism = synthetic construct
SEQUENCE: 7
tttccaatac tcaaaaaata acacggt                                              27

SEQ ID NO: 8            moltype = DNA  length = 47
FEATURE                 Location/Qualifiers
source                  1..47
                        mol_type = other DNA
                        organism = synthetic construct
SEQUENCE: 8
gagtatgatg tttccaatac tcaaaaaata acacggtatg agtatga                        47

SEQ ID NO: 9            moltype = DNA  length = 47
FEATURE                 Location/Qualifiers
source                  1..47
                        mol_type = other DNA
                        organism = synthetic construct
SEQUENCE: 9
cgtcagggtg tttccaatac tcaaaaaata acacggtatg atggtca                        47

SEQ ID NO: 10           moltype = DNA  length = 47
FEATURE                 Location/Qualifiers
source                  1..47
                        mol_type = other DNA
                        organism = synthetic construct
SEQUENCE: 10
cgtcagggtg tttccaatac tcaaaaaata acacggtgtc aatatgg                        47

SEQ ID NO: 11           moltype = DNA  length = 1127
FEATURE                 Location/Qualifiers
source                  1..1127
                        mol_type = other DNA
                        organism = synthetic construct
SEQUENCE: 11
gaaaaaaagg cagagacata tgcgtgcgtc gctgcattat tgtacgcgat cgaatggcat          60
ctctctcact ctctctcctc cctttattaa tctggtactg gctagctggt ccggcgacac         120
cgacgtgtca gctccgtcgc gcgcgtccgt ccgtccgctg gagcggacac ggaccgcggc         180
gtctgtcgat cgccggctcg ccgcagcgca gctacctagc acgctcacgc atgctacact         240
gcctacacgc acacggccgg cccaaaagcg ttccctgccg cctgccggcc ggcttttttta        300
ttattattgg aacatgaggc tatttctcct cccacacgcg ctacgacgtg agcacgagta         360
ctgggatccc cggatccgcc ctctctgtcc ctgctgctac tccagccact gaaatgttgt         420
cagatgaaac agcagagccg atctccgcac ggaaacccat gcacggccat tcaaattcag         480
gtgcccacgt acgtcagggt gctgctgcta ctactatcaa gccaataaaa ggatggtaat         540
gagtatgatg tttccaatac tcaaaaaata acacggtatg agtatgatgg tcaatatgga         600
gaaaagaaa gagtaattac caattttttt tcaattcaaa aatgtagatg tccgcagcgt         660
tattataaaa tgaaagtaca ttttgataaa acgacaaatt acgatccgtc gtatttatag         720
gcgaaagcaa taaacaaatt attctaattc ggaaatcttt atttcgacgt gtctacattc         780
acgtccaaat gggggcttag atgagaaact tcacgattg gcgcgccaaa gcttggtcga         840
gtggaagcta gctttccgat cctacctgtc acttcatcaa aaggacagta gaaaaggaag         900
gtggctccta caaatgccat cattgcgata aaggaaaggc catcgttgaa gatgcctctg         960
ccgacagtgg tccaaagat ggaccccccac ccacgaggag catcgtggaa aaagaagacg        1020
ttccaaccac gtcttcaaag caagtggatt gatgtgtatat ctccactgac gtaagggatg        1080
acgcacaatc ccactatcct tcgcaagacc cttcctctat ataagga                      1127

SEQ ID NO: 12           moltype = DNA  length = 1402
FEATURE                 Location/Qualifiers
source                  1..1402
                        mol_type = other DNA
                        organism = synthetic construct
SEQUENCE: 12
ccggtgctac tggcggctcc taggtagacg acgacgacga cgacacctcc accgttcgcc          60
gccgtccact caccaatcaa cacggaacgc ccaaaacaca cacacgca cgctggggag         120
ggaaaaaaag gcagagacat atgcgtgcgt cgctgcatta ttgtacgcga tcgaatggca         180
tctctctcac tctctctcct cccttttatta atctggtact ggctagctgg tccggcgaca        240
ccgacgtgtc agctccgtcg cgcgcgtccg tccgtccgct ggagcggaca cggaccgcgg         300
cgtctgtcga tcgccggctc gccgcagcgc agctacctag cacgctcacg catgctacac         360
tgcctacacg cacacggccg gcccaaaagc gttccctgcc gcctgccggc cggcttttttt        420
attattattg gaacatgagg ctatttctcc tcccacacgc gctacgacgt gagcacgagt         480
```

```
actgggatcc ccggatccgc cctctctgtc cctgctgcta ctccagccac tgaaatgttg    540
tcagatgaaa cagcagagcc gatctccgca cggaaaccca tgcacggcca ttcaaattca    600
ggtgcccacg tacgtcaggg tgctgctgct actactatca agccaataaa aggatggtaa    660
tgagtatgat ggatcagcaa tgagtatgat ggtcaatatg gagaaaaaga aagagtaatt    720
accaatttt tttcaattca aaaatgtaga tgtccgcagc gttattataa aatgaaagta     780
cattttgata aaacgacaaa ttacgatccg tcgtatttat aggcgaaagc aataaacaaa    840
ttattctaat tcggaaatct ttatttcgac gtgtctacat tcacgtccaa atgggggctt    900
agatgagaaa cttcacgatt tggcgcgcca aagcttggtc gagtggaagc tagctttccg    960
atcctacctg tcacttcatc aaaaggacag tagaaaagga aggtggctcc tacaaatgcc   1020
atcattgcga taaaggaaag gccatcgttg aagatgcctc tgccgacagt ggtcccaaag   1080
atggaccccc acccacgagg agcatcgtgg aaaaagaaga cgttccaacc acgtcttcaa   1140
agcaagtgga ttgatgtgat atctccactg acgtaaggga tgacgcacaa tcccactatc   1200
cttcgcaaga cccttcctct ataaggaa gttcatttca tttggagagg acacgctgac    1260
aagctgactc tagcagatcc tctagaacca tcttccacac actcagcca cactattgga    1320
gaacacacag ggacaacaca ccataagatc caagggaggc ctccgccgcc gccggtaacc   1380
accccgcccc tctcctcttt ct                                            1402

SEQ ID NO: 13         moltype = DNA  length = 23
FEATURE               Location/Qualifiers
source                1..23
                      mol_type = other DNA
                      organism = synthetic construct
SEQUENCE: 13
caatactcaa aaataacac ggt                                              23

SEQ ID NO: 14         moltype = DNA  length = 25
FEATURE               Location/Qualifiers
source                1..25
                      mol_type = other DNA
                      organism = synthetic construct
SEQUENCE: 14
ccggtgctac tggcggctcc taggt                                           25

SEQ ID NO: 15         moltype = DNA  length = 25
FEATURE               Location/Qualifiers
source                1..25
                      mol_type = other DNA
                      organism = synthetic construct
SEQUENCE: 15
agaaagagga gagggcggg gtggt                                            25

SEQ ID NO: 16         moltype = DNA  length = 1421
FEATURE               Location/Qualifiers
source                1..1421
                      mol_type = other DNA
                      organism = synthetic construct
SEQUENCE: 16
ccggtgctac tggcggctcc taggtagacg acgacgacga cgacacctcc accgttcgcc     60
gccgtccact caccaatcaa cacggaacgc ccaaaacaca cacacacgca cgctggggag    120
ggaaaaaaag gcagagacat atgcgtgcgt cgctgcatta ttgtacgcga tcgaatggca    180
tctctctcac tctctctcct ccctttatta atctggtact ggctagctgg tccggcgaca    240
ccgacgtgtc agctccgtcg cgcgcgtccg tccgtccgct ggagcggaca cggaccgcgg    300
cgtctgtcga tcgccggctc gccgcagcgc agctaccctag cacgctcacg catgctacac    360
tgcctacacg cacacggccg gcccaaaagc gttccctgcc gctgccggc cggctttttt     420
attattattg gaacatgagg ctatttctcc tcccacacgg gctacgacgt gagcacgagt    480
actgggatcc ccggatccgc cctctctgtc cctgctgcta ctccagccac tgaaatgttg    540
tcagatgaaa cagcagagcc gatctccgca cggaaaccca tgcacggcca ttcaaattca    600
ggtgcccacg tacgtcaggg tgctgctgct actactatca agccaataaa aggatggtaa    660
tgagtatgat gttccaata ctcaaaaaat aacacggtat gatgatg tcaatatgg          720
agaaaaagaa agagtaatta ccaatttttt ttcaattcaa aatgtagat gtccgcagcg    780
ttattataaa atgaaagtac attttgataa aacgacaaat tacgatcgt cgtatttata    840
ggcgaaagca ataaacaaat tattctaatt cggaaatctt tatttcgacg tgtctacatt    900
cacgtccaaa tgggggctta gatgagaaac ttcacgattt ggcgcgccaa agcttggtcg    960
agtggaagct agctttccga tcctacctgt cacttcatca aaaggacagt agaaaaggaa   1020
ggtggctcct acaaatgcca tcattgcgat aaaggaaagg ccatcgttga agatgcctct   1080
gccgacagtg gtcccaaaga tggaccccca cccacgagga gcatcgtgga aaaagaaac   1140
gttccaacca cgtcttcaaa gcaagtggat tgatgtgata tctccactga cgtaaggat   1200
gacgcacaat cccactatcc ttcgcaagac ccttcctcta taaggaag ttcatttcat   1260
ttggagagga cacgctgaca agctgactct agcagatcct ctagaaccat cttccacaca   1320
ctcaagccac actattggag aacacacagg gacaacacac cataagatcc aagggaggcc   1380
tccgccgccg ccggtaacca ccccgcccct ctcctctttc t                       1421

SEQ ID NO: 17         moltype = DNA  length = 12301
FEATURE               Location/Qualifiers
source                1..12301
                      mol_type = other DNA
                      organism = synthetic construct
SEQUENCE: 17
aatatttaaa aatggaagta atactatatt aaaatgattc atgtggaact cctgcgcttc     60
```

```
tttttgaagt tcaaaaggg agctttcagg gtcgcttaga gtttgtttgg ttggaaatac    120
aagcgaaaag agagctaatg aggggggacat ccatattttc tatggtgttt gaataagagt    180
cacgcgggaa taagatgaac accgaaacaa ttttttttgta gctacgtggt tccaaaaaat    240
cgagtagacg gtgtcgcttc cacctcatac tacttcaacc tcaaaccaca catccttacg    300
cgcccgccgg tgtctccgtc gtctcaagtt ctcaacatac ctacacatgt aaccactacc    360
ggtctttgtc atgtttcgaa agaagattac aggtcctcta aagagagga cgcggggtgt    420
cgagaaagct ggggaagaaa aaggctagta catatgattg gtctgtgaac ctgtgaggtg    480
ggtaggtagg taggtggaga ttttttgttaa ctggtgttgt tgacggactc gaacggggcc    540
gggcgtgtgg tgtggctagc tgtggtggtt tgctcgccag ccagccagcc acacatcagc    600
gagcatgcag agcttaagca tgtatgtacg gatcggcttg cttagcggtt aagggtgtgt    660
ttggttttggc ttttggcttt ggcttttgcc ccctaaaagc caaaagccaa ccaagggtgt    720
atttggtttg acttttggct tttggctttt gtccctaaa agccaaaagc caaacaaagg    780
gttagatcta ggaagcagct ttttctaaaa gctggctttc tcacagtgca aatctgaaag    840
caccccctgaa cctgcttta gtggcttttc gaatgaaact gtgaaaacat atatcgaaga    900
acttttaacg acttttagtg gtttccacca aacagtttag cttttttaacg gcttacagcc    960
tacaacagct ttttccacag ctcacagccc acagcaactt ttttcacagc cacagcccaa   1020
ccaaacagac cccaaagggc tgaatccagg aagcagcttt ttctaaaagc cgactttctc   1080
gtagtgtaaa actgaaaaca cccctggacc tgcttttagt ggcttttgga tggaactgtg   1140
aaaacatata tcgaagaact tttaacgact tttagtggtt tccaccaaac gatttctagc   1200
tttttaacag cacacagcct acaacagctt ttttcacagc tcacagccca caacaacttt   1260
ttctacagcc acaacccaac caaacggacc ctaaggcggc cgagcgagcg caaagcgtcg   1320
tcagctttga ttgccatgcc atctcctgct ccacttgctc ctctggccgt cgtcagccac   1380
catccaacaa ggccggtgct actggcggct cctaggtaga cgacgacgac gacgacacct   1440
ccaccgttcg ccgccgtcca ctcaccaatc aacacgaaac gcccaaaaca cacacacacg   1500
cacgctgggg agggaaaaaa aggcagagac atatgcgtgc gtcgctgcat tattgtacgc   1560
gatcgaatgg catctctctc aatctctctc ctccctttat taatctggta ctggctagct   1620
ggtccggcga caccgacgtg tcagctccgt cgcgcgcgtc cgtccgtccg ctggagcgga   1680
cacggaccgc ggcgtctgtc gatcgccggc tcgccgcagc gcagctacct agcacgctca   1740
cgcatgctac actgcctaca cgcacacggc cggcccaaaa cgttccctg ccgcctgccg   1800
gccggcttttt ttattattat tggaaacatga ggctatttct cctcccacac gggctacgac   1860
gtgagcacga gtactgggat ccccggatcc gccctctctg tccctgctgc tactccagcc   1920
actgaaatgt tgtcagatga aacagcgagg ccgatctccg cacggaaacc catgcacggc   1980
cattcaaatt caggtgccca cgtacgtcag ggtgctgctg ctactactat caagccaata   2040
aaaggatggt aatgagtatg atgtttccaa tactcaaaaa ataacacggt agtagtatga   2100
tggtcaatat ggagaaaaag aaagagtaat taccaattttt ttttcaattc aaaaatgtag   2160
atgtccgcag cgttattata aaatgaaagt acatttgat aaaaacgacaa attacgatcc   2220
gtcgtattta taggcgaaag caataaacaa attattctaa ttcggaaatc tttatttcga   2280
cgtgtctaca ttcacgtcca aatgggggct tagatgagaa acttcacgat ttggcgcgcc   2340
aaagcttggt cgagtggaag ctagcttttcc gatcctacct gtcacttcat caaaaggaca   2400
gtagaaaagg aaggtggctc ctacaaatgc catcattgcg ataaaggaaa ggccatcgtt   2460
gaagatgcct ctgccgacag tggtcccaaa gatggacccc cacccacgag gagcatcgtg   2520
gaaaagaag acgttccaac cacgtcttca aagcaagtgg attgatgtga tatctccact   2580
gacgtaaggg atgacgcaca atcccactat ccttcgcaag acccttcctc tatataagga   2640
agttcatttc atttggagag gacacgctga caagctgact ctagcagatc ctctagaacc   2700
atcttccaca cactcaagcc acactattgg agaacacaca gggacaacac accataagat   2760
ccaagggagg cctccgccgc cgccggtaac caccccgccc ctctcctctt tctttctccg   2820
ttttttttttc cgtctcggtc tcgatctttg gccttggtag tttgggtggg cgagaggcgg   2880
cttcgtgcgc gcccagatcg gtgcgcggga ggggcgggat ctcgcggctg gggctctcgc   2940
cggcgtggat ccgccccgga tctcgcgggg aatgggggctc tcggatgtag atctgcgatc   3000
cgccgttgtt gggggagatg atgggggggtt taaaatttcc gccgtgctaa acaagatcag   3060
gaagagggga aaagggcact atggtttata ttttatata tttctgctgc ttcgtcaggc   3120
ttagatgtgc tagatctttc ttcttcttt ttgtgggtag aatttgaatc cctcagcatt   3180
gttcatcggt agttttttctt ttcatgattt gtgacaaatg cagcctcgtg cggagcttt    3240
ttgtaggtag aagtgatcaa ccatggacaa caacccaaac atcaacgagt gcatcccgta   3300
caactgcctc agcaaccctg aggtcgaggt gctcggcggt gagcgcatcg agaccggtta   3360
caccccccatc gacatctccc tctccctcac gcagttcctg ctcagcgagt tcgtccagg   3420
cgctggcttc gtcctgggcc tcgtggacat catctgggc atctttggcc cctcccagtg   3480
ggacgccttc ctggtgcaaa tcgagcagct catcaaccag aggatcgagg agttcgccaa   3540
gaaccaggcc atcagccgcc tggagggcct cagcaacctc taccaaatct acgctgagag   3600
cttccgcgag tgggaggccg accccactaa cccagctctc cgcgaggaga tgcgcatcca   3660
gttcaacgac atgaacagcg ccctgaccac cgccatccca ctcttcgccg tccagaacta   3720
ccaagtcccg ctcctgtccg tgtacgtcca ggccgccaac ctgcacctca gcgtgctgag   3780
ggacgtcagc gtgtttggcc agaggtgggg cttcgacgcc gccaccatca cagccgcta   3840
caacgacctc accaggctga tcggcaacta caccgaccac gctgtccgct ggtacaacac   3900
tggcctggag cgcgtctggg gccctgattc tagagactgg attcgctaca accagttcag   3960
gcgcgagctg accctcaccg tcctggacat tgtgtccctc ttcccgaact acgactcccg   4020
cacctacccg atccgcaccg tgtcccaact gacccgcgaa atctacacca ccccgtcct   4080
ggagaacttc gacggtagct tcagggggcag cgcccagggc atcgggggct ccatcaggag   4140
cccacacctg atggacatcc tcaacagcat cactatctac accgacgccc accgcggcga   4200
gtactactgg tccggccacc agatcatggc ctccccggtc ggcttcagcg gccccgagtt   4260
taccttttcct ctctacggca cgatgggcaa cgccgctcca caacaacgca tcgtcgctca   4320
gctgggccaa ggcgtctacc gcaccctgag ctccaccctg taccgcaggc ctttcaacat   4380
cggtatcaac aaccagcagc tgtccgtcct ggatggcact gagttcgcct acggcacctc   4440
ctccaactcc cctccgctg tctaccgcaa gagcggcacg gtggattccc tggacgagat   4500
cccaccacag aacaacaatg tgccccccag gcagggtttt tcccacaggc tcagccacgt   4560
gtccatgttc cgctccggct tcagcaactc gtccgtgagc atcatcagag ctcctatgtt   4620
ctcttggata caccgtagtg ctgagttcaa caacatcatt gcatccgaca gcattactca   4680
aatacccttg gtgaaagcac atacacttca gtcaggtact actgttgtca gaggtccagg   4740
gtttacagga ggagacattc ttcgtcgcac aagtggagga cccttgctt acactattgt   4800
```

```
taacatcaat ggccaattgc cccaaaggta tcgtgcaaga atccgctatg cctctactac    4860
aaatctcagg atctacgtga ctgttgcagg tgaaaggatc tttgctggtc agttcaacaa    4920
gactatggat accggtgacc cttttgacatt ccaatctttt agctacgcaa ctatcaacac    4980
agcttttaca ttcccaatga gccagagtag cttcacagta ggtgctgaca cttttcagctc   5040
agggaatgaa gttacatcg acaggtttga attgattcca gttactgcaa cctcgaggc      5100
tgagtacaac cttgagagag cccgaaggc tgtgaacgcc ctctttacct ccaccaatca     5160
gcttggcttg aaaactaacg ttactgacta tcacattgac caagtgtcca acttggtcac    5220
ctaccttagc gatgagttct gcctcgacga gaagcgtgaa ctctccgaga agttaaaca    5280
cgccaagcgt ctcagcgacg agaggaatct cttgcaagac tccaacttca aagacatcaa    5340
caggcagcca gaacgttggt ggggtggaag caccgggatc accatccaag gaggcgacga    5400
tgtgttcaag gagaactacg tcaccctctc cggaactttc gacgagtgct accctaccta    5460
cttgtaccag aagatcgatg agtccaaact caaagccttc accaggtatc aacttagagg    5520
ctacatcgaa gacagccaag accttgaaat ctactcgatc aggtacaatg ccaagcacga    5580
gaccgtgaat gtcccaggta ctggttccct ctggccactt tctgcccaat ctcccattgg    5640
gaagtgtgga gagcctaaca gatgcgctcc acaccttgag tggaatcctg acttggactg    5700
ctcctgcagg gatggcgaga gtgtgccca ccattctcat cacttctcct tggacatcga     5760
tgtgggatgt actgacctga atgaggacct cggagtctgg gtcatcttca agatcaagac    5820
ccaagacgga cacgcaagac ttggcaacct tgagtttctc gaagagaaac cattggtcgg    5880
tgaagctctc gctcgtgtga agagagcaga gaagaagtgg agggacaaac gtgagaaact    5940
cgaatgggaa actaacatcg tttacaagga ggccaaagag tccgtggatg ctttgttcgt    6000
gaactcccaa tatgatcagt gcaagccga caccaacatc gccatgatcc acgccgcaga    6060
caaacgtgtg cacagcattc gtgaggctta cttgcctgag ttgtccgtga tccctggtgt    6120
gaacgctgcc atcttcgagg aacttgaggg acgtatcttt accgcattct ccttgtacga    6180
tgccagaaac gtcatcaaga acggtgactt caacaatggc ctcagctgct ggaatgtgaa    6240
aggtcatgtg gacgtggagg aacagaacaa tcagcgttcc gtcctggttg tgcctgagtg    6300
ggaagctgaa gtgtcccaag aggttagagt ctgtccaggt agaggctaca ttctccgtgt    6360
gaccgcttac aaggagggat acggtaggg ttgcgttgacc atccacgaga tcgagaacaa    6420
caccgacgag cttaagttct ccaactgcgt cgaggaagaa atctatccca caacaccgt     6480
tacttgcaac gactacactg tgaatcagga agagtacgga ggtgcctaca ctagccgtaa    6540
cagaggttac aacgaagctc cttccgttcc tgctgactat gcctccgtgt acgaggagaa    6600
atcctacaca gatggcagac gtgagaaccc ttgcgagttc aacagaggtt acagggacta    6660
cacaccactt ccagttgget atgttaccaa ggagcttgag tacttcctg agaccgacaa      6720
agtgtggatc gagatcggtg aaaccgaggg aaccttcatc gtggacagcg tggagcttct    6780
cttgatggag gaataatgag atctatcgat tctagaaggc ctgaattctg catgcgtttg    6840
gacgtatgct cattcaggtt ggagccaatt tggttgatgt gtgtgcgagt tcttgcgagt    6900
ctgatgagac atctctgtat tgtgtttctt tccccagtgt tttctgtact tgtgtaatcg    6960
gctaatcgcc aacagattcg gcgatgaata aatgagaaat aaattgttct gatttttgagt   7020
gcaaaaaaaa aggaattaga tctgtgtgtg ttttttggat ccccgggcg gccgcgttaa     7080
caagcttgag ctcaggattt agcagcattc cagattggt tcaatcaaca aggtacgagc      7140
catatcactt tattcaaatt ggtatcgcca aaaccaagaa ggaactccca tcctcaaagg     7200
tttgtaagga agaattctca gtccaaagcc tcaacaaggt cagggtacag agtctccaaa    7260
ccattagcca aaagctacag gagatcaatg aagaatcttc aatcaaagta aactactgtt    7320
ccagcacatg catcatggtc agtaagtttc agaaaaagac atcaccgaa gacttaaagt     7380
tagtgggcat cttttgaaagt aatcttgtca acatcgagca gctggcttgt ggggaccaga    7440
caaaaaagga atggtgcaga attgttaggc gcacctacca aaagcatctt tgcctttatt    7500
gcaaagataa agcagattcc tctagtacaa gtggggaaca aaataacgtg gaaaagagct    7560
gtcctgacag cccactcact aatgcgtatg acgaaccgag tgacgaccac aaaagaattc    7620
cctctatata agaaggcatt cattcccatt tgaaggatca tcagatactc aaccaatcct    7680
tctaggatct accgtcttcg gtacgcgctc actccgccct ctgcctttgt tactgccacg     7740
tttctctgaa tgctctcttg tgtggtgatt gctgagagtg gtttagctgg atctagaatt     7800
acactctgaa atcgtgttct gcctgtgctg attacttgcc gtccttttgta gcagcaaaat    7860
atagggacat ggtagtacga aacgaagata gaacctacac agcaatacga gaaatgtgta    7920
atttggtgct tagcggtatt tatttaagca catgttggtg ttataggca cttggattca     7980
gaagtttgct gttaatttag gcacaggctt catactacat gggtcaatag tatagggatt   8040
catattatag gcgatactat aataatttgt tcgtctgcag agcttattat ttgccaaaat    8100
tagatattcc tattctgttt ttgtttgtgt gctgttaaat tgttaacgcc tgaaggaata    8160
aatataaatg acgaaatttt gatgtttatc tctgctcctt tattgtgacc ataagtcaag    8220
atcagatgca cttgttttaa atattgttgt ctgaagaaat aagtactgac agtattttga    8280
tgcattgatc tgcttgtttg ttgtaacaaa atttaaaaat aaagagttc cttttttgttg     8340
ctctccttac ctcctgatgg tatctagtat ctaccaactg acactatatt gcttctcttt     8400
acatacgtat cttgctcgat gccttctccc tagtgttgac cagtgttact cacatagtct    8460
ttgctcattt cattgtaatg cagataccaa gcggcctcta gaggatcagc atggcgccca    8520
ccgtgatgat ggcctcgtcg gccaccgccg tcgctccgtt caggggctc aagtccaccg     8580
ccagcctccc cgtcgcccgc cgctcctcca aagcctcgc caacgccgaa    8640
ggatccggtg catgcaggta acaaatgcat cctagctagt agttctttgc attgcagcag    8700
ctgcagctag cgagttagta ataggaaggg aactgatgat ccatgcatgg actgatgtgt    8760
gttgccatc ccatcccatt tcccaacccc aaacgaacca aaacacacgt actacgtgca    8820
ggtgtggccg gcctacggca acaagaagtt cgagacgctc tcgtacctgc cgccgctgtc    8880
gaccggcgc cgcatccgc catgcaggc catggacaa tccgtcctga actctggtga        8940
caccaccatc tgcgacgcct acaacgtcgc ggcgcatgat ccattcagct tccagcacaa    9000
gagcctcgac actgttcaga aggagtggac ggagtgaag aagaacaacc acagcctgta     9060
cctgaccccc atcgtcggca cggtggccag cttccttctc aagaaggtcg gctctctcgt    9120
cgggaagcgc atcctctcgg aactccgcaa cctgatcttt ccatctggct ccaccaacct    9180
catgcaagac atccctcaggg agaccgagaa gttttctcaac cagccgtcca acactgatac  9240
ccttgctcgc gtcaacgctg agctgacggg tctgcaagca aacgtggagg agttcaaccg    9300
ccaagtggac aacttcctca accccaaccg caatgcggtg cctctgtcca tcacttcttc    9360
cgtgaacacc atgcaacaac tgttcctcaa ccgcttgcct cagttccaga tgcaggcta     9420
ccagctgctc ctgctgccac tctttgctca ggctgccaac ctgcacctct ccttcattcg    9480
tgacgtgatc ctcaacgctg acgagtgggg catctctgca gccacgctga ggacctaccg    9540
```

```
cgactacctg aagaactaca ccagggacta ctccaactat tgcatcaaca cctaccagtc   9600
ggccttcaag ggcctcaata cgaggcttca cgacatgctg gagttcagga cctacatgtt   9660
cctgaacgtg ttcgagtacg tcagcatctg gtcgctcttc aagtaccaga gcctgctggt   9720
gtccagcggc gccaacctct acgccagcgg ctctggtccc caacaaactc agagcttcac   9780
cagccaggac tggccattcc tgtattcgtt gttccaagtc aactccaact acgtcctcaa   9840
cggcttctct ggtgctcgcc tctccaacac cttccccaac attgttggcc tccccggctc   9900
caccacaact catgctctgc ttgctgccag agtgaactac tccggcggca ctcgagcgg    9960
cgacattggt gcatcgccgt tcaaccagaa cttcaactgc tccaccttcc tgccgccgct  10020
gctcaccccg ttcgtgaggt cctggctcga cagcggctcc gaccgcgagg gcgtggccac  10080
cgtcaccaac tggcaaaccg agtccttcga gaccaccctt ggcctccgga gcgggcgcct  10140
cacggcgcgt ggaaattcta actcttccc cgactacttc atcaggaaca tctctggtgt   10200
tcctctcgtc gtccgcaacg aggacctccg ccgtccactg cactacaacg agatcaggaa  10260
catcgcctct ccgtccggga cgcccggagg tgcaagggcg tacatggtga cgtcccaata  10320
caggaagaac aacatccacg ctgtgcatga gaacgctcc atgatccacc tggcgcccaa  10380
tgattacacc ggcttcacca tctctccaat ccacgccacc caagtgaaca accagacacg  10440
cacccttcatc tccgagaagt tcggcaacca gggcgactcc ctgaggttcg agcagaacaa  10500
caccaccgcc aggtacaccc tgcgcggcaa cggcaacagc tacaacctgt acctgcgcgt  10560
cagctccatt ggcaactcca ccatcagggt caccatcaac gggagggtgt acacagccaa  10620
caatgtgaac acgacgacca caatgatggt cgtcaacgac aacggcgccc gcttcagcga  10680
catcaacatt ggcaacgtgg tggccagcag caactccgac gtcccgctgg acatcaacgt  10740
gaccctgaac tctggcaccc agttcgacct catgaacatc atgctggtgc aactaacat   10800
ctcgccgctg tactgatagg agctctgatc cccatggtcc tcccgatcg ttcaaacatt  10860
tggcaataaa gtttcttaag attgaatcct gttgccggtc ttgcgatgat tatcatataa  10920
tttctgttga attacgttaa gcatgtaata attaacatgt aatgcatgac gttatttatg  10980
agatgggttt tatgattag agtcccgcaa ttatacattt aatacgcgat agaaaacaaa   11040
atatagcgcg caaactagga taaattatcg cgcgcggtgt catctatgtt actagatcgg  11100
ggatatcccc ggggcggccg cggggaattc ggtaccaagc tttggcgcgc caaatcgtga  11160
agtttctcat ctaagcccc atttggacgt gaatgtagac acgtcgaaat aaagatttcc  11220
gaattagaat aatttgttta ttgctttcgc ctataaatac gacggatcgt aatttgtcgt  11280
tttatcaaaa tgtactttca tttataata acgctgcgga catctacatt tttgaattga  11340
aaaaaaattg gtaattactc ttttctttttc tccatattga ccatcatact cattgcatcc  11400
ccggaaatta tgttttttta aaaccacgg tattatagat accgtgttat ttttgagta   11460
ttggaaattt catttcaacc caaagttct tcatggcaca tctagctttt gcctaatacc  11520
atgtagggct acatcttaaa aatctatact actatattaa agctgcaggg gtagcctgtc  11580
tccacctggt tctgcctcga gccaatcaa accgtccatc tatatccatc aaatcagcac  11640
cgtccggtcc gtgcgcacct cctctcccgc tattcagttg catacttgca gcaggttctc  11700
cctcctcacc atttcctctg cctcctctct cgctcactgg tcagattcat cctgcctctc  11760
ccgcatgcgc tccctcccca tgcccgtct cgcactacg ccacacctca ccgcggggag  11820
acgaagacgg tggacgcatc ctcacctcct cgctagttg tcgctcttcc atcctcttca  11880
acaacttcta cataggggaga ggcggttcgg cgtcccgacg ccgccgcttc tcccctcccc  11940
atggaggacg agaacatcga cctcggcggc gggggcgatg cctccgctct gcatagagga  12000
gggttgtagt ggcaagcagc aatgccaaca ccgaggcggg ccaagactag caacaatag   12060
gacggcacgc ccggttgtca gcgaggtggc ggcacatcgt gccgctaccg aacaactct   12120
ccggcgctgg agtcggtgag ttactgcgcc acccggacgc cctcaatgca ctgatatcta  12180
cccggtctcc atcgccgccc ttcctccctt ccctctccct gtgcctccct ctcttgccct  12240
ctcccttcca actgctcccg ccccagccct agcccaacca cctcccgcgc agggtcacca  12300
a                                                                  12301

SEQ ID NO: 18          moltype = AA  length = 1307
FEATURE                Location/Qualifiers
source                 1..1307
                       mol_type = protein
                       organism = unidentified
SEQUENCE: 18
MTQFEGFTNL YQVSKTLRFE LIPQGKTLKH IQEQGFIEED KARNDHYKEL KPIIDRIYKT    60
YADQCLQLVQ LDWENLSAAI DSYRKEKTEE TRNALIEEQA TYRNAIHDYF IGRTDNLTDA   120
INKRHAEIYK GLFKAELFNG KVLKQLGTVT TTEHENALLR SFDKFTTYFS GFYENRKNVF   180
SAEDISTAIP HRIVQDNFPK FKENCHIFTR LITAVPSLRE HFENVKKAIG IFVSTSIEEV   240
FSFPFYNQLL TQTQIDLYNQ LLGGISREAG TEKIKGLNEV LNLAIQKNDE TAHIIASLPH   300
RFIPLFKQIL SDRNTLSFIL EEFKSDEEVI QSFCKYKTLL RNENVLETAE ALFNELNSID   360
LTHIFISHKK LETISSALCD HWDTLRNALY ERRISELTGK ITKSAKEKVQ RSLKHEDINL   420
QEIISAAGKE LSEAFKQKTS EILSHAHAAL DQPLPTTLKK QEEKEILKSQ LDSLLGLYHL   480
LDWFAVDESN EVDPEFSARL TGIKLEMEPS LSFYNKARNY ATKKPYSVEK FKLNFQMPTL   540
ASGWDVNKEK NNGAILFVKN GLYYLGIMPK QKGRYKALSF EPTEKTSEGF DKMYYDYFPD   600
AAKMIPKCST QLKAVTAHFQ THTTPILLSN NFIEPLEITK EIYDLNNPEK EPKKFQTAYA   660
KKTGDQKGYR EALCKWIDFT RDFLSKYTKT TSIDLSSLRP SSQYKDLGEY YAELNPLLYH   720
ISFQRIAEKE IMDAVETGKL YLFQIYNKDF AKGHHGKPNL HTLYWTGLFS PENLAKTSIK   780
LNGQAELFYR PKSRMKRMAH RLGEKMLNKK LKDQKTPIPD TLYQELYDYV NHRLSHDLSD   840
EARALLPNVI TKEVSHEIIK DRRFTSDKFF FHVPITLNYQ AANSPSKFNQ RVNAYLKEHP   900
ETPIIGIDRG ERNLIYITVI DSTGKILEQR SLNTIQQFDY QKKLDNREKE RVAARQAWSV   960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN                1307

SEQ ID NO: 19          moltype = DNA  length = 41
FEATURE                Location/Qualifiers
```

|  |  |  |
|---|---|---|
| source | 1..41<br>mol_type = other DNA<br>organism = synthetic construct | |
| SEQUENCE: 19 | | |
| aaaggatggt aatgagtatg atggatcagc aatgagtatg a | | 41 |

| SEQ ID NO: 20 | moltype = DNA   length = 2061 |  |
|---|---|---|
| FEATURE | Location/Qualifiers | |
| source | 1..2061<br>mol_type = other DNA<br>organism = synthetic construct | |
| SEQUENCE: 20 | | |
| aatatttaaa aatggaagta atactatatt aaaatgattc atgtggaact cctgcgcttc | | 60 |
| tttttgaagt ttcaaaaggg agctttcagg gtcgcttaga gtttgtttgg ttggaaatac | | 120 |
| aagcgaaaag agagctaatg agggggacat ccatatttc tatggtgttt gaataagagt | | 180 |
| cacgcgggaa taagatgaac accgaaacaa tttttttgta gctacgtggt tccaaaaaat | | 240 |
| cgagtagacg gtgtcgcttc cacctcatac tacttcaacc tcaaaccaca catccttacg | | 300 |
| cgcccgccgg tgtctccgtc gtctcaagtt ctcaacatac ctacacatgt aaccactacc | | 360 |
| ggtctttgtc atgtttcgaa agaagattac aggtcctcta aagagagga cgcggggtgg | | 420 |
| cgagaaagct ggggaagaaa aaggctagta catatgattg gtctgtgaac ctgtgaggtg | | 480 |
| ggtaggtagg taggtggaga ttttgttaa ctggtgttgt tgacggactc gaacggggcc | | 540 |
| gggcgtgtgg tgtggctagc tgtggtggtt tgctcgccag ccagccagcc acacatcagc | | 600 |
| gagcatgcag agcttaagca tgtatgtacg gatcggcttg cttagcggtt aagggtgtgt | | 660 |
| ttggttttggc ttttggcttt ggcttttgcc ccctaaaagc caaaagccaa ccaagggtgt | | 720 |
| atttggtttg acttttggct tttggctttt gtccctaaaa agccaaaagc caaacaaagg | | 780 |
| gttagatcta ggaagcagct ttttctaaaa gctggcttc tcacagtgca aatctgaaag | | 840 |
| caccctgaa cctgcttta gtggcttttc gaatggaact gtgaaaacat atatcgaaga | | 900 |
| actttaacg acttttagtg gtttccacca aacagtttag cttttaacg gcttacagcc | | 960 |
| tacaacagct ttttccacag ctcacagccc acagcaactt ttttcacagc cacagcccaa | | 1020 |
| ccaaacagac cccaaagggc tgaatccagg aagcagcttt ttctaaaagc cgactttctc | | 1080 |
| gtagtgtaaa actgaaaaca cccctggacc tgcttttagt ggcttttgga tggaactgtg | | 1140 |
| aaaacatata tcgaagaact tttaacgact tttagtggtt ccaccaaac gatttctagc | | 1200 |
| ttttttaacag cacacagcct acaacagctt ttttcacagc tcacagccca caacaacttt | | 1260 |
| ttctacagcc acaacccaac caaacggacc ctaaggcggc cgagcgagcg caaagcgtca | | 1320 |
| tcagctttga ttgccatgcc atctcctgct ccacttgtct ctctggccgt cgtcagccac | | 1380 |
| catccaacaa ggccggtgct actggcggct cctaggtaga cgacgacgac gacgaccct | | 1440 |
| ccaccgttcg ccgccgtcca ctcaccaatc aacacggaac gccaaaaaca cacacacacg | | 1500 |
| cacgctgggg agggaaaaaa aggcagagac atatgcgtgt gtcgctgcat tattcgtacg | | 1560 |
| gatcgaatgg catctctctc actctctctc ctccctttat taatctggta ctggctagct | | 1620 |
| ggtccggcga caccgacgtg tcagctccgg cgcgcgcgtc cgtccgtccg ctggagcgga | | 1680 |
| cacggaccgc ggcgtctgtc gatcgccggc tcgccgcagc gcagctacct agcacgctca | | 1740 |
| cgcatgctac actgcctaca cgcacacggc cggcccaaaa gcgttccctg ccgcctgccg | | 1800 |
| gccggcttt ttattattat tggaacatga ggctatttct cctcccacac gggctacgac | | 1860 |
| gtgagcacga gtactgggat ccccggatcc gccctctctg tccctgctgc tactccagcc | | 1920 |
| actgaaaatgt tgtcagatga aacagcagag ccgatcccg cacggaaacc catgcacggc | | 1980 |
| cattcaaatt caggtgccca cgtacgtcag ggtgctgctg ctactactat caagccaata | | 2040 |
| aaaggatggt aatgagtatg a | | 2061 |

| SEQ ID NO: 21 | moltype = DNA   length = 40 |  |
|---|---|---|
| FEATURE | Location/Qualifiers | |
| source | 1..40<br>mol_type = other DNA<br>organism = synthetic construct | |
| SEQUENCE: 21 | | |
| tgaccatcat actcattgca tccccggaaa ttatgttttt | | 40 |

| SEQ ID NO: 22 | moltype = DNA   length = 904 |  |
|---|---|---|
| FEATURE | Location/Qualifiers | |
| source | 1..904<br>mol_type = other DNA<br>organism = synthetic construct | |
| SEQUENCE: 22 | | |
| tccccggaaa ttatgttttt ttaaaaacca cggtattata gataccgtgt tattttttga | | 60 |
| gtattggaaa tttcatttca acccaaagtt tcttcatggc acatctagct tttgcctaat | | 120 |
| accatgtagg gctacatctt aaaaatctat actactatat taaagctgca ggggtagcct | | 180 |
| gtctccacct ggttctgcct cgagccaatc taaaccgtcc atctatatcc atcaaatcag | | 240 |
| caccgtccgg tccgtgcgca cctcctctcc cgctattcag ttgcatactt gcagcaggtt | | 300 |
| ctccctcctc accatttcct ctgcctcctc tctcgctcac tggtcagatt catcctgctc | | 360 |
| ctcccgcatg cgctccctcc ccatgccccg tctcgcacta tcgccacacc tcaccgcggg | | 420 |
| gagacgaaga cggtggacgc atcctcacct cctccgctag ttgtcgctct tccatcctct | | 480 |
| tcaacaactt ctacataggg agaggcggtt cggcgtcccg acgccgccgc ttctcccctc | | 540 |
| cccatggagg acgagaacat cgacctcggc ggcgggggcg atgcctccgc tctgcataga | | 600 |
| ggagggttgt agtggcaagc agcaatgcca acaccgaggc gggccaagac taggcaacaa | | 660 |
| taggacggca cgcccggttg tcagcgaggt gggcagcatcg tgtgccgcta caaacaca | | 720 |
| tctccgcgcg tggagtcggt gagttactgc gccaccggga cgcccgtcaat gcactgatat | | 780 |
| ctacccggtc tccatcgccg cccttcctcc ctttccctctc cctgtgcctc cctctcttgc | | 840 |
| cctctccctt ccaactgctc ccgccccagc cctagcccaa ccacctcccg cgcagggtca | | 900 |
| ccaa | | 904 |

```
SEQ ID NO: 23          moltype = DNA  length = 12246
FEATURE                Location/Qualifiers
source                 1..12246
                       mol_type = other DNA
                       organism = synthetic construct
SEQUENCE: 23
aatatttaaa aatggaagta atactatatt aaaatgattc atgtggaact cctgcgcttc   60
tttttgaagt ttcaaaaggg agctttcagg gtcgcttaga gtttgtttgg ttggaaatac  120
aagcgaaaag agagctaatg aggggacat ccatattttc tatggtgttt gaataagagt   180
cacgcgggaa taagatgaac accgaaacaa tttttttgta gctacgtggt tccaaaaaat  240
cgagtagacg tgtcgcttc cacctcatac tacttcaacc tcaaaccaca catccttacg   300
cgcccgccgg tgtctccgtc gtctcaagtt ctcaacatac ctacacatgt aaccactacc  360
ggtctttgtc atgtttcgaa agaagattac aggtcctcta gaagagagga cgcggggtgg  420
cgagaaagct ggggaagaaa aaggctagta catatgatgt gtctgtgaac ctgtgaggtg  480
ggtaggtagg taggtggaga tttttgttaa ctggtgttgt tgacggactc gaacggggcc  540
gggcgtgtgg tgtggctagc tgtggtggtt tgctcgccag ccagccagcc acacatcagc  600
gagcatgcag agcttaagca tgtatgtacg gatcggcttg cttagcggtt aagggtgtgt  660
ttggtttggc ttttggcttt ggcttttgcc ccctaaaagc caaaagccaa ccaagggtgt  720
atttggtttg acttttggct tttgcttttt gtccctaaa agccaaaagc caaacaaagg   780
gttagatcta ggaagcagct ttttctaaaa gctggctttc tcacagtgca aatctgaaag  840
cacccctgaa cctgctttta gtggcttttc gaatggaact gtgaaaacat atatcgaaga  900
acttttaacg acttttagtg gtttccacca aacagtttag ctttttaacg gcttacagcc  960
tacaacagct ttttcacag ctcacagccc acagcaactt ttttcacagc cacagcccaa   1020
ccaaacagac cccaaagggc tgaatccagg aagcagcttt ttctaaaagc cgactttctc  1080
gtagtgtaaa actgaaaaca cccctggacc tgcttttagt ggcttttgga tggaactgtg  1140
aaaacatata tcgaagaact tttaacgact tttagtgtt tccaccaaac gatttctagc   1200
ttttttaacag cacacagcct acaacagctt ttttcacagt tcacagccca caacaacttt  1260
ttctacagcc acacccaac caaacggacc ctaaggcggc cgagcgagcg caaagcgtcg   1320
tcagctttga ttgccatgcc atctcctgct ccacttgtct ctctgccgt cgtcagccac   1380
catccaacaa ggccggtgct actggcgcgt cctaggtaga cgacgacgac gacgacacct  1440
ccaccgttcg ccgccgtcca ctcaccaatc aacacgaaac gcccaaaaca cacacacacg  1500
cacgctgggg agggaaaaaa aggcagagac atatgcgtgc gtcgctgcat tattgtacgc  1560
gatcgaatgc atctctctc actctctctc ctccctttat taatctggta ctggctagct   1620
ggtccggcga caccgacgtg tcagtccgt cgcgcgcgtc cgtccgtccg ctggagcgga   1680
cacggaccgc ggcgtctgtc gatcgccggc tcgccgcagc tcagctacct agcacgctca  1740
cgcatgctac actgcctaca cgcacacggc cggcccaaaa gcgttccctg ccgcctgccg  1800
gccggctttt ttattattat tggaacatga ggctatttct cctcccacac gggctacgac  1860
gtgagcacga gtactgggat ccccggatcc gccctctctg tccctgctgc tactccagcc  1920
actgaaatgt tgtcagatga aacagcagag ccgatctccg cacggaaacc catgcacggc  1980
cattcaaatt caggtgccca cgtacgtcag ggtgtttcca atactcaaaa ataacacgg   2040
tatgatggtc aatatggaga aaagaaaga gtaattacca attttttttc aattcaaaaa  2100
tgtagatgtc cgcagcgtta ttataaatg aaagtacatt ttgataaaac gacaaattac   2160
gatccgtcgt atttataggc gaaagcaata aacaaattat tctaattcgg aaatctttat  2220
ttcgacgtgt ctacattcac gtccaaatgg gggcttagat gagaaacttc acgatttggc  2280
gcgccaaagc ttggtcgagt ggaagctagc tttccgatcc tacctgtcac ttcatcaaaa  2340
ggacagtaga aaaggaaggt ggctcctaca aatgccatca ttgcgataaa ggaaaggcca  2400
tcgttgaaga tgcctctgcc gacagtggtc ccaaagatgg accccaccc acgaggagca   2460
tcgtggaaaa agaagacgtt ccaaccacgt cttcaaagca agtggattga tgtgatatct  2520
ccactgacgt aagggatgac gcacaatccc actatccttc gcaagaccct tcctctatat  2580
aaggaagttc atttcatttg gagaggacac gctgacaagc tgactctagc agatcctcta  2640
gaaccatctt ccacacactc aagccacact atttggagaac acacagggac acacacacat   2700
aagatccaag ggaggcctcc gccgccgcg gtaaccaccc cgcccctctc ctctttcttt   2760
ctccgttttt ttttccgtct cggtctcgat ctttggcctt ggtagtttgg gtgggcgaga  2820
ggcggcttcg tgcgcgccca gatcggtgcg cgggagggg gggatctcgc ggctggggct   2880
ctcgccggcg tggatccggc ccggatctcg cggggaatgg gctctcgga tgtagatctg   2940
cgatccgccg ttgttggggg agatgatggg gggtttaaaa tttccgccgt gctaaacaag  3000
atcaggaaga ggggaaaagg gcactatggt ttatattttt atatatttct gctgcttcgt   3060
caggcttaga tgtgctagat ctttctttct tcttttgtg ggtagaattt gaatccctca   3120
gcattgttca tcggtagttt ttctttcat gatttgtgac aaatgcagcc tcgtgcggag  3180
ctttttttgta ggtagaagtg atcaaccatg gacaacaacc caaacatcaa cgagtgcatc  3240
ccgtacaact gcctcagcaa ccctgaggtc gaggtgctcg gcggtgagcg catcgagacc  3300
ggttacaccc ccatcgacat ctccctctcc tcacgcagt tcctgctcag cgagttcgtg  3360
ccaggcgctg gcttcgtcct gggctcgtg gacatcatct ggggcatctt tggcccctcc  3420
cagtggacga ccttcctggt gcaaatcgag cagctcatca accagaggat cggagagttc  3480
gccaggaacc aggccatcag ccgcctggag ggcctcagca acctctacca aatctacgct  3540
gagagcttcc gcgagtggga ggcgacccc actaacccag ctctccgcga ggagatgcgc  3600
atccagttca acgacatgaa cagcgccctg accaccgcca tccctctctt cgccgtccag  3660
aactaccaag tccgctcct gtccgtgtac gtccaggccg ccaacctgca cctcagcgtg   3720
ctgagggacg tcagcgtgtt tggccagagg tgggggcttcg acgccgccac catcaacagc  3780
cgctacaacg acctcaccag gctgatcggc aactacaccg accacgctgt ccgctggtac  3840
aacactggcc tggagcgcgt ctggggccct gattctagag actggattcg ctacaaccag  3900
ttcaggcgcg agctgaccct caccgtcctg gacattgtgt cctcttccc gaactacgac  3960
tcccgcacct acccgatccg caccgtgtcc caactgaccc gcgaaatcta caccaacccc  4020
gtcctggaga acttcgacgg tagcttcagg ggcagcgcca agggcatcga gggctccatc  4080
aggagcccac acctgatgga catcctcaac agcatcacta tctacaccga tgcccaccgc  4140
ggcgagtact actggtccgg ccaccagatc atggcctccc cggtcggctt cagcggcccc  4200
gagtttacct ttcctctcta cggcacgatg ggcaacgccg ctccacaaca acgcatcgtc  4260
gctcagctgg gccaggggcgt ctaccgcacc ctgagctcca cctgtaccg caggcccttc  4320
aacatcggta tcaacaacca gcagctgtcc gtcctggatg gcactgagtt cgcctacggc  4380
```

```
acctcctcca aacctgccctc cgctgtctac cgcaagagcg gcacggtgga ttccctggac    4440
gagatcccac cacagaacaa caatgtgccc cccaggcagg gttttcccca caggctcagc    4500
cacgtgtcca tgttccgctc cggcttcagc aactcgtccg tgagcatcat cagagctcct    4560
atgttctctt ggatacaccg tagtgctgag ttcaacaaca tcattgcatc cgacagcatt    4620
actcaaatac ccttggtgaa agcacataca cttcagtcag gtactactgt tgtcagaggt    4680
ccagggttta caggaggaga cattcttcgt cgcacaagtg gaggacccct tgccttacact   4740
attgttaaca tcaatggcca attgcccaaa aggtatcgtg caagaatccg ctatgcctct    4800
actacaaatc tcaggatcta cgtgactgtt gcaggtgaaa ggatctttgc tggtcagttc    4860
aacaagacta tggataccgg tgacccttg acattccaat cttttagcta cgcaactatc     4920
aacacagctt ttacattccc aatgagccag agtagcttca cagtaggtgc tgacactttc    4980
agctcaggga atgaagttta catcgacagg tttgaattga ttccagttac tgcaaccctc    5040
gaggctgagt acaaccttga gagagcccag aaggctgtga acgccctctt tacctccacc    5100
aatcagcttg gcttgaaaac taacgttact gactatcaca ttgaccaagt gtccaacttg    5160
gtcacctacc ttagcgatga gttctgcctc gacgagaagc gtgaactctc cgagaaagtt    5220
aaacacgcca agcgtctcag cgacgagagg aatctcttgc aagactccaa cttcaaagac    5280
atcaacaggc agccagaacg tggttgggt ggaagcaccg ggatcaccat ccaaggaggc     5340
gacgatgtgt tcaaggagaa ctacgtcacc ctctccggaa ctttcgacga gtgctaccct    5400
acctacttgt accagaagat cgatgagtcc aaactcaaag cctcaccag gtatcaactt     5460
agaggctaca tcgaagacag ccaagacctt gaaatctact cgatcaggta caatgccaag    5520
cacgagaccg tgaatgtccc aggtactggt tccctctggc cactttctgc ccaatctccc    5580
attgggaagt gtggagagcc taacagatgc gctccacacc ttgagtggaa tcctgacttg    5640
gactgctcct gcagggatgg cgagaagtgt gcccaccatt ctcatcactt ctccttggac    5700
atcgatgtgg gatgtactga cctgaatgag gacctcggag tctgggtcat cttcaagatc    5760
aagacccaag acggacacgc aagacttggc aaccttgagt ttctcgaaga gaaaccattg    5820
gtcggtgaag ctctcgctcg tgtgaagaga gcagagaaga agtggaggga caaacgtgag    5880
aaactcgaat gggaaactaa catcgtttac aaggaggcca aagatccgt ggatgcttg     5940
ttcgtgaact cccaatatga tcagttgcaa gccgacacca acatcgccat gatccacgcc    6000
gcagacaaac gtgtgcacag cattcgtgag gcttacttgc ctgagttgtc cgtgatccct    6060
ggtgtgaacg ctgccatctt cgaggaactt gagggacgta tctttaccgc attctccttg    6120
tacgatgcca gaaacgtcat caagaacggt gacttcaaca atggcctcag ctgctggaat    6180
gtgaaaggtc atgtggacgt ggaggaacag aacaatcagc gttccgtcct ggttgtgcct    6240
gagtgggaag ctgaagtgtc ccaagaggtt agagtctgtc caggtagagg ctacattctc    6300
cgtgtgaccg cttacaagga gggatacggt gagggttgcg tgaccatcca cgagatcgag    6360
aacaacaccg acgagcttaa gttctccaac tgcgtcgagg aagaaatcta tcccaacaac    6420
accgttactt gcaacgacta cactgtgaat caggaagagt acggaggtgc ctacactagc    6480
cgtaacagag gttacaacga agctccttcc gttcctgctg actatgcctc cgtgtacgag    6540
gagaaatcct acacagatgg cagacgtgag aaccccttgcg agttcaacag aggttacagg    6600
gactacacac cacttccagt tggctatgtt accaaggagc ttgagtactt tcctgagacc    6660
gacaaagtgt ggatcgagat cggtgaaacc gagggaacct tcatcgtgga cagcgtggag    6720
cttctcttga tggaggaata atgagatcta tcgattctag aaggcctgaa ttctgcatgc    6780
gtttggacgt atgctcattc aggttggagc caatttggtt gatgtgtgtg cgagttcttg    6840
cgagtctgat gagacatctc tgtattgtgt ttcttttccc agtgttttct gtacttgtgt    6900
aatcgcctaa tcgccaacag attcggcgat gaataaatga gaataaatt gttctgattt    6960
tgagtgcaaa aaaaaaggaa ttagatctgt gtgtgttttt tggatcccgg ggcggccgc    7020
gttaacaagc ttgagctcag gatttagcag cattccagat tggggtcaat caacaaggta    7080
cgagccatat cactttattc aaaattggtat cgccaaaacc aagaaggaac tcccatcctc    7140
aaaggtttgt aaggaagaat tctcagtcca aagcctcaac aaggtcaggg tacagagtct    7200
ccaaaccatt agccaaaagc tacaggagat caatgaagaa tcttcaatca agtaaaacta    7260
ctgttccagc acatgcatca tggtcagtaa gtttcagaaa aagacatcca ccgaagactt    7320
aaagttagtg gcatctttg aaagtaatct tgtcaacatc gagcagctgg cttgtgggga    7380
ccagacaaaaa aaggaatggt gcagaattgt taggcgcacc taccaaaagc atctttgcct   7440
ttattgcaaa gataaagcag attcctctag tacaagtggg gaacaaaata acgtggaaaa    7500
gagctgtcct gacagcccac tcactaatgc gtatgacgaa cgcagtacg accacaaaag     7560
aattccctct atataagaag gcattcattc ccatttgaag gatcatcaga tactcaacca    7620
atccttctag gatctaccgt cttcggtacg cgctcactcc gccctctgcc tttgttactg    7680
ccacgttttct ctgaatgctc tcttgtgtgg tgattgctga gagtggttta gctggatcta   7740
gaattacact ctgaaatcgt gttctgcctg tgctgattac ttgccgtcct ttgtagcagc    7800
aaaatatagg gacatggtag tacgaaacga agatagaacc tacacagcaa tacgagaaat    7860
gtgtaatttg gtgcttagcg gtatttattt aagcacatgt tggtgttata gggcacttgg    7920
attcagaagt ttgctgttaa tttaggcaca ggcttcatac tacatgggtc aatagtatag    7980
ggattcatat tataggcgat actataataa tttgttcgtc tgcagagctt attatttgcc    8040
aaaattagat attcctattc tgtttttgtt tgtgtgctgt taaattgtta acgcctgaag    8100
gaataaatat aaatgacgaa atttgatgt ttatctctgc tcctttattg tgaccataag    8160
tcaagatcag atgcacttgt tttaaatatt gttgtctgaa gaataagta ctgacagtat    8220
tttgatgcat tgatctgctt gtttgttgta acaaaattta aaaataaaga gtttccttt    8280
tgttgctctc cttacctcct gatggtatct agtatctacc aactgacact atattgcttc    8340
tctttacata cgtatcttgc tcgatgcctt ctccctagtg ttgaccagtg ttactcacat    8400
agtctttgct catttcattg taatgcagat accaagcggc ctctagagaa tcagcatggc    8460
gccaccgtg atgatggcct cgtcggccac cgccgtcgct ccgttccagg cgctcaagtc    8520
caccgccagc ctccccgtcg cccgccgctc ctccagaagc ctcggcaacg tcagcaacgg    8580
cggaaggatc cggtgcatgc aggtaacaaa tgcatcctag ctagtagttc tttgcattgc    8640
agcagctgca gctagcgagt tagtaatagg aagggaactg atgatccatg catggactga    8700
tgtgtgttgc ccatcccatc ccatttccca accccaaacg aaccaaaaca cacgtactac    8760
gtgcaggtgt ggccggccta cggcaacaag aagttcgaga cgctgtcgta cctgccgccg    8820
ctgtcgaccg gcgggcgcat ccgctgcatg caggccatgg acaactccgt cctgaactct    8880
ggtcgcacca ccatctgcga cgcctacaac gtcgcggcgc atgatccatt cagcttccag    8940
cacaagagcc tcgacactgt tcagaaggag tggacggagt ggaagaagaa caaccacagc    9000
ctgtacctgg accccatcgt cggcacggtg gccagcttcc ttctcaagaa ggtcggctct    9060
ctcgtcggga agcgcatcct ctcggaactc cgcaacctga tctttccatc tggctccacc    9120
```

```
aacctcatgc aagacatcct cagggagacc gagaagtttc tcaaccagcg cctcaacact   9180
gataccettg ctcgcgtcaa cgctgagctg acgggtctgc aagcaaacgt ggaggagttc   9240
aaccgccaag tggacaactt cctcaaccce aaccgcaatg cggtgcctct gtccatcact   9300
tcttccgtga acaccatgca acaactgttc ctcaaccgct tgcctcagtt ccagatgcaa   9360
ggctaccagc tgctcctgct gccactcttt gctcaggctg ccaacctgca cctctccttc   9420
attcgtgacg tgatcctcaa cgctgacgag tggggcatct ctgcagccac gctgaggacc   9480
taccgcgact acctgaagaa ctacaccagg gactactcca actattgcat caacacctac   9540
cagtcggcct tcagggcct caatacgagg cttcacgaca tgctggagtt caggacctac    9600
atgttcctga acgtgttcga gtacgtcagc atctggtcgc tcttcaagta ccagagcctg   9660
ctggtgtcca gcggcgccaa cctctacgcc agcggctctg gtccccaaca aactcagagc   9720
ttcaccagcc aggactggcc attcctgtat tcgttgttcc aagtcaactc caactacgtc   9780
ctcaacggct tctctggtgc tcgcctctcc aacaccttcc ccaacattgt tggcctcccc   9840
ggctccacca caactcatgc tctgcttgct gccagagtga actactccgg cggcatctcg   9900
agcggcgaca ttggtgcatc gccgttcaac cagaacttca actgctccac cttcctgcca  9960
ccgctgctca cccegttcgt gaggtcctgg ctcgacagcg gctccgaccg cgagggcgtg  10020
gccaccgtca ccaactggca aaccgagtcc ttcgagacca cccttggcct ccggagcggc  10080
gccttcacgg cgcgtggaaa ttctaactac ttccccgact acttcatcag gaacatctct  10140
ggtgttcctc tcgtcgtccg caacgaggac ctccgccgtc cactgcacta caacgagatc  10200
aggaacatcg cctctccgtc cgggacgccc ggaggtgcaa gggcgtacat ggtgagcgtc  10260
cataacagga agaacaacat ccacgctgtg catgagaacg gctccatgat ccacctggcg  10320
cccaatgatt acaccggctt caccatctct ccaatccacg ccacccaagt gaacaaccag  10380
acacgcacct tcatctccga gaagttcggc aaccagggcg actccctgag gttcgagcag  10440
aacaacacca ccgccaggta caccctgcgc ggcaacggca acagctacaa cctgtacctg  10500
cgcgtcagct ccattggcaa ctccaccatc agggtcacca tcaacgggag ggtgtacaca  10560
gccaccaatg tgaacacgac gaccaacaat gatggcgtca acgacaacgg cgcccgcttc  10620
agcgcatca acattggcaa cgtggtggcc agcagcaacc ccgacgtccc gctggacatc  10680
aacgtgaccc tgaactctgg cacccagttc gacctcatga acatcatgct ggtgccaact  10740
aacatctcgc cgctgtactg ataggagctc tgatccccat gggaattccc gatcgttcaa  10800
acatttggca ataaagtttc ttaagattga atcctgttgc cggtcttgcg atgattatca  10860
tataatttct gttgaattac gttaagcatg taataattaa catgtaatgc atgacgttat  10920
ttatgagatg ggtttttatg attagagtcc cgcaattata catttaatac gcgatagaaa  10980
acaaaatata gcgcgcaaac taggataaat tatcgcgcgc ggtgtcatct atgttactag  11040
atcgggata tccccggggc ggccgcgggg aattcggtac caagctttgg cgcgccaaat   11100
cgtgaagttt ctcatctaag cccccatttg gacgtgaatg tagacacgtc gaaataaaga  11160
tttccgaatt agaataattt gtttattgct ttcgcctata aatacgacgg atcgtaattt  11220
gtcgttttat caaaatgtac tttcattta taataacgct gcggacatct acattttga   11280
attgaaaaaa aattggtaat tactcttct ttttctccat attgaccatc atactcattg   11340
catcccegga aattatgttt ttttaaaaac cacggtatta tagatacegt gttattttt   11400
gagtattgga aatttcattt caacccaaag tttcttcattg gcacatctag tctttgccta  11460
ataccatgta gggctacatc ttaaaaatct atactactat attaaagctg caggggtage  11520
ctgtctccac ctggttctgc ctcgagccaa tctaaaccgt ccatctatat ccatcaaatc  11580
agcaccgtcc ggtcgtgcg caccctctct ccgctattc agttgcatac ttgcagcagg    11640
ttctccetcc tcaccatttc ctctgcctcc tctctcgctc actggtcaga ttcatcctgc  11700
ctctcccgca tgcgctccct cccatgccc cgtctcgcac tatcgccaca cctcaccgcc   11760
gggagacgaa gacggtggac gcatcctcac ctcctccgct agttgtcgct cttccatcct  11820
cttcaacaac ttctacatag ggagaggcgg ttcggcgtcc cgacgccgcc gcttctcccc  11880
tcccatgga ggacgagaac atcgacctcg gcggcgggcg cgatgcctcc gctctgcata   11940
gaggagggtt gtagtggcaa gcagcaatgc caacaccgag gcgggccaag actaggcaac  12000
aataggacgg cacgccggt tgtcagcgag gtggcggcat cgtgtgccgc taccgaacaa   12060
catctccggc gctggagtcg gtgagttact gcgccaccg gacgccctca atgcactgat   12120
atctaccegg tctccatcgc cgccttcct ccctccctc tccctgtgcc tccctctctt    12180
gccctctccc ttccaactgc tcccgcccca gcctagccc aaccacctcc cgcgcaggt    12240
caccaa                                                              12246

SEQ ID NO: 24         moltype = DNA  length = 1071
FEATURE               Location/Qualifiers
source                1..1071
                      mol_type = other DNA
                      organism = synthetic construct
SEQUENCE: 24
gaaaaaaagg cagagacata tgcgtgcgtc gctgcattat tgtacgcgat cgaatggcat     60
ctctctcact ctctctcctc cctttattaa tctggtactg gctagctggt ccggcgacac    120
cgacgtgtca gctccgtcgc gcgcgtccgt ccgtccgctg gagcggacac ggaccgcggc   180
gtctgtcgat cgccggctcg ccgcagcgca gctacctagc acgctcacgc atgctacact   240
gcctacacgc acacgccggg cccaaaagcg ttccctgccg cctgccggcc ggcttttta   300
ttattattgg aacatgaggc tatttctcct cccacacggg ctacgacgtg agcacgagta   360
ctgggatccc cggatccgcc ctctctgtcc ctgctgctac tccagccact gaaatgttgt   420
cagatgaaac agcagagccg atctccgcac ggaaaccat gcacggccat tcaaattcag   480
gtgcccacgt acgtcagggt gtttccaata ctcaaaaaat aacacggtat gatggtcaat   540
atggagaaaa agaaagagta attaccaatt ttttttcaat tcaaaaatgt agatgtccgc   600
agcgttatta taaatgaaa gtacattttg ataaaacgac aaattacgat ccgtcgtatt    660
tataggcgaa agcaataaac aaattattct aattcggaaa tctttattc gacgtgtcta    720
cattcacgtc caaatggggg cttagatgag aaacttcacg atttggcgcg ccaaagcttg   780
gtcgagtgga agctagcttt ccgatcctac ctgtcacttc atcaaaagga cagtagaaaa   840
ggaaggtggc tcctacaaat gccatcattg cgataaagga aaggccatcg ttgaagatgc   900
ctctgccgac agtggtccca agatggacc ccacccacg aggagcatcg tggaaaaaga    960
agacgttcca accacgtctt caagcaagt ggattgatgt gatatctcca ctgacgtaag   1020
ggatgacgca caatcccact atccttcgca agacccttcc tctatataag g           1071
```

| SEQ ID NO: 25 | moltype = DNA  length = 1066 |
| --- | --- |
| FEATURE | Location/Qualifiers |
| source | 1..1066 |
| | mol_type = other DNA |
| | organism = synthetic construct |

SEQUENCE: 25

```
gaaaaaaagg cagagacata tgcgtgcgtc gctgcattat tgtacgcgat cgaatggcat   60
ctctctcact ctctctcctc cctttattaa tctggtactg gctagctggt ccggcgacac  120
cgacgtgtca gctccgtcgc gcgcgtccgt ccgtccgctg gagcggacac ggaccgcggc  180
gtctgtcgat cgccggctcg ccgcagcgca gctacctagc acgctcacgc atgctacact  240
gcctacacgc acacggccgg cccaaaagcg ttccctgccg cctgccggcc ggcttttttta  300
ttattattgg aacatgaggc tatttctcct cccacacggg ctacgacgtg agcacgagta  360
ctgggatccc cggatccgcc ctctctgtcc ctgctgctac tccagccact gaaatgttgt  420
cagatgaaac agcagagccg atctccgcac ggaaacccat gcacggccat tcaaattcag  480
gtgcccacgt acgtcagggt gtttccaata ctcaaaaaat aacacggtgt caatatggag  540
aaaaagaaag agtaattacc aatttttttt caattcaaaa atgtagatgt ccgcagcgtt  600
attataaaat gaaagtacat tttgataaaa cgacaaatta cgatccgtcg tatttatagg  660
cgaaagcaat aaacaaatta ttctaattcg gaaatcttta tttcgacgtg tctacattca  720
cgtccaaatg ggggcttaga tgagaaactt cacgatttgg cgcgccaaag cttggtcgag  780
tggaagctag ctttccgatc ctacctgtca cttcatcaaa aggacagtag aaaaggaagg  840
tggctcctac aaatgccatc attgcgataa aggaaaggcc atcgttgaag atgcctctgc  900
cgacagtggt cccaaagatg gaccccccacc cacgaggagc atcgtggaaa aagaagacgt  960
tccaaccacg tcttcaaagc aagtggattg atgtgatatc tccactgacg taagggatga  1020
cgcacaatcc cactatcctt cgcaagaccc ttcctctata taagga              1066
```

| SEQ ID NO: 26 | moltype = DNA  length = 12219 |
| --- | --- |
| FEATURE | Location/Qualifiers |
| source | 1..12219 |
| | mol_type = other DNA |
| | organism = synthetic construct |

SEQUENCE: 26

```
aatatttaaa aatggaagta atactatatt aaaatgattc atgtggaact cctgcgcttc   60
tttttgaagt ttcaaaaggg agctttcagg gtcgcttaga gtttgtttgg ttggaaatac  120
aagcgaaaag agagctaatg agggggacat ccatatttc tatggtgttt gaataagagt  180
cacgcgggaa taagatgaac accgaaacaa ttttttttgta gctacgtggt tccaaaaaat  240
cgagtagacg tgtcgcttc cacctctatac tacttcaacc tcaaaccaca catccttacg  300
cgcccgccgg tgtctccgtc gtctcaagtt ctcaacatac ctacacatgt aaccactacc  360
ggtctttgtc atgtttcgaa agaagattac aggtcctcta gaagagagga cgcggggtgg  420
cgagaaagct ggggaagaaa aaggctagta catatgatgg gtctgtgaac ctgtgaggtg  480
ggtaggtagg taggtggaga ttttttgttaa ctggtgttgt tgacggactc gaacggggcc  540
gggcgtgtgg tgtggctagc tgtggtggtt tgctcgccag ccagccagcc acacatcagc  600
gagcatgcag agcttaagca tgtatgtacg gatcggcttg cttagcggtt aagggtgtgt  660
ttggtttgag ttttggcttt ggcttttgcc ccctaaaagc caaaagccaa ccaagggtgt  720
atttggtttg acttttggct tttgcttttt gtccctaaa agccaaaagc caaacaaagg  780
gttagatcta ggaagcagct ttttctaaaa gctggctttc tcacagtgca aatctgaaag  840
cacccctgaa cctgctttta gtggcttttc gaatggaact gtgaaaacat atatcgaaga  900
acttttaacg acttttagtg gtttccacca aacagtttag cttttaacg gcttacagcc  960
tacaacagct ttttcacag ctcacagccc acagcaactt ttttcacagc cacagcccaa 1020
ccaaacagac cccaaagggc tgaatccagg aagcagcttt ttctaaaagc cgactttctc 1080
gtagtgtaaa actgaaaaca cccctggacc tgcttttagt ggcttttgga tggaactgtg 1140
aaaacatata tcgaagaact tttaacgact tttagtggtt tccaccaaac gatttctgaa 1200
ttttttaacag cacacagcct acaacagctt ttttcacagc tcacagccca caacaacttt 1260
ttctacagcc acacccaac caaacggacc ctaaggcggc cgagcgagcg caaagcgtcg 1320
tcagctttga ttgccatgcc atctcctgct ccacttgtct ctctggccgt cgtcagccac 1380
catccaacaa ggccggtgct actggcgcgct cctaggtaga cgacgacgac gacgacacct 1440
ccaccgttcg ccgccgtcca ctcaccaatc aacacggaac gcccaaaaca cacacacacg 1500
cacgctgggg agggaaaaaa aggcagagac atatgcgtgc gtcgctgcat tatttgtacgc 1560
gatcgaatgc catctctctc actctctctc ctcccttat taatctggta ctggctagct 1620
ggtccggcga caccgacgtg tcagctccgt cgcgcgcgtc cgtccgtccg ctggagcgga 1680
cacggaccgc ggcgtctgtc gatcgccggc tcgccgcagc gcagctacct agcacgctca 1740
cgcatgctac actgcctaca cgcacacggc cggcccaaaa gcgttccctg ccgcctgccg 1800
gccggctttt ttattattat tggaacatga ggctatttct cctcccacac gggctacgac 1860
gtgagcacga gtactgggat ccccggatcc gccctctctg tccctgctgc tactccagcc 1920
actgaaatgt tgtcagatga aacagcagag ccgatctccg cacggaaacc catgcacggc 1980
cattcaaatt caggtgccca cgtacgtcag ggtgatgatg tcaatatgg agaaaaagaa 2040
agagtaatta ccaatttttt ttcaattcaa aatgtagat gtccgcagcg ttattataaa 2100
atgaaagtac attttgataa aacgacaaat tacgatccgt cgtatttata ggcgaaagca 2160
ataaacaaat tattctaatt cggaaatctt tatttcgacg tgtctacatt cacgtccaaa 2220
tgggggctta gatgagaaac ttcacgattt ggcgcgccaa agcttggtcg agtggaagct 2280
agctttccga tcctacctgt cacttcatca aaaggacagt agaaaaggaa ggtggctcct 2340
acaaatgcca tcattgcgat aaaggaaagg ccatcgttga agatgcctct gccgacagtg 2400
gtcccaaaga tggaccccca cccacgagga gcatcgtgga aaaagaagac gttccaacca 2460
cgtcttcaaa gcaagtggat tgatgtgata tctccactga cgtaagggat gacgcacaat 2520
cccactatcc ttcgcaagac ccttcctcta taaggaagg ttcatttcat ttggagagga 2580
cacgctgaca agctgactct agcagatcct ctagaaccat cttccacaca ctcaagccac 2640
actattggag aacacacagg acaaacacac cataagatcc aagggaggcc tccgccgccg 2700
ccggtaacca ccccgcccct ctcctctttc tttctccgtt tttttttccg tctcggtctc 2760
gatctttggc cttggtagtt tgggtgggcg agaggcggct tcgtgcgcgc ccagatcggt 2820
gcgcgggagg ggcgggatct cgcggctggg gctctcgccg gcgtgatcc ggcccggatc 2880
```

```
tcgcggggaa tggggctctc ggatgtagat ctgcgatccg ccgttgttgg gggagatgat   2940
gggggggttta aaatttccgc cgtgctaaac aagatcagga agaggggaaa agggcactat   3000
ggtttatatt tttatatatt tctgctgctt cgtcaggctt agatgtgcta gatctttctt   3060
tcttcttttt gtgggtagaa tttgaatccc tcagcattgt tcatcggtag tttttctttt   3120
catgatttgt gacaaatgca gcctcgtgcg gagcttttt gtaggtagaa gtgatcaacc    3180
atggacaaca acccaaacat caacgagtgc atcccgtaca actgcctcag caaccctgag   3240
gtcgaggtgc tcggcggtga gcgcatcgag accggttaca cccccatcga catctccctc   3300
tccctcacgc agttcctgct cagcgagttc gtgccaggcg ctggcttcgt cctgggcctc   3360
gtggacatca tctggggcat cttttggcccc tcccagtggg acgcctttcct ggtgcaaatc  3420
gagcagctca tcaaccagag gatcgaggag ttcgccaaga accaggccat cagccgcctg   3480
gagggcctca gcaacctcta ccaaatctac gctgagagct tccgcgagtg ggaggccgac   3540
cccactaacc cagctctccg cgaggagatg cgcatccagt tcaacgacat gaacagcgcc   3600
ctgaccaccg ccatcccact cttcgccgtc cagaactacc aagtcccgct cctgtccgtg   3660
tacgtccagg ccgccaacct gcacctcagc gtgctgaggg acgtcagcgt gtttggccag   3720
aggtggggct tcgacgccgc caccatcaac agccgctaca acgacctcac caggctgatc   3780
ggcaactaca ccgaccacgc tgtccgctgg tacaacactg gcctggagcg cgtctggggc   3840
cctgattcta gagactggat tcgctacaac cagttcaggc gcgagctgac cctcaccgtc   3900
ctggacattg tgtccctctt cccgaactac gactcccgca cctacccgat cgcaccgtg    3960
tcccaactga cccgcgaaat ctacaccaac cccgtcctgg agaacttcga cggtagcttc   4020
agggcagcg cccagggcat cgagggctcc atcaggagcc cacacctgat ggacatcctc    4080
aacagcatca ctatctacac cgatgcccac cgcgcgagt actactggtc cggccaccag   4140
atcatggcct ccccggtcgg cttcagcggc cccgagttta cctttcctct ctacggcacg   4200
atgggcaacg ccgctccaca caacgcatc gtcgctcagc tgggcaggg cgtctaccg    4260
accctgagct ccaccctgta ccgcaggccc ttcaacatcg gtatcaacaa ccagcagctg   4320
tccgtcctgg atggcactga gttcgcctac ggcacctcct ccaacctgcc ctccgctgtc   4380
taccgcaaga gcggcacggt ggattccctg gacgagatcc caccacagaa caacaatgtg   4440
ccccccaggc agggttttttc ccacaggctc agccacgtgt ccatgttccg ctccggcttc   4500
agcaactcgt ccgtgagcat catcagagct cctatgttct cttggataca ccgtagtgct   4560
gagttcaaca acatcattgc atccgacagc attactcaaa tacccttggt gaaagcacat   4620
acacttcagt caggtactac tgttgtcaga ggtccagggt ttacaggagg agacattctt   4680
cgtcgcacaa gtggaggacc ctttgcttac actattgtta acatcaatgg ccaattgccc   4740
caaaggtatc gtgcaagaat ccgctatgcc tctactacaa atctcaggat ctacgtgact   4800
gttgcaggtg aaaggatctt tgctggtcag ttcaacaaga ctatggatac cggtgaccct   4860
ttgacattcc aatcttttag ctacgcaact atcaacacag cttttacatt cccaatgagc   4920
cagagtagct tcacagtagg tgctgacact ttcagctcag gaatgaagt ttacatcgac    4980
aggtttgaat tgattccagt tactgcaacc ctcgaggctg agtacaacct tgagagagcc   5040
cagaaggctg tgaacgccct ctttacctcc accaatcagc ttggcttgaa aactaacgtt   5100
actgactatc acattgacca agtgtccaac ttggtcacct accttagcga tgagttctgc   5160
ctcgacgaga agcgtgaact ctccgagaaa gttaaacacg ccaagcgtct cagcgacgag   5220
aggaatctct tgcaagactc caacttcaaa gacatcaaca ggcagccaga acgtggttgg   5280
ggtggaagca ccgggatcac catccaagga ggcgacgatg tgttcaagga gaactacgtc   5340
accctctccg gaactttcga cgagtgctac cctacctact tgtaccagaa gatcgatgag   5400
tccaaactca aagccttcac caggtatcaa cttagaggct acatcgaaga cagccaagac   5460
cttgaaatct actcgatcag gtacaatgcc aagcacgaca ccgtgaatgt cccaggtact   5520
ggttccctct ggccactttc tgcccaatct cccattggga agtgtggaga gcctaacaga   5580
tgcgctccac accttgagtg gaatcctgac ttggactgct cctgcaggga tggcgagaag   5640
tgtgccacc atttctcatca cttctccttg gacatcgatg tgggatgtac tgacctgaat    5700
gaggaccctcg gagtctgggt catcttcaag atcaagaccc aagacggaca cgcaagactt   5760
ggcaaccttg agtttctcga agagaaacca ttggtcggtg aagctctcgc tcgtgtgaag   5820
agagcagaga agaagtggag ggacaaacgt gagaaactcg aatgggaaac taacatcgtt   5880
tacaaggagg ccaagagtc cgtggagtct ttgttcgtga actcccaata tgatcagttg     5940
caagccgaca ccaacatcgc catgatccac gccgcagaca aacgtgtgca cagcattcgt   6000
gaggcttact tgcctgagtt gtccgtgatc cctggtgtga acgctgccat cttcgaggaa   6060
cttgagggac gtatctttac cgcattctcc ttgtacgatg ccagaaacgt catcaagaac   6120
ggtgacttca acaatggcct cagctgctgg aatgtgaaag gtcatgtgga cgtggaggaa   6180
cagaacaatc agcgttccgt cctggttgtg cctgagtgg aagctgaagt gtcccaagag     6240
gttagagtct gtccaggtag aggctacatt ctccgtgtga ccgcttacaa ggagggatac   6300
ggtgagggt gcgtgaccat ccacgagatc gagaacaaca ccgacgagct taagttctcc    6360
aactgcgtcg aggaagaaat ctatcccaac aacaccgtta cttgcaacga ctacacgtg    6420
aatcaggaag agtacggagg tgcctacact agccgtaaca gaggttacaa cgaagctcct   6480
tccgttcctg ctgactatgc ctccgtgtac gaggagaaat cctacacaga tggcagacgt   6540
gagaacccctt gcgagttcaa cagaggttac agggactaca caccacttcc agttggctat   6600
gttaccaagg agcttgagta ctttcctgag accgacaaag tgtggatcga gatcggtgaa   6660
accgagggaa ccttcatcgt ggacagcgtg gagcttctct tgatggagga ataatgaggat  6720
ctatcgattc tagaaggcct gaattctgca tgcgtttgga cgtatgctca ttcaggttgg   6780
agccaattg gttgatgtgt gtgcgagttc ttgcgagtct gatgagacat ctctgtattg     6840
tgtttctttc cccagtgttt tctgtacttg tgtaatcggc taatcgccaa cagattcggc   6900
gatgaataaa tgagaaataa attgttctga tttgagtgc aaaaaaaaag gaattagatc     6960
tgtgtgtgtt ttttggatcc ccggggcggc cgcgttaaca agcttgagct caggatttag   7020
cagcattcca gattgggttc aatcaacaag gtacgagcca tcactttta ttcaaattgg    7080
tatcgccaaa accaagaagg aactcccatc ctcaaaggtt tgtaaggaag aattctcagt   7140
ccaaagcctc aacaaggtca gggtacagag tctccaaacc attagccaaa agctacagga   7200
gatcaatgaa gaatcttcaa tcaaagtaaa ctactgttcc agcacatgca tcatggtcag   7260
taagtttcag aaaaagacat ccaccgaaga cttaagtta gtggtgcatct ttgaaagtaa   7320
tcttgtcaac atcgagcagc tggcttgtgg ggaccagaca aaaaaggaat ggtgcagaat   7380
tgttaggcgc acctaccaaa agcatctttg cctttattgc aaagataaag cagattcctc   7440
tagtacaagt ggggaacaaa ataacgtgga aaagagctgt cctgacagcc cactcactaa   7500
tgcgtatgac gaacgcagtg acgaccacaa aagaattccc tctatataag aaggcattca   7560
ttcccatttg aaggatcatc agatactcaa ccaatccttc taggatctac cgtcttcggt   7620
```

```
acgcgctcac tccgccctct gcctttgtta ctgccacgtt tctctgaatg ctctcttgtg   7680
tggtgattgc tgagagtggt ttagctggat ctagaattac actctgaaat cgtgttctgc   7740
ctgtgctgat tacttgccgt cctttgtagc agcaaaatat agggacatgg tagtacgaaa   7800
cgaagataga acctacacag caatacgaga aatgtgtaat ttggtgctta gcggtattta   7860
tttaagcaca tgttggtgtt atagggcact tggattcaga agtttgctgt taatttaggc   7920
acaggcttca tactcatggg gtcaatagta tagggattca tattataggc gatactataa   7980
taatttgttc gtctgcagag cttattattt gccaaaatta gatattccta ttctgttttt   8040
gtttgtgtgc tgttaaattg ttaacgcctg aaggaataaa tataaatgac gaaatttga    8100
tgtttatctc tgctccttta ttgtgaccat aagtcaagat cagatgcact tgttttaaat   8160
attgttgtct gaagaaataa gtactgacag tattttgatg cattgatctg cttgtttgtt   8220
gtaacaaaat ttaaaaataa agagtttcct ttttgttgct ctccttacct cctgatggta   8280
tctagtatct accaactgac actatattgc ttctctttac atacgtatct tgctcgatgc   8340
cttctcccta gtgttgacca gtgttactca catagtcttt gctcatttca ttgtaatgca   8400
gataccaagc ggctctaga ggatcagcat ggcgcccacc gtgatgatgg cctcgtcggc    8460
caccgccgtc gctccgttcc aggggctcaa gtccaccgcc agcctcccg tcgcccgccg    8520
ctcctccaga agcctcggca acgtcagcaa cggcggaagg atccggtgca tgcaggtaac   8580
aaatgcatcc tagctagtag ttctttgcat tgcagcagct gcagctagcg agttagtaat   8640
aggaagggaa ctgatgatcc atgcatggac tgatgtgtgt tgcccatccc atcccattc    8700
ccaaccccaa acgaaccaaa acacacgtac tacgtgcagg tgtggccggc ctacggcaac   8760
aagaagttcg agacgctgtc gtacctgccg ccgctgtcga ccggcgggcg catccgctgc   8820
atgcaggcca tggacaactc cgtcctgaac tctggtcgca ccaccatctg cgacgcctac   8880
aacgtcggcg cgcatgatcc attcagcttc cagcacaaga gcctcgacac tgttcagaag   8940
gagtggacgg agtggaagaa gaacaaccac agcctgtacc tggacccat cgtcggcacg    9000
gtggccagct tccttctcaa gaaggtcggc tctctcgtcg ggaagcgcat cctctcggaa    9060
ctccgcaacc tgatctttcc atctggctcc accaacctca tgcaagacat cctcaggag    9120
accgaaagt ttctcaacca gcgcctcaac actgatccc ttgctcgcgt caacgctgga     9180
ctgacgggtc tgcaagcaaa cgtggaggag ttcaaccgcc aagtggacaa cttcctcaac   9240
cccaaccgca atgcggtgcc tctgtccatc acttcttccg tgaacaccat gcaacaactg   9300
ttcctcaacc gcttgcctca gttccagatg caaggctacc agctgctcct gctgccactc   9360
tttgctcagg ctgccaacct gcacctctcc ttcattcgtc acgtgatcct caacgctgac   9420
gagtggggca tctctgcagc cacgctgagg acctacgcg actacctgaa gaactacacc    9480
agggactact ccaactattg catcaacacc taccagtcgg ccttcaaggg cctcaatacg   9540
aggcttcacg acatgctgga gttcaggacc tacatgttcc tgaacgtgtt cgagtacgtc   9600
agcatctggt cgctcttcaa gtaccagagc ctgctggtgt ccagcggcgc caacctctac   9660
gccagcggct ctggtcccca acaaactcag agcttcacca gccaggactg gccattcctg   9720
tattcgttgt tccaagtcaa ctccaactac gtcctcaacg gcttctctgg tgctcgcctc   9780
tccaacacct tccccaacat tgttggcctc cccggctcca ccacaactca tgctctgctt   9840
gctgccagag tgaactactc cggcggcatc tcgagcggcg acattggtgc atcgccgttc   9900
aaccagaact tcaactgctc caccttcctg ccgccgccgc tcaccccgtt cgtgaggtcc   9960
tggctcgaca gcggctccga ccgcgagggc gtggccaccg tcaccaactg gcaaaccgag  10020
tccttcgaga ccaccttgg cctcggagc ggcgccttca cggcgcgtgg aaattctaac    10080
tacttccccg actacttcat caggaacatc tctggtgttc ctctcgtcgt ccgcaacgag  10140
gacctcgcc gtccactgca ctacaacgag atcaggacca tcgcctctcc gtccgggacg    10200
cccggaggtg caaggcgta catggtgagc gtccataaca ggaagaacaa catccacgct    10260
gtgcatgaga acggctccat gatccacctg cgcccaatg attacaccgg cttcaccatc    10320
tctccaatcc acgccaccca agtgaacaac cagacacgca ccttcatctc cgagaagttc  10380
ggcaaccagg gcgactccct gaggttcgag cagaacaaca ccaccgccag gtacaccctg  10440
cgcggcaacg gcaacagcta caacctgtac ctgcgcgtca gctccattgg caactccacc  10500
atcagggtca ccatcaacgg gagggtgtac acagccacca atgtgaacac gacgaccaac  10560
aatgatggcg tcaacgacaa cggcgcccgc ttcagcgaca tcaacattgg caacgtggtg  10620
gccagcagca actccgacgt cccgcagcga atcaacgtga ccctgaactc tggcacccag  10680
ttcgacctca tgaacatcat gctggtgcca actaacatct cgccgctgta ctgataggag  10740
ctctgatccc catgggaatt cccgatcgtt caaacatttg gcaataaagt ttcttaagat  10800
tgaatcctgt tgccggtctt gcgatgatta tcatataatt tctgttgaat tacgttaagc  10860
atgtaataat taacatgtaa tgcatgacgt tatttatgag atgggttttt atgattagag  10920
tcccgcaatt atacatttaa tacgcgatag aaaacaaaat atagcgcgca aactaggata  10980
aattatcgcg cgcggtgtca tctatgttac tagatcgggg atatcccgg gcggccgcg   11040
gggaattcgg taccaagctt tggcgcgcca aatcgtgaag tttctcatct aagcccccat  11100
ttggacgtga agtagacac gtcgaaataa agatttccga attagaataa tttgttttatt  11160
gctttcgcct ataaatacga cggatcgtaa tttgtcgttt tatcaaaatg tactttcatt  11220
ttataataac gctgcggaca tctacatttt tgaattgaaa aaaaattggt aattactctt  11280
tcttttttctc catattgacc atcatactca ttgcatcccc ggaaattatg ttttttaaa   11340
aaccacggta ttatagatac cgtgtttattt tttgagtatt ggaaatttca tttcaaccca  11400
aagtttcttc atggcacatc tagcttttgc ctaataccat gtagggctac atcttaaaaa  11460
tctatactac tatattaaag ctgcaggggt agcctgtctc cacctggttc tgcctcgagc  11520
caatctaaac cgtccatcta tatccatcaa atcagcaccg tccggtccgt gcgcacctcc  11580
tctcccgcta ttcagttgca tacttgcagc aggttctccc tcctcaccat ttcctctgcc  11640
tcctctctcg ctcactggtc agattcatcc tgcctctccc gcatcgcgtc cctcccatg   11700
ccccgtctcg cactatcgcc acacctcacc gcggggagac gaagacggtg gacgcatcct  11760
cacctcctcc gctagttgtc gctcttccat cctcttcaac aacttctaca tagggagagg  11820
cggttcggcg tccgacgcc gccgcttctc ccctccccat ggaggacgag aacatcgacc    11880
tcggcggcg gggcgatgcc tccgctctgc atagaggagg gttgtagtgg caagcagcaa  11940
tgccaacacc gaggcgggcc aagactaggc aacaatagga cggcacgccc ggttgtcagc  12000
gaggtggcg catcgtgtgc cgctaccgaa caacatctcc ggcgctggag tcggtgagtt   12060
actgcgccac ccggacgccc tcaatgcact gatatctacc cggtctccat cgccgccctt  12120
cctcccttcc ctctccctgt gcctcccctct cttgccctct cccttccaac tgctcccgcc  12180
ccagccctag cccaaccacc tccgcgcagg ggtcaccaa                          12219

SEQ ID NO: 27        moltype = DNA   length = 12213
```

```
FEATURE                Location/Qualifiers
source                 1..12213
                       mol_type = other DNA
                       organism = synthetic construct
SEQUENCE: 27
aatatttaaa aatggaagta atactatatt aaaatgattc atgtggaact cctgcgcttc    60
tttttgaagt ttcaaaaggg agctttcagg gtcgcttaga gtttgtttgg ttggaaatac   120
aagcgaaaag agagctaatg aggggggacat ccatattttc tatggtgttt gaataagagt  180
cacgcgggaa taagatgaac accgaaacaa ttttttttgta gctacgtggt tccaaaaaat  240
cgagtagacg gtgtcgcttc cacctcatca tacttcaacc tcaaaccaca catccttacg   300
cgcccgccgg tgtctccgtc gtctcaagtt ctcaacatac ctacacatgt aaccactacc   360
ggtctttgtc atgtttcgaa agaagattac aggtcctcta aagagagga cgcggggtgg    420
cgagaaagct ggggaagaaa aaggctagta catatgattg gtctgtgaac ctgtgaggtg   480
ggtaggtagg taggtggaga tttttgttaa ctggtgttgt tgacggactc gaacggggcc   540
gggcgtgtgg tgtggctagc tgtggtggtt tgctcgccag ccagccagcc acacatcagc   600
gagcatgcag agcttaagca tgtatgtacg gatcggcttg cttagcggtt aagggtgtgt   660
ttggttttggc ttttggcttt ggcttttgcc cctaaaagc caaaagccaa ccaagggtgt   720
atttggtttg actttttggct tttggcttt gtccctaaa agccaaaagc caaacaaagg   780
gttagatcta ggaagcagct ttttctaaaa gctggctttc tcacagtgca aatctgaaag   840
cacccctgaa cctgctttta gtggcttttc gaatggaact gtgaaaacat atatcgaaga   900
acttttaacg acttttagtg gtttccacca aacagtttag cttttaacg gcttacagcc    960
tacaacagct ttttccacag ctcacagccc acagcaactt ttttcacagc cacagcccaa  1020
ccaaacagac cccaaagggc tgaatccagg aagcagcttt ttctaaaagc cgactttctc  1080
gtagtgtaaa actgaaaaca cccctggacc tgcttttagt ggcttttgga tggaactgtg  1140
aaaacatata tcgaagaact tttaacgact tttagtggtt tccaccaaac gatttctagc  1200
tttttaacag cacacagcct acaacagctt ttttcacagc cacagcccaa caacaacttt  1260
ttctacagcc acaacccaac caaacgacc ctaaggcggc cgagcgagcg caaagcgtcg  1320
tcagctttga ttgccatgcc atctcctgct ccacttgtct ctctggccgt cgtcagccac  1380
catccaacaa ggccggtgct actggcggct cctaggtaga cgacgacgac gacgacacct  1440
ccaccgttcg ccgccgtcca ctcaccaatc aacacgaac gcccaaaaca cacacacacg  1500
cacgctgggg agggaaaaaa aggcagagac atatgcgtgc gtcgctgcat tattgtacgc  1560
gatcgaatgc catctctctc actctctctc ctcccttttat taatctggta ctggctagct  1620
ggtccggcga caccgacgtg tcagctccgt cgcgcgcgtc cgtccgtccg ctggagcgga  1680
cacggaccgc ggcgtctgtc gatcgccggc tcgccgcagc gcagctacct agcacgctca  1740
cgcatgctac actgcctaca cgcacacggc cggcccaaaa gcgttccctg ccgcctgccg  1800
gccggctttt ttattattat tggaacatga ggctatttct cctccacac gggctacgac  1860
gtgagcacga gtactgggat ccccggatcc gccctctctg tccctgctgc tactccagcc  1920
actgaaatgt tgtcagatga aacagcagag ccgatctccg cacggaaacc catgcacggc  1980
cattcaaatt caggtgccca cgtacgtcag ggtggtcaat atggagaaaa agaaagagta  2040
attaccaatt tttttttcaat tcaaaaatgt agatgtccgc agcgttatta taaaatgaaa  2100
gtacatttttg ataaaacgac aaattacgat ccgtcgtatt tataggcgaa agcaataaac  2160
aaattattct aattcggaaa tcttttatttc gacgtgtcta cattcacgtc caaatggggg  2220
cttagatgag aaacttcacg atttggcgcg ccaaagcttg gtcgagtgga agctagcttt  2280
ccgatcctac ctgtcacttc atcaaaagga cagtagaaaa ggaaggtggc tcctacaaat  2340
gccatcattg cgataaagga aaggccatcg ttgaagatgc ctctgccgac agtggtccca  2400
aagatggacc cccacccacg aggagcatcg tggaaaaaga agacgttcca accacgtctt  2460
caaagcaagt ggattgatgt gatatctcca ctgacgtaag ggatgacgca caatcccact  2520
atccttcgca agacccttcc tctatataag gaagttcatt tcatttggag aggacacgct  2580
gacaagctga ctctagcaga tcctctagaa ccatcttcca cacactcaag ccacactatt  2640
ggagaacaca cagggacaac acaccataag atccaaggga ggcctccgcc gccgccggta  2700
accacccgc ccctctcctc tttctttctc cgttttttt tccgtctcgg tctcgatctt    2760
tggccttggt agtttgggtg ggcgagaggc ggcttcgtgc gcgcccagat cggtgcgcgg  2820
gaggggcggg atctcgcggc tggggctctc gccggcgtgg atccggcccg gatctcgcgg  2880
ggaatggggc tctcggatgt agatctgcga tccgccgttg ttgggggaga tgatgggggg  2940
tttaaaattt ccgccgtgct aaacaagatc aggaagaggg gaaaagggca ctatggttta  3000
tattttttata tatttctgct gcttcgtcag gcttagatgt gctagatctt tcttttcttct  3060
ttttgtgggt agaatttgaa tccctcagca ttgttcatcg gtagttttc ttttcatgat   3120
ttgtgacaaa tgcagcctcg tgcggagctt ttttgtaggt agaagtgatc aaccatggac  3180
aacaacccaa acatcaacga gtgcatcccg tacaactgcc tcagcaaccc tgaggtcgag  3240
gtgctcggcg gtgagcgcat cgagaccggt tacacccca tcgacatctc cctctccctc   3300
acgcagttcc tgctcagcga gttcgtgcca ggcgctggct tcgtcctggg cctcgtggac  3360
atcatctggg gcatctttgg cccctcccag tgggacgcct tcctggtgca aatcgagcag  3420
ctcatcaacc agaggatcga ggagttcgcc aggaaccagg ccatcagccg cctggagggc  3480
ctcagcaacc tctaccaaat ctacgctgag agcttccgcg agtgggagc cgaccccact  3540
aacccagctc tccgcgagga gatgcgcatc cagttcaacg acatgaacag cgccctgacc  3600
accgccatcc cactcttcgc cgtccagaac taccaagtcc cgtcctgtc cgtgtacgtc  3660
caggccgcca acctgcacct cagcgtgctg agggacgtca gcgtgtttgg ccagaggtgg  3720
ggcttcgacg ccgccaccat caacagccgc tacaacgacc tcaccaggct gatcggcaac  3780
tacaccgacc acgctgtccg ctggtacaac actgcgctg agcgcgtctg gggccctagt  3840
tctagagact ggattcgcta caaccagttc aggcgcgagc tgaccctcac cgtcctggac  3900
attgtgtccc tcttcccgaa ctacgactcc cgcacctacc cgatccgcac cgtgtcccaa  3960
ctgacccgcg aaatctacac caaccccgtc ctggagaact cgacggtag cttcagggc    4020
agcgcccagg gcatcgaggg ctccatcagg agcccacacc tgatggacat cctcaacagc  4080
atcactatct acaccgatgc ccaccgcggc gagtactact ggtccggcca ccagatcatg  4140
gcctccccgg tcggcttcag cggccccgag tttaccttc ctctctacgg cacgatgggc  4200
aacgccgctc cacaacaacg catcgtcgct cagctgggcc agggcgtcta ccgcaccctg  4260
agctccaccc tgtaccgcag gccttcaac atcggtatca caaccagca gctgtccgtc  4320
ctggatggca ctgagttcgc ctacggcacc tcctccaacc tgcctccgc tgtctaccgc  4380
aagagcggca cggtggattc cctggacgag atcccaccac agaacaacaa tgtgcccccc  4440
```

```
aggcagggtt tttcccacag gctcagccac gtgtccatgt tccgctccgg cttcagcaac  4500
tcgtccgtga gcatcatcag agctcctatg ttctcttgga tacaccgtag tgctgagttc  4560
aacaacatca ttgcatccga cagcattact caaatacccct tggtgaaagc acatacactt  4620
cagtcaggta ctactgttgt cagaggtcca gggtttacag gaggagacat tcttcgtcgc  4680
acaagtggag gacccttttgc ttacactatt gttaacatca atggccaatt gccccaaagg  4740
tatcgtgcaa gaatccgcta tgcctctact acaaatctca ggatctacgt gactgttgca  4800
ggtgaaagga tctttgctgg tcagttcaac aagactatgg ataccggtga cccttttgaca  4860
ttccaatctt ttagctacgc aactatcaac acagctttta cattcccaat gagccagagt  4920
agcttcacag taggtgctga cactttcagc tcagggaatg aagtttacat cgacaggttt  4980
gaattgattc cagttactgc aaccctcgag gctgagtaca accttgagag agcccagaag  5040
gctgtgaacg ccctctttac ctccaccaat cagcttggct tgaaaactaa cgttactgac  5100
tatcacattg accaagtgtc caacttggtc acctacctta gcgatgagtt ctgcctcgac  5160
gagaagcgtg aactctccga gaaagttaaa cacgccaagc gtctcagcga cgagaggaat  5220
ctcttgcaag actccaactt caaagacatc aacaggcagc cagaacgtgg ttggggtgga  5280
agcaccggga tcaccatcca aggaggcgac gatgtgttca aggagaacta cgtcaccctc  5340
tccggaactt cgacgagtg ctaccctacc tactgtacc agaagatcga tgagtccaaa  5400
ctcaaagcct tcaccaggta tcaacttaga ggctacatcg aagacagcca agaccttgaa  5460
atctactcga tcaggtacaa tgccaagcac gagaccgtga atgtcccagg tactggttcc  5520
ctctggccac tttctgccca atctcccatt gggaagtgtg gagagcctaa cagatgcgct  5580
ccacaccttg agtggaatcc tgacttggac tgctcctgca gggatggcga gaagtgtgcc  5640
caccattctc atcacttctc cttggacatc gatgtgggat gtactgacct gaatgaggac  5700
ctcggagtct gggtcatctt caagatcaag acccaagacg gacacgcaag acttggcaac  5760
cttgagttcc tcgaagagaa accattggtc ggtgaagctc tcgctcgtgt gaagagagca  5820
gagaagaagt ggagggacaa acgtgagaaa ctcgaatggg aaactaacat cgtttacaag  5880
gaggccaaag agtccgtgga tgcttttgttc gtgaactccc aatatgatca gttgcaagcc  5940
gacaccaaca tcgccatgat ccacgccgca gacaaacgtg tgcacagcat tcgtgaggct  6000
tacttgcctg agttgtccgt gatccctggt gtgaacgctg ccatcttcga ggaacttgag  6060
ggacgtatct ttaccgcatt ctccttgtac gatgccagaa acgtcatcaa gaacggtgac  6120
ttcaacaatg gcctcagctg ctggaatgtg aaggtcatg tggacgtgga ggaacagaac  6180
aatcagcgtt ccgtcctggt tgtgcctgag tgggaagctg aagtgtccca agaggttaga  6240
gtctgtccag gtagaggcta cattctccgt gtgaccgctt acaaggaggg atacggtgag  6300
ggttgcgtga ccatccacga gatcgagaac aacaccgacg agcttaagtt ctccaactgc  6360
gtcgaggaag aaatctatcc caacaacacc gttacttgca acgactacac tgtgaatcag  6420
gaagagtacg gaggtgccta cactagccgt aacagaggtt acaacgaagc tccttccgtt  6480
cctgctgact atgcctccgt gtacgaggag aaatcctaca cagatggcag acgtgagaac  6540
ccttgcgagt tcaacagagg ttacagggac tacacaccac ttccagttgg ctatgttacc  6600
aaggagcttg agtactttcc tgagaccgac aaagtgtgga tcgagatcgg tgaaaccgag  6660
ggaaccttca tcgtggacag cgtggagctt ctcttgatgg aggaataatg agatctatcg  6720
attctagaag gcctgaattc tgcatgcatg tggacgtatg ctcattcagg ttggagccaa  6780
tttggttgat gtgtgtgcga gttcttgcga gtctgatgag acatctctgt attgtgtttc  6840
tttccccagt gtttctgta cttgtgtaat cggctaatcg ccaacagatt cggcgatgaa  6900
taaatgagaa ataaattgtt ctgattttga gtgcaaaaaa aaaggaatta gatctgtgtg  6960
tgttttttgg atccccgggg cggccgcgtt aacaagcttg agctcaggat ttagcagcat  7020
tccagattgg gttcaatcaa caaggtacga gccatatcac tttattcaaa ttggtatcgc  7080
caaaaccaag aaggaactcc catccctcaaa ggtttgtaag gaagaattct cagtccaaag  7140
cctcaacaag gtcagggtac agagtctcca aaccattagc caaaagctac aggagatcaa  7200
tgaagaatct tcaatcaaag taaactactg ttccagcaca tgcatcatga tcagtaagtt  7260
tcagaaaaag acatccaccg aagacttaaa gttagtgggc atctttgaaa gtaatcttgt  7320
caacatcgag cagctggctt gtggggacca gacaaaaaag gaatggtgca gaattgttag  7380
gcgcacctac caaaagcatc tttgccttta ttgcaaagat aaagcagatt cctctagtac  7440
aagtggggaa caaataacg tggaaaagag ctgtcctgac agcccactca ctaatgcgta  7500
tgacgaacgc agtgacgacc acaaaagaat tccctctata taagaaggca ttcattccca  7560
tttgaaggat catcagatac tcaaccaatc cttctaggat ctaccgtctt cggtacgcgc  7620
tcactccgcc ctctgccttt gttactgcca cgtttctctg aatgctctct tgtgtggtga  7680
ttgctgagag tggtttagct ggatctagaa ttacactcgt aaatcgtgtt ctgcctgtgc  7740
tgattacttg ccgtcctttg tagcagcaaa atatagggac atggtagtac gaaacgaaga  7800
tagaacctac acagcaatac gagaaatgtg taatttggtg cttagcggta ttttatttaag  7860
cacatgttgg tgttataggg cacttggatt cagaagtttg ctgttaattt aggcacaggc  7920
ttcatactac atgggtcaat agtataggga ttcatattat aggcagatact ataataattt  7980
gttcgtctgc agagcttatt atttgccaaa attagatatt cctattctgt ttttgtttgt  8040
gtgctgttaa attgttaacg cctgaaggaa taaatataaa tgacgaaatt ttgatgttta  8100
tctctgctcc tttattgtga ccataagtca agatcagatg cacttgtttt aaatattgtt  8160
gtctgaagaa ataagtactg acagtatttt gatgcattga tctgcttgtt tgttgtaaca  8220
aaatttaaaa ataaagagtt tcctttttgt tgctctcctt acctcctgat ggtatctagt  8280
atctaccaac tgacactata ttgcttctct ttacatacgt atcttgctcg atgccttctc  8340
cctagtgttg accagtgtta ctcacatagt cttttgctcat tcattgtaa tgcagatacc  8400
aagcggcctc tagaggatca gcatggcgcc caccgtgatg atggcctcgt cggccaccgc  8460
cgtcgctccg ttccagggc tcaagtccaa cgccagccgg ccgtcgccc gccgctcctc  8520
cagaagcctc ggcaacgtca gcaacgcgg aaggatccga tgcatgcagg taacaaatgc  8580
atcctagcta gtagttcttt gcattggcagc agctgcagct agcgagttag taataggaag  8640
ggaactgatg atccatgcat ggactgatgt gtgttgccca tcccatccca tttcccaacc  8700
ccaaacgaac caaaacacac gtactacgtg caggtgtggc cggcctacgg caacaagaag  8760
ttcgagacgc tgtcgtacct gccgccgctg tcgaccggcc ggcgcatccg ctgcatgcag  8820
gccatgacca actccgtcct gaactctggt cgcaaccca tctgcagcat ctacaacctc  8880
gcggcgcatg atccattcag cttccagcac aagagcctcg acactgttca agggagtgg  8940
acggagtgga agaagaacaa ccacagcctg tacctgacc ccatcgtcgg cacggtggcc  9000
agcttccttc tcaagaaggt cggctctctc gtcgggaagc gcatcctctc ggaactccgc  9060
aacctgatct ttccatctgg ctccaccaac ctcatgcaag acatcctcag ggagaccgag  9120
aagtttctca accagcgcct caacactgat acccttgctc gcgtcaacgc tgagctgacg  9180
```

```
ggtctgcaag caaacgtgga ggagttcaac cgccaagtgg acaacttcct caaccccaac   9240
cgcaatgcgg tgcctctgtc catcacttct tccgtgaaca ccatgcaaca actgttcctc   9300
aaccgcttgc ctcagttcca gatgcaaggc taccagctgc tcctgctgcc actctttgct   9360
caggctgcca acctgcacct ctccttcatt cgtgacgtga tcctcaacgc tgacgagtgg   9420
ggcatctctg cagccacgct gaggacctac cgcgactacc tgaagaacta caccagggac   9480
tactccaact attgcatcaa cacctaccag tcggccttca agggcctcaa tacgaggctt   9540
cacgacatgc tggagttcag gacctacatg ttcctgaacg tgttcgagta cgtcagcatc   9600
tggtcgctct tcaagtacca gagcctgctg tgtccagcg cgccaacct ctacgccagc   9660
ggctctggtc cccaacaaac tcagagcttc accagccagg actggccatt cctgtattcg   9720
ttgttccaag tcaactccaa ctacgtcctc aacggcttct ctggtgctcg cctctccaac   9780
accttcccca acattgttgg cctccccggc tccaccacaa ctcatgctct gcttgctgcc   9840
agagtgaact actccggcgg catctcgagc ggcgacattg tgcatcgcc gttcaaccag   9900
aacttcaact gctccacctt cctgccgccg ctgctcaccc cgttcgtgag gtcctggctc   9960
gacagcggct ccgaccgcga gggcgtggcc accgtcacca actggcaaac cgagtccttc  10020
gagaccaccc ttggcctccg gagcggccgc ttcacggccg cgtggaaatt c taactacttc  10080
cccgactact tcatcaggaa catctctggt gttcctctcg tcgtccgcaa cgaggacctc  10140
cgccgtccac tgcactacaa cgagatcagg aacatcgcct ctccgtccgg gacgcccgga  10200
ggtcaagggg cgtacatggt gagcgtccat aacaggaaga acaacatcca cgctgtgcat  10260
gagaacggct ccatgatcca cctggcgccc aatgattaca ccggcttcac catctctcca  10320
atccacgcca cccaagtgaa caaccagaca cgcaccttca tctccgagaa gttcggcaac  10380
cagggcgact ccctgaggtt cgagcagaac aacaccaccg ccaggtacac cctgcgcggc  10440
aacggcaaca gctacaacct gtacctgcgc gtcagctcca ttggcaactc caccatcagg  10500
gtcaccatca cgggagggt gtacacagcc accaatgtga acacgacgac caacaatgat  10560
ggcgtcaacg acaacggcgc ccgcttcagc gacatcaaca ttggcaacgt ggtgccagc  10620
agcaactccg acgtccgct ggacatcaac gtgaccctga actctggcac ccagttcgac  10680
ctcatgaaca tcatgctggt gccaactaac atctcgccgc tgtactgata ggagctctga  10740
tccccatggg aattcccgat cgttcaaaca tttggcaata agtttctta agattgaatc  10800
ctgttgccgg tcttgcgatg attatcatat aatttctgtt gaattacgtt aagcatgtaa  10860
taattaacat gtaatgcatg acgttattta tgagatgggt tttatgattc agagtcccgc  10920
aattatacat ttaatacgcg atagaaaaca aaatatagcg cgcaaactag gataaattat  10980
cgcgcgcggt gtcatctatg ttactagatc ggggatatcc ccggggcggc cgcggggaat  11040
tcggtaccaa gctttggcgc gccaaatcgt gaagttctc atctaagccc ccatttggac  11100
gtgaatgtag acacgtcgaa ataaagattt ccgaattaga ataatttgtt tattgctttc  11160
gcctataaat acgacggatc gtaatttgtc gttttatcaa aatgtacttt catttataa  11220
taacgctgcg gacatctaca tttttgaatt gaaaaaaaat tggtaattac tctttctttt  11280
tctccatatt gaccatcata tcattgcat ccccggaaat tatgtttttt taaaaaccac  11340
ggtattatag ataccgtgtt attttttgag tattggaaat tcatttcaa cccaaagttt  11400
cttcatggca catctagctt ttgcctaata ccatgtaggg ctacatctta aaaatctata  11460
ctactatatt aaagctgcag gggtagcctg tctccacctg gttctgcctc gagccaatct  11520
aaaccgtcca tctatatcca tcaaatcagc accgtccggt ccgtgcgcac ctcctctccc  11580
gctattcagt tgcatacttg cagcaggttc tccctcctca ccatttcctc tgcctcctct  11640
ctcgctcact ggtcagattc atcctgcctc tcccgcatgc gctccctccc catgcccgt  11700
ctcgcactat gccacacct caccgcgggg agacgaagac gttggacgca tcctcacctc  11760
ctccgctagt tgtcgctctt ccatcctctt caacaacttc tacataggga gaggcggttc  11820
ggcgtcccga cgccgccgct tctcccctcc ccatggagga cgagaacatc gacctcggcg  11880
gcgggggcga tgcctccgct ctgcatagag gagggttgta gtggcaagca gcaatgccaa  11940
caccgggcgg ggcaaagact aggcaacaat aggacggcac gcccggttgt cagcgaggtg  12000
gcggcatcgt gtgccgctac cgaacaaacat ctccggcgct ggagtcggtg agttactgcg  12060
ccacccggac gccctcaatg cactgatatc tacccggtct ccatcgccgc ccttcctccc  12120
ttccctctcc ctgtgcctcc ctctcttgcc ctctcccttc caactgctcc cgccccagcc  12180
ctagcccaac cacctcccgc gcagggtcac caa                              12213

SEQ ID NO: 28        moltype = DNA   length = 12274
FEATURE              Location/Qualifiers
source               1..12274
                     mol_type = other DNA
                     organism = synthetic construct
SEQUENCE: 28
aatatttaaa aatggaagta atactatatt aaaatgattc atgtggaact cctgcgcttc     60
tttttgaagt ttcaaaaggg agctttcagg gtcgcttaga gtttgtttgg ttggaaatac    120
aagcgaaaag agagctaatg aggggacat ccatattttc tatggtgttt gaataagagt    180
cacgcggaa taagatgaac accgaaacaa ttttttgta gctacgtggt tccaaaaaat    240
cgagtagacg gtgtcgcttc cacctcatac tacttcaacc tcaaaccaca catccttacg    300
cgcccgccgg tgtctccgtc gtctcaagtt ctcaacatac ctacacatgt aaccactacc    360
ggtctttgtc atgttttcgaa agaagattac aggtcctcta gaagagaggga cgccggggtgg    420
cgagaaagct ggggaagaaa aaggctagta catatgattg gtctgtgaac ctgtgaggtg    480
ggtaggtagg taggtggaga tttttgttaa ctggtgttgt tgacggactc gaacgggggcc    540
gggcgtgtgg tgtggctagc tgtggtggtt tgctcgccag ccagccagcc acacatcagc    600
gagcatgcag agcttaagca tgtatgtacg gatcggcttg cttagcggtt aagggtgtgt    660
ttggtttggc ttttgctttt ggcttttgcc ccctaaaagc caaaagccaa ccaagggtgt    720
atttggtttg acttttggct tttggctttt gtccctaaaa agccaaaagc caaacaaagg    780
gttagatcta ggaagcagct ttttctaaaa gctggctttc tcacagtgca aatctgaaag    840
caccccctgaa cctgctttta gtggcttttc gaatggaact gtgaaacat atatcgaaga    900
actttaacg actttttagtg gtttcaccca aacagttcaaccg gcttacgcc    960
tacaacagct ttttcacag ctcacagccc acagcaactt ttttcacagc cacagccaa   1020
ccaaacagac cccaaagggc tgaatccagg aagcagcttt ttctaaaagc cgactttctc   1080
gtagtgtaaa actgaaaaca cccctggacc tgcttttagt ggcttttgga tggaactgtg   1140
aaaacatata tcgaagaact tttaacgact tttagtggtt tccaccaaac gatttctagc   1200
tttttaacag cacacagcct acaacagctt ttttcacagc tcacagccca caacaacttt   1260
```

```
ttctacagcc acaacccaac caaacggacc ctaaggcggc cgagcgagcg caaagcgtcg   1320
tcagctttga ttgccatgcc atctcctgct ccacttgtct ctctggccgt cgtcagccac   1380
catccaacaa ggccggtgct actggcggct cctaggtaga cgacgacgac gacgacacct   1440
ccaccgttcg ccgccgtcca ctcaccaatc aacacggaac gcccaaaaca cacacacacg   1500
cacgctgggg agggaaaaaa aggcagagac atatgcgtgc gtcgctgcat tattgtacgc   1560
gatcgaatgg catctctctc actctctctc ctcccttat taatctggta ctggctagct   1620
ggtccggcga caccgacgtg tcagctccgt cgcgcgcgtc cgtccgtccg ctggagcgga   1680
cacggaccgc ggcgtctgtc gatcgccggc tcgccgcagc gcagctacct agcacgctca   1740
cgcatgctac actgcctaca cgcacacggc cggcccaaaa gcgttccctg ccgcctgccg   1800
gccggctttt ttattattat tggaacatga ggctatttct cctcccacac gggctacgac   1860
gtgagcacga gtactgggat ccccggatcc gccctctctg tccctgctgc tactccagcc   1920
actgaaatgt tgtcagatga aacagcagag ccgatctccg cacggaaacc catgcacggc   1980
cattcaaatt caggtgccca cgtacgtcag ggtgctgctg ctactactat caagccaata   2040
aaaggatggt aatgagtatg atggatcaga tgatgctgaa tatggagaaa aagaaaagat   2100
aattaccaat ttttttttcaa ttcaaaaatg tagatgtccg cagcgttatt ataaaatgaa   2160
agtacatttt gataaaacga caaattacga tccgtcgtat ttataggcga aagcaataaa   2220
caaattattc taattcggaa atcttttattt cgacgtgtct acattcacgt ccaaatgggg   2280
gcttagatga gaaacttcac gatttggcgc gccaaagctt ggtcgagtgg aagctagctt   2340
tccgatccta cctgtcactt catcaaaagg acagtagaaa aggaaggtgg ctcctacaaa   2400
tgccatcatt gcgataaagg aaaggccatc gttgaagatg cctctgccga cagtggtccc   2460
aaagatggac ccccacccac gaggagcatc gtggaaaaag aagacgttcc aaccacgtct   2520
tcaaagcaag tggattgatg tgatatctcc actgacgtaa gggatgacgc acaatcccac   2580
tatccttcgc aagacccttc ctctatataa ggaagttcat ttcatttgga gaggacacgc   2640
tgacaagctg actctagcag atcctctaga accatcttcc acacactcaa gccacactat   2700
tggagaacac acagggacaa cacaccataa gatccaaggg aggcctccgc cgccgccggt   2760
aaccaccccg cccctctcct cttctttct ccgtttttttt ttccgtctcg gtctcgatct   2820
ttggccttgg tagtttgggt gggcgagagg cggcttcgtg cgcgcccaga tcggtgcgcg   2880
ggaggggcgg gatctcgcgg ctggggctct cgccggcgtg gatccggccc ggatctcgcg   2940
gggaatgggg ctctcggatg tagatctgcg atccgccgtt gttgggggag atgatggggg   3000
gtttaaaatt tccgccgtgc taaacaagat caggaagagg ggaaaagggc actatggttt   3060
atatttttat atatttctgc tgcttcgtca ggcttagatg tgctagatct ttctttcttc   3120
tttttgtggg tagaatttga atccctcagc attgttcatc ggtagttttt cttttcatga   3180
tttgtgacaa atgcagcctc gtgcggagct ttttgtagg tagaagtgat caaccatgga   3240
caacaaccca aacatcaacg agtgcatccc gtacaactgc ctcagcaacc ctgaggtcga   3300
ggtgctcggc ggtgagcgca tcgagaccgg ttacaccccc atcgacatct ccctctccct   3360
cacgcagttc ctgctcagcg agttcgtgcc aggcgctggc ttcgtcctgg gcctcgtgga   3420
catcatctgg ggcatctttg gcccctccca gtgggacgcc ttcctggtgc aaatcgagca   3480
gctcatcaac cagaggatcg aggagttcgc caggaaccag gccatcagcc gctggagggg   3540
cctcagcaac ctctaccaaa tctacgctga gagcttccgc gagtgggagg ccgaccccac   3600
taacccagct ctccgcgagg agatgcgcat ccagttcaac gacatgaaca gcgccctgac   3660
caccgccatc ccactcttcg ccgtccagaa ctaccaagtc ccgctcctgt ccgtgtacgt   3720
ccaggccgcc aacctgcacc tcagcgtgct gagggacgtc agcgtgtttg ccagaggtgt   3780
gggcttgac gccgccacca tcaacagccg ctacaacgcc ctcaccaggc tgatcggcaa   3840
ctacaccgac cacgctgtcc gctggtacaa cactggcctg gagcgcgtct ggggccctga   3900
ttctagagac tggattcgct acaaccagtt caggcgcgag ctgaccctca ccgtcctgga   3960
cattgtgtcc ctcttcccga actacgactc ccgcacctac ccgatccgca ccgtgtccca   4020
actgacccgc gaaatctaca ccaacccgt cctggagaac ttcgacggta gcttcagggg   4080
cagcgcccag ggcatcgagg gctccatcag gagcccacac ctgatggaca tcctcaacag   4140
catcactatc tacaccgatg cccaccgcgg cgagtactac tggtccggcc accagatcat   4200
ggcctccccg gtcggcttca gcggccccga gtttaccttt cctctctacg gcacgatggg   4260
caacgcgct ccacaacaac gcatcgtcgc tcagctgcc cagggcgtct accgcaccct   4320
gagctccacc ctgtaccgca ggcccttcaa catcggtatc aacaaccagc agctgtccgt   4380
cctggatggc actgagttcg cctacggcac ctcctccaac ctgccctccg ctgtctaccg   4440
caagagcggc acgtggatt ccctggacga gatcccacca cagaacaaca atgtgccccc   4500
caggcagggt ttttcccaca ggctcagcca cgtgtccatg ttccgctccg gcttcagcaa   4560
ctcgtccgtg agcatcatca gagctcctat gttctcttgg atacaccgta gtgctgagtt   4620
caacaacatc attgcatccg acagcattac tcaaataccc ttggtgaaag cacatacact   4680
tcagtcaggt actactgttg tcagaggtcc agggtttaca ggaggagaca ttcttcgtcg   4740
cacaagtgga ggacccttg cttacactat tgttaacatc aatggccaat tgccccaaag   4800
gtatcgtgca agaatccgct atgcctctac tacaaatctc aggatctacg tgactgttgc   4860
aggtgaaagg atctttgctg gtcagttcaa caagactatg gataccggtg accctttgac   4920
attccaatct tttagctacg caactatcaa cacagctttt acattccaa tgagccagag   4980
tagcttcaca gtaggtgctg acacttcag ctcagggaat gaagtttaca tcgacaggtt   5040
tgaattgatt ccagttactg caaccctcga ggctgagtac aaccttgaga gagcccagaa   5100
ggctgtgaac gccctctta cctccaccaa tcagcttggc ttgaaaacta acgttactga   5160
ctatcacatt gaccaagtgt ccaacttggt cacctacctt agcgatgagt ctgcctcga   5220
cgagaagcgt gaactctccg agaaagttaa acacgccaag cgtctcagcg acgagaggaa   5280
tctcttgcaa gactccaact tcaaagacat caacaggcag ccagaacgtg gttgggtgg   5340
aagcaccggg atcaccatcc aaggaggcga cgatgtgttc aaggagaact acgtcaccct   5400
ctccggaact ttcgacgagt gctaccctac ctacttgtac cagaagatcg atgagtccaa   5460
actcaaagcc ttcaccaggt atcaacttag aggctacatc gaagacagcc aagaccttga   5520
aatctactcg atcaggtaca atgccaagca cgagaccgtg aatgtcccag gtactggttc   5580
cctctggcca ctttctgccc aatctcccat gggaagtgt ggagagccta acagatgcgc   5640
tccacaccttt gagtcgaatc ctgacttgga ctgctcctgc aggatgggcg agaagtgttt   5700
ccaccattct catcacttct ccttggacat cgatgtggga tgtactgacc tgaatgagga   5760
cctcggagtc tgggtcatct tcaagatcaa gacccaagac ggacacgcaa gacttggcaa   5820
ccttgagttt ctcgaagaga aaccattggt cggtgaagct ctcgctcgtg tgaagagagc   5880
agagaagaag tggagggaca aacgtgagaa actcgaatgg gaaactaaca tcgtttacaa   5940
ggaggccaaa gagtccgtgg atgctttgtt cgtgaactcc caatatgatc agttgcaagc   6000
```

```
cgacaccaac atcgccatga tccacgccgc agacaaacgt gtgcacagca ttcgtgaggc   6060
ttacttgcct gagttgtccg tgatccctgg tgtgaacgct gccatcttcg aggaacttga   6120
gggacgtatc tttaccgcat tctccttgta cgatgccaga aacgtcatca agaacggtga   6180
cttcaacaat ggcctcagct gctggaatgt gaaaggtcat gtggacgtgg aggaacagaa   6240
caatcagcgt tccgtcctgg ttgtgcctga gtgggaagct gaagtgtccc aagaggttag   6300
agtctgtcca ggtagaggct acattctccg tgtgacccgt tacaaggagg gatacggtga   6360
gggttgcgtg accatccacg agatcgagaa caacaccgac gagcttaagt tctccaactg   6420
cgtcgaggaa gaaatctatc ccaacaacac cgttacttgc aacgactaca ctgtgaatca   6480
ggaagagtac ggaggtgcct acactagccg taacagaggt tacaacgagg ctccttccgt   6540
tcctgctgac tatgcctccg tgtacgagga gaaatcctac acagatggca gacgtgagaa   6600
cccttgcgag ttcaacagag gttacaggga ctacacacca cttccagttg gctatgttac   6660
caaggagctt gagtactttc ctgagaccga caaagtgtgg atcgagatcg tgaaaccga   6720
gggaaccttc atcgtggaca gcgtggagct tctcttgatg gaggaataat gagatctatc   6780
gattctagaa ggcctgaatt ctgcatgcgt ttggacgtat gctcattcag gttggagcca   6840
atttggttga tgtgtgtgcg agttcttgcg agtctgatga gacatctctg tattgtgttt   6900
cttccccag tgttttctgt acttgtgtaa tcggctaatc gccaacagat tcggcgatga   6960
ataaatgaga aataaaattgt tctgattttg agtgcaaaaa aaaggaatt agatctgtgt   7020
gtgtttttg gatccccggg gcggccgcgt taacaagct gagctcagga tttagcagca   7080
ttccagattg ggttcaatca acaaggtacg agccatatca ctttattcaa attggtatcg   7140
ccaaaaccaa gaaggaactc ccatcctcaa aggtttgtaa ggaagaattc tcagtccaaa   7200
gcctcaacaa ggtcagggta cagagtctcc aaaccattag ccaaaagcta caggagatca   7260
atgaagaatc ttcaatcaaa gtaaactact gttccagcac atgcatcatg gtcagtaagt   7320
ttcagaaaaa gacatccacc gaagacttaa agttagtggg catctttgaa agtaatcttg   7380
tcaacatcga gcagctggct tgtggggacc agacaaaaaa ggaatggtgc agaattgtta   7440
ggcgcaccta ccaaaagcat ctttgccttt attgcaaaga taaagcagat tcctctagta   7500
caagtgggga acaaaataac gtggaaaaga gctgtcctga cagcccactc actaatgcgt   7560
atgacgaacg cagtgacgac cacaaaagaa ttccctctat ataagaaggc attcattccc   7620
atttgaagga tcatcagata ctcaaccaat ccttctagga tctaccgtct tcggtacgcg   7680
ctcactccgc cctctgcctt tgttactgcc acgtttctct gaatgctctc ttgtgtggtg   7740
attgctgaga gtggtttagc tggatctaga attacactct gaaatcgtgt tctgcctgtg   7800
ctgattactt gccgtccttt gtagcagcaa aatatagga catggtagta cgaaacgaag   7860
atagaaccta cacagcaata cgagaaatgt gtaatttggt gcttagcggt atttatttaa   7920
gcacatgttg gtgttatagg gcacttggat tcagaagttt gctgttaatt taggcacagg   7980
cttcatacta catgggtcaa tagtatagg attcatatta taggcgatac tataataatt   8040
tgttcgtctg cagagcttat tatttgccaa aattagatat tcctattctg tttttgtttg   8100
tgtgctgtta aattgttaac gcctgaagga ataaatataa atgacgaaat tttgatgttt   8160
atctctgctc ctttattgtg accataagtc aagatcagat gcacttgttt taaatattgt   8220
tgtctgaaga aataagtact gacagtattt tgatgctcag atctgcttgt ttgttgtaac   8280
aaaatttaaa aataaagagt ttccttttg ttgctctcta tacctcctga tggtatctag   8340
tatctaccaa ctgacactat attgcttctc tttacatacg tatcttgctc gatgccttct   8400
ccctagtgtt gaccagtgtt actcacatag tctttgctca tttcattgta atgcagatac   8460
caagcggcct ctagaggatc agcatggcgc ccaccgtgat gatggcctcg tcggccaccg   8520
ccgtcgctcc gttccagggg ctcaagtcca ccgccgacct ccccgtcgcc cgccgctcct   8580
ccagaagcct cggcaacgtc agcaacggcg gaaggatccg gtgcatgcag gtaacaaatg   8640
catcctagct agtagttctt tgcattgcag cagctgcagc tagcgagtta gtaataggaa   8700
gggaactgat gatccatgca tggactgatg tgtgttgccc atcccatccc atttcccaac   8760
cccaaacgaa ccaaaacaca cgtactacgt gcaggtgtgg ccggcctacg gcaacaagaa   8820
gttcgagacg ctgtcgtacc tgccgccgct gtcgaccggc gggcgcatcc gctgcatgca   8880
ggccatggac aactccgtcc tgaactctgg tcgcaccacc atctgcgacg cctacaacgt   8940
cgcggcgcat gatccattca gcttccagca caagagcctc gacactgttc agaaggagtg   9000
gacggagtgg aagaagaaca accacagcct gtacctggac cccatcgtcg gcacggtggc   9060
cagcttcctt ctcaagaagg tcggctctct cgtcggaagc gcatcctct cggaactccg   9120
caacctgatc tttccatctg gctccaccaa cctcatgcaa gacatcctca gggagaccga   9180
gaagtttctc aaccagcgcc tcaacactga tacccttgct cgcgtcaacg ctgagctgac   9240
gggtctgcaa gcaaagtggg aggagttcaa ccgccaaggg gacaacttcc tcaacccaa   9300
ccgcaatgcg gtgcctctgt ccatcactt tccgtgaac accatgcaac aactgttcct   9360
caaccgcttg cctcagttcc agatgcaagg ctaccagctg ctcctgctgc cactctttgc   9420
tcaggctgcc aacctgcacc tctccttcat tcgtgacgtg atcctcaacg ctgacgagtg   9480
gggcatctct gcagccacgc tgaggaccta ccgcgactac actgaagaact acaccaggga   9540
ctactccaac tattgcatca acacctacca gtcggccttc aagggcctca atacgagget   9600
tcacgacatg ctggagttca ggacctacat gttcctgaac gtgttcgagt acgtcagcat   9660
ctggtcgctc ttcaagtacc agagcctgct ggtgtccagc ggcgcaaacc tctacgccag   9720
cggctctggt ccccaacaaa tcagagcttt caccagccag gactggccat tcctgtattc   9780
gttgttcaa gtcaactcca actacgtcct caacggctc tctggtgctc gcctctccaa   9840
caccttcccc aacattgttg gcctcccgg ctccaccaca actcatgctc tgcttgctgc   9900
cagagtgaac tactccggcg gcatctcgag cggcgacatt ggtgcatcgc cgttcaacca   9960
gaacttcaac tgctccacct tcctgccgcc gctgctcacc ccgttcgtga ggtcctggct  10020
cgacagcggc tccgaccgcg agggcgtggc caccgtcacc aactgcaaa ccgagtcctt  10080
cgagaccacc cttggcctcc ggagcggcgc cttcacggcg cgtggaaatt ctaactactt  10140
ccccgactac ttcatcagga acatctctgg tgttcctctc gtcgtccgca acgaggacct  10200
ccgccgtcca ctgcactaca acgagatcag gaacatcgcc tctccgtccg ggacgcccgg  10260
aggtgcaagg gcgtacatgg tgagcgtcca taacaggaag aacaacatcc acgctgtgca  10320
tgagaacggc tccatgatcc acctggcgcc caatgattac accggcttca ccatctctcc  10380
aatccacgcc acccaagtga acaaccagac acgcacctc tcctccgaga agttcggcaa  10440
ccaggggcgac tccctgaggt tcgagcagaa caacaccacc gccaggtaca ccctgcgcgg  10500
caacggcaac agctacaacc tgtacctgcg cgtcagctcc attggcaact ccaccatcag  10560
ggtcaccatc aacggagggg tgtacacagc caccaatgtg aacacgacga ccaacaatga  10620
tggcgtcaac gacaacggcg cccgcttcag cgacatcaac attggcaacg tggtggccag  10680
cagcaactcc gacgtcccgc tggacatcaa cgtgaccctg aactctggca cccagttcga  10740
```

```
cctcatgaac atcatgctgg tgccaactaa catctcgccg ctgtactgat aggagctctg  10800
atccccatgg gaattcccga tcgttcaaac atttggcaat aaagtttctt aagattgaat  10860
cctgttgccg gtcttgcgat gattatcata taatttctgt tgaattacgt taagcatgta  10920
ataattaaca tgtaatgcat gacgttattt atgagatggg ttttatgat tagagtcccg  10980
caattataca tttaatacgc gatagaaaac aaaatatagc gcgcaaacta ggataaatta  11040
tcgcgcgcgg tgtcatctat gttactagat cggggatatc cccggggcgg ccgcggggaa  11100
ttcggtacca agctttggcg cgccaaatcg tgaagtttct catctaagcc cccatttgga  11160
cgtgaatgta gacacgtcga aataaagatt tccgaattag aataatttgt ttattgcttt  11220
cgcctataaa tacgacggat cgtaatttgt cgttttatca aaatgtactt tcattttata  11280
ataacgctgc ggacatctac atttttgaat tgaaaaaaa ttggtaatta ctctttcttt  11340
ttctccatat tgaccatcat actcattgca tccccggaaa ttatgttttt ttaaaaacca  11400
cggtattata gataccgtgt tatttttga gtattgaaa tttcatttca acccaaagtt  11460
tcttcatggc acatctagct tttgcctaat accatgtagg gctacatctt aaaaatctat  11520
actactatat taaagctgca ggggtagcct gtctccaatc ggtctgcct cgagccaatc  11580
taaaccgtcc atctatatcc atcaaatcag caccgtccgg tccgtgcgca cctcctctcc  11640
cgctattcag ttgcatactt gcagcaggtt ctccctcctc accatttcct ctgcctcctc  11700
tctcgctcac tggtcagatt catcctgcct ctcccgcatg cgctccctcc ccatgccccg  11760
tctcgcacta tcgccacacc tcaccgcggg gagacgaaga cggtggacgc atcctcacct  11820
cctccgctag ttgtcgctct tccatctctc tcaacaactt ctacataggg agaggcggtt  11880
cggcgtcccg acgccgccgc ttctccccct cccatggagg acgagaacat cgacctcggc  11940
ggcggggcg atgcctccgc tctgcataga ggagggttgt agtggcaagc agcaatgcca  12000
acaccgaggc gggccaagac taggcaacaa taggacggca cgcccggttg tcagcgaggt  12060
ggcggcatcg tgtgccgcta ccgaacaaca tctccggcgc tggagtcggt gagttactgc  12120
gccaccggga cgccctcaat gcactgatat ctacccggtc tccatcgccg cccttcctcc  12180
cttccctctc cctgtgcctc cctctcttgc cctctccctt caactgctc ccgcccagc  12240
cctagcccaa ccacctcccg cgcagggtca ccaa                              12274

SEQ ID NO: 29           moltype = DNA   length = 12273
FEATURE                 Location/Qualifiers
source                  1..12273
                        mol_type = other DNA
                        organism = synthetic construct SEQUENCE: 29
aatatttaaa aatggaagta atactatatt aaaatgattc atgtggaact cctgcgcttc  60
ttttttgaagt ttcaaaaggg agctttcagg gtcgcttaga gtttgtttgg ttggaaatac  120
aagcgaaaag agagctaatg aggggacat ccatattttc tatggtgttt gaataagagt  180
cacgcgggaa taagatgaac accgaaacaa tttttttgta gctacgtggt tccaaaaaat  240
cgagtagacg gtgtcgcttc cacctcatac tacttcaacc tcaaaccaca catccttacg  300
cgcccgccgg tgtctccgtc gtctcaagtt ctcaacatac ctacacatgt aaccactacc  360
ggtctttgtc atgtttcgaa agaagattac aggtcctcta gaagagagga cgccggggtgg  420
cgagaaagct ggggaagaaa aaggctagta catatgattg gtctgtgaac ctgtgaggtg  480
ggtaggtagg taggtggaga ttttttgttaa ctggtgttgt tgacggactc gaacggggcc  540
gggcgtgtgg tgtggctagc tgtggtggtt tgctcgccag ccagccagcc acacatcagc  600
gagcatgcag agcttaagca tgtatgtacg gatcggcttg cttagcggtt aagggtgtgt  660
tggtttggc ttttggcttt ggcttttgcc ccctaaaagc caaagccaa ccaagggtgt  720
atttggtttg acttttggct tttggctttt gtccctaaa agccaaaagc caaacaaagg  780
gttagatcta ggaagcagct ttttctaaaa gctggcttt tcacagtgca aatctgaaag  840
cacccctgaa cctgcttta gtggcttttc gaatggaact gtgaaaacat atatcgaaga  900
actttaacg actttagtg gtttccacca aacagtttag cttttaacg gcttacagcc  960
tacaacagct tttccacag ctcacagccc acagcaactt ttttcacagc cacagcccaa  1020
ccaaacagac cccaaagggc tgaatccagg aagcagcttt ttctaaaagc cgactttctc  1080
gtagtgtaaa actgaaaaca cccctggacc tgcttttagt ggcttttgga tggaactgtg  1140
aaaacatata tcgaagaact tttaacgact tttagtggtt tccacaaac gatttctagc  1200
tttttaacag cacacagcct acaacagctt ttttcacagc tcacagccca caacaacttt  1260
ttctcagcc acaacccaac caaacggacc ctaaggcggc cgagcgagcg caaagcgtcg  1320
tcagctttga ttgccatgcc atctcctgct ccacttgtct ctctggccgt cgtcagccac  1380
catccaacaa ggccggtgct actggcggct cctaggtaga cgacgacgac gacgacacct  1440
ccaccgttcg ccgccgtcca ctcaccaatc aacacggaac gccaaaaaca cacacacacg  1500
cacgctgggg agggaaaaaa aggcagagac atatgcgtgc gtcgctgcat tattgtacgc  1560
gatcgaattga catctctctc actctctctc ctcccttat taatctggta ctggctagct  1620
ggtccggcga caccgacgtg tcagctccgt cgcgcgcgtc cgtccgtccg ctggagcgga  1680
cacggaccgc ggcgtctgtc gatcgccggc tcgccgcagc gcagctacct agcacgctca  1740
cgcatgctac actgcctaca cgcacacggc cggcccaaaa cgttccctg ccgcctgccg  1800
gccggctttt ttattattat tggaacatga ggctattct cctcccaacc gggctacgac  1860
gtgagcacga gtactgggat cccccggatcc gccctctctg tccctgctgc tactccagcc  1920
actgaaatgt tgtcagatga aacagcagag ccgatctccg cacggaaacc catgcacggc  1980
cattcaaatt caggtgccca cgtacgtcag ggtgctgctg ctactactat caagccaata  2040
aaaggatggt aatgagtatg atggatcaat gatggtcaat atggagaaaa agaaagagta  2100
attaccaatt tttttcaat tcaaaaatgt agatgtccgc agcgttatta taaaatgaaa  2160
gtacattttg ataaaacgac aaattacgat ccgtcgtatt tataggcgaa agcaataaac  2220
aaattattct aattcggaaa tctttatttc gacgtgtcta cattcacgtc caaatggggg  2280
cttagatgag aaacttcacg atttggcgcg ccaaagcttg gtcgagtgga agctagcttt  2340
ccgatcctac ctgtcacttc atcaaaagga cagtagaaaa ggaaggtggc tcctacaaat  2400
gccatcattg cgataaagga aaggccgtcg ttgaagatgc ctgccgac agtgtcgca  2460
aagatggacc cccacccacg aggagcatcg tggaaaaaga agacgttcca accacgtctt  2520
caaagcaagt ggattgatgt gatatctcca ctgacgtaag gatgacgca caatcccact  2580
atccttcgca agacccttcc tctatataag gaagttcatt tcatttggag aggacacgct  2640
gacaagctga ctctagcaga tcctctgaaa ccatcttcca cacactcaag ccacactatt  2700
ggagaacaca caggggcaaac acaccataag atccaaggga ggcctccgcc gccgccggta  2760
```

```
accaccccgc ccctctcctc tttctttctc cgtttttttt tccgtctcgg tctcgatctt    2820
tggccttggt agtttgggtg ggcgagaggc ggcttcgtgc gcgcccagat cggtgcgcgg    2880
gaggggcggg atctcgcggc tgggctctc gccggcgtgg atccggcccg gatctcgcgg     2940
ggaatggggc tctcggatgt agatctgcga tccgccgttg ttgggggaga tgatgggggg    3000
tttaaaattt ccgccgtgct aaacaagatc aggaagaggg gaaaagggca ctatggttta   3060
tattttata tatttctgct gcttcgtcag gcttagatgt gctagatctt tctttcttct    3120
ttttgtgggt agaatttgaa tccctcagca ttgttcatcg gtagttttc ttttcatgat    3180
ttgtgacaaa tgcagcctcg tgcggagctt ttttgtaggt agaagtgatc aaccatggac   3240
aacaacccaa acatcaacga gtgcatcccg tacaactgcc tcagcaaccc tgaggtcgag   3300
gtgctcggcg gtgagcgcat cgagaccggt tacaccccca tcgacatctc cctctccctc   3360
acgcagttcc tgctcagcga gttcgtgcca ggcgctggct tcgtcctggg cctcgtggac   3420
atcatctggg gcatctttgg cccctcccag tgggacgcct tcctggtgca aatcgagcag   3480
ctcatcaacc agaggatcga ggagttcgcc aggaaccagg ccatcagccg cctggagggc   3540
ctcagcaacc tctaccaaat ctacgcgag agcttccgg agtgggaggc cgacccact      3600
aacccagctc tccgcgagga gatgcgcatc cagttcaacg acatgaacag cgccctgacc   3660
accgccatcc cactcttcgc cgtccagaac taccaagtcc cgctcctgtc cgtgtacgtc   3720
caggccgcca acctgcacct cagcgtgctg agggacgtca gcgtgtttgg ccagaggtgg   3780
ggcttcgacg ccgccaccat caacagccgc tacaacgacc tcaccaggct gatcggcaac   3840
tacaccgacc acgctgtccg ctggtacaac actggcctgg agcgcgtctg ggcctgat    3900
tctagagact ggattcgcta caaccagttc aggcgcgagc tgaccctcac cgtcctggac   3960
attgtgtccc tcttcccgaa ctacgactcc cgcacctacc cgatccgcac cgtgtcccaa   4020
ctgacccgcg aaatctacac caaccccgtc ctggagaact tcgacggtag cttcagggag   4080
agcgcccagg gcatcgaggg ctccatcagg agcccacacc tgatggacat cctcaacagc   4140
atcactatct acaccgatgc ccaccgcgg gagtactact ggtccggcca ccagatcatg    4200
gcctcccgg tcggcttcag cggccccgag tttaccttc ctctctacgg cacgatgggc     4260
aacgccgctc cacaacaacg catcgtcgct cagctgggc agggcgtcta ccgcaccctg    4320
agctccaccc tgtaccgcag gcccttcaac atcggtatca acaaccagca gctgtccgtc   4380
ctggatggca ctgagttcgc ctacggcacc tcctccaacc tgccctccgc tgtctaccgc   4440
aagagcggca cggtggattc cctggacgag atcccaccac agaacaacaa tgtgcccccc   4500
aggcagggtt tttcccacag gctcagccac gtgtccatgt tccgctccgg cttcagcaac   4560
tcgtccgtga gcatcatcag agctcctatg ttctcttgga tacaccgtag tgctgagttc   4620
aacaacatca ttgcatccga cagcattact caaatacccc tggtgaaagc acatacactt   4680
cagtcaggta ctactgttgt cagaggtcca gggtttacag gaggagacat tcttcgtcgc   4740
acaagtggag gacccttgc ttacactatt gttaacatca atggccaatt gccccaaagg     4800
tatcgtgcaa gaatccgcta tgcctctact acaaatctca ggatctacgt gactgttgca   4860
ggtgaaagga tctttgctgg tcagttcaac aagactatgg ataccggtga ccctttgaca   4920
ttccaatctt ttagctacgc aactatcaac acagctttta cattcccaat gagccagagt   4980
agcttcacag taggtgctga cactttcagc tcagggaatg aagtttacat cgacaggttt   5040
gaattgattc cagttactgc aaccctcgag gctgagtaca accttgagag agcccagaag   5100
gctgtgaacg ccctctttac ctccaccaat cagcttggct tgaaaactaa cgttactgac   5160
tatcacattg accaagtgtc caacttggtc acctaccta gcgatgagtt ctgcctcgac    5220
gagaagcgtg aactctccga gaaagttaaa cacgccaagc gtctcagcga cgagaggaat   5280
ctcttgcaag actccaactt caaagacatc aacaggcagc cagaacgtgg ttggggtgga   5340
agcaccggga tcaccatcca aggaggcgac gatgtgttca aggagaacta cgtcaccctc   5400
tccgaacttt tcgacgagtg ctaccctacc tacttgtacc agaagatcga tgagtccaaa   5460
ctcaaagcct tcaccaggta tcaacttaga ggctacatcg aagacagcca agaccttgaa   5520
atctactcga tcaggtacaa tgccaagcac cagaccgtga atgtcccagg tactggttcc   5580
ctctggccac tttctgccca atctcccatt gggaagtgtg gagagcctaa cagatgcgct   5640
ccacaccttg agtggaatcc tgacttggac tgctcctgca gggatggcga gaagtgtgcc   5700
caccattctc atcacttctc cttggacatc gatgtgggat gtactgacct gaatgaggac   5760
ctcggagtct gggtcatctt caagatcaag acccaagacg gacacgcaag acttggcaac   5820
cttgagtttc tcgaagagaa accattggtc ggtgaagctc tcgctcgtgt gaagagagca   5880
gagaagaagt ggagggacaa acgtgagaaa ctcgaatggg aaactaacat cgtttacaag   5940
gaggccaaag agtccgtgga tgctttgttc gtgaactccc aatatgatca gttgcaagcc   6000
gacaccaaca tcgccatgat ccacgccgca gacaaacgtg tgcacagcat tcgtgaggct   6060
tacttgcctg agttgtccgt gatccctggt gtgaacgctg ccatcttcga ggaacttgag   6120
ggacgtatct ttaccgcatt ctccttgtac gatgccagaa acgtcatcaa gaacggtgac   6180
ttcaacaatg gcctcagctg ctggaatgtg aaggtcatg tggacgtgga ggaacagaac    6240
aatcagcgtt ccgtcctggt tgtgcctgag tgggaagctg aagtgtccca agaggttaga   6300
gtctgtccag gtagaggcta cattctccgt gtgaccgctt acaaggaggg atacggtgga   6360
ggttgcgtga ccatccacga gatcgagaac aacaccgacg agcttaagtt ctccaactgc   6420
gtcgaggaag aaatctatcc caacaacacc gttacttgca acgactacac tgtgaatcag   6480
gaagagtacg gaggtgccta cactagccgt aacagaggtt acaacgaagc tccttccgtt   6540
cctgctgact atgcctccgt gtacgaggag aaatcctaca cgattggcag acgtgagaac   6600
ccttgcgagt tcaacagagg ttacagggac tacacaccac ttccagttgg ctatgttacc   6660
aaggagcttg agtactttcc tgagaccgac aaagtgtgga tcgagatcgg tgaaaccgag   6720
ggaaccttca tcgtggacag cgtggagctt ctcttgatgg aggaataatg agatctatcg   6780
attctagaag gcctgaattc tgcatgcgtt tggacgtatg ctcattcagg ttggagccaa   6840
tttggttgat gtgtgtgcga gttcttgcga gtctgatgga acatctctgt attgtgtttc   6900
tttccccagt gtttctgtca cttgtgtaat cggctaatcg ccaacagatt cggcgatgaa   6960
taaatgagaa ataaattgtt ctgattttga gtgcaaaaaa aaaggaatta gatctgtgtg   7020
tgtttttttgg atccccgggg cggccgcgtt aacaagcttg agctcaggat ttagcagcat   7080
tccagattgg gttcaatcaa caaggtacga gccatatcac tttattcaaa ttggtatcgc    7140
caaaaccaag aaggaactcc catcctcaaa ggttttgtag gaagaattct cagtccaaag    7200
cctcaacaag gtcagggtac agagtctcca aaccattagc caaaagctac aggagatcaa   7260
tgaagaatct tcaatcaaag taaactactg ttccagcaca tgcatcatgg tcagtaagtt   7320
tcagaaaaag acatccaccg aagacttaaa gttagtgggc atctttgaaa gtaatccttgt 7380
caacatcgag cagctggctt gtggggacca gacaaaaaag gaatggtgca gaattgttag   7440
gcgcacctac caaaagcatc tttgccttta ttgcaaagat aaagcagatt cctctagtac   7500
```

-continued

```
aagtggggaa caaaataacg tggaaaagag ctgtcctgac agcccactca ctaatgcgta  7560
tgacgaacgc agtgacgacc acaaaagaat tccctctata taagaaggca ttcattccca  7620
tttgaaggat catcagatac tcaaccaatc cttctaggat ctaccgtctt cggtacgcgc  7680
tcactccgcc ctctgccttt gttactgcca cgtttctctg aatgctctct tgtgtggtga  7740
ttgctgagag tggtttagct ggatctagaa ttacactctg aaatcgtgtt ctgcctgtgc  7800
tgattacttg ccgtcctttg tagcagcaaa atatagggac atggtagtac gaaacgaaga  7860
tagaacctac acagcaatac gagaaatgtg taatttggtg cttagcggta tttatttaag  7920
cacatgttgg tgttataggg cacttggatt cagaagtttg ctgttaattt aggcacaggc  7980
ttcatactac atgggtcaat agtataggga ttcatattat aggcgatact ataataattt  8040
gttcgtctgc agagcttatt atttgccaaa attagatatt cctattctgt ttttgtttgt  8100
gtgctgttaa attgttaacg cctgaaggaa taaatataaa tgacgaaatt ttgatgttta  8160
tctctgctcc tttattgtga ccataagtca agatcagatg cacttgtttt aaatattgtt  8220
gtctgaagaa ataagtactg acagtatttt gatgcattga tctgcttgtt tgttgtaaca  8280
aaatttaaaa ataaagagtt tccttttgt tgctctcctt acctcctgat ggtatctagt  8340
atctaccaac tgacactata ttgcttctct ttacatacgt atcttgctcg atgccttctc  8400
cctagtgttg accagtgtta ctcacatagt ctttgctcat ttcattgtaa tgcagatacc  8460
aagcggcctc tagaggatca gcatggcgcc caccgtgatg atggcctcgt cggccaccgc  8520
cgtcgctccg ttccagggc tcaagtccac cgccagcctc cccgtcgccc gccgctcctc  8580
cagaagcctc ggcaacgtca gcaacgcgcg aaggatccgg tgcatgcagg taacaaatgc  8640
atcctagcta gtagttcttt gcattgcagc agctgcagct agcgagttag taataggaag  8700
ggaactgatg atccatgcat ggactgatgt gtgttgccca tcccatccca tttcccaacc  8760
ccaaacgaac caaaacacac gtactacgtg caggtgtggc cggcctacgg caacaagaag  8820
ttcgagacgc tgtcgtacct gccgccgctg tcgaccggcg ggcgcatccg ctgcatgcag  8880
gccatggaca actccgtcct gaactctggt cgcaccacca tctgcgacgc ctacaacgtc  8940
gcggcgcatg atccattcag cttccagcac aagagcctcg acactgttca gaaggagtgg  9000
acggagtgga agaagaacaa ccacagcctg tacctggacc ccatcgtcgg cacggtggcc  9060
agcttccttc tcaagaaggt cggctctctc gtcgggaagc gcatcctctc ggaactccgc  9120
aacctgatct ttccatctgg ctccaccaac ctcatgcaag acatcctcag ggagaccgag  9180
aagtttctca accagcgcct caacactgat acccttgctc cgtcaacgc tgagctgacg  9240
ggtctgcaag caaacgtgga ggagttcaac cgccaagtgg acaacttcct caaccccaac  9300
cgcaatgcgg tgcctctgtc catcacttct tccgtgaaca ccatgcaaca actgttcctc  9360
aaccgcttgc ctcagttcca gatgcaaggc taccagctgc tcctgctgcc actctttgct  9420
caggctgcca acctgcacct ctccttcatt cgtgacgtga tcctcaacgc tgacgagtgg  9480
ggcatctctg cagccacgct gaggacctac cgcgactacc tgaagaacta caccagggac  9540
tactccaact attgcatcaa cacctaccag tcggccttca agggcctcaa tacgaggctt  9600
cacgacatgc tggagttcag gacctacatg ttcctgaacg tgttcgagta cgtcagcatc  9660
tggtcgctct tcaagtacca gagcctgctg gtgtccagcg gcgccaacct ctacgccagc  9720
ggctctggtc cccaacaaac tcagagcttc accagcagg actggccatt cctgtattcg  9780
ttgttccaag tcaactccaa ctacgtcctc aacggcttcc ctggtgctcg cctctccaac  9840
accttcccca acattgttgg cctccccggc tccaccacaa ctcatgctct cttgctgcc  9900
agagtgaact actccggcgg catctcgagc ggcgacattg tgcatcgcc gttcaaccag  9960
aacttcaact gctccacctt cctgccgccg ctgctcaccc cgttcgtgag gtcctggctc  10020
gacagcgcct ccgaccgcga gggcgtggcc accgtcacca actggcaaac cgagtccttc  10080
gagaccaccc ttggcctccg gagcggcgcc ttcacggcgc gtggaaattc taactacttc  10140
cccgactact tcatcaggaa catctctggt gttcctctcg tcgtccgcaa cgaggacctc  10200
cgccgtccac tgcactacaa cgagatcagg aacatcgcct ctccgtccgg gacgcccgga  10260
ggtgcaaggg cgtacatggt gagcgtccat aacaggaaga acaacatcca cgctgtgcat  10320
gagaacggct ccatgatcca cctggcgccc aatgattaca ccggcttcac catctctcca  10380
atccacgcca cccaagtgaa caaccagaca cgcaccttca tctccgagaa gttcggcaac  10440
cagggcgact cccctgaggtt cgagcagaac aacaccaccg ccaggtacac cctgcgcggc  10500
aacggcaaca gctacaacct gtacctgcgc gtcacgttca ttggcaactc caccatcagg  10560
gtcaccatca acgggagggt gtacacagcc accaatgtga acacgacgac caacaatgat  10620
ggcgtcaacg acaacggcgc ccgcttcagc gacatcaaca ttggcaacgt ggtgccagc  10680
agcaactccg acgtccgct ggacatcaac gtgaccctga actctggcac ccagttcgac  10740
ctcatgaaca tcatgctggt gccaactaac atctcgccgc tgtactgata ggagctctga  10800
tccccatggg aattcccgat cgttcaaaca tttggcaata aagttctta agattgaatc  10860
ctgttgccgg tcttcgcatg attatcatat aatttctgtt gaattacgtt aagcatgtaa  10920
taattaacat gtaatgcatg acgttattta tgagatgggc ttttatgatt agagtcccgc  10980
aattatacat ttaatacgcg atagaaaaca aaatatagcg cgcaaactag gataaattat  11040
cgcgcgcggt gtcatctatg ttactagatc ggggatatcc ccggggcggc cgcggggaat  11100
tcggtaccaa gctttggcgc gccaaatcgt gaagttctc atctaagccc ccattttggac  11160
gtgaatgtag acacgtcgaa ataaagattt ccgaattaga ataatttgtt tattgctttc  11220
gcctataaat acgacggatc gtaatttgtc gttttatcaa aatgtacttt cattttataa  11280
taacgctgcg gacatctaca ttttgaatt gaaaaaaat tggtaattac tctttctttt  11340
tctccatatt gaccatcata ctcattgcat ccccggaaat tatgtttttt taaaaaccac  11400
ggtattatag ataccgtgtt atttttgag tattggaaat ttcatttcaa cccaaagttt  11460
cttcatggca catctagctt ttgcctaata ccatgtaggg ctacatctta aaaatctata  11520
ctactatatt aaagctgcag gggtagcctg tctccacctg gttctgcctc gagccaatct  11580
aaaccgtcca tctatatcca tcaaatcagc accgtccgct ccgtgcgcac ctcctctccc  11640
gctattcagt tgcatacttg cagcaggttc tccctcctca ccatttcctc tgcctcctct  11700
ctcgctcact ggtcagattc atcctgcctc tccccatgc gctccctccc catgcccgt  11760
ctcgcactat cgccacacct caccgcgggg agacgaagac ggtggacgca tcctcacctc  11820
ctccgctagt tgtcgctctt ccatcctctt caacaacttc tacataggga gaggcggttc  11880
cgggtcccga cgccgcgct tctccccctcc ccatggagga cgagaacatc gacctcggcg  11940
gcggggggcga tgcctccgct ctgcatagag gaggggttgta gtggcaagca gcaatgccaa  12000
caccgaggcg ggccaagact aggcaacaat aggacggcac gccggttgt cagcgaggtg  12060
gcggcatcgt gtgccgctac cgaacaacat ctccggcgct ggagtcggtg agttactgcg  12120
ccacccggac gccctcaatg cactgatatc taccggtct ccatcgccgc ccttcctccc  12180
ttccctctcc ctgtgcctcc ctctcttgcc ctctcccttc caactgctcc cgccccagcc  12240
```

```
ctagcccaac cacctcccgc gcagggtcac caa                          12273
```

SEQ ID NO: 30          moltype = DNA   length = 12272
FEATURE                Location/Qualifiers
source                 1..12272
                       mol_type = other DNA
                       organism = synthetic construct
SEQUENCE: 30

```
aatatttaaa aatggaagta atactatatt aaaatgattc atgtggaact cctgcgcttc   60
tttttgaagt ttcaaaaggg agctttcagg gtcgcttaga gtttgtttgg ttggaaatac  120
aagcgaaaag agagctaatg aggggggacat ccatattttc tatggtgttt gaataagagt  180
cacgcgggaa taagatgaac accgaaacaa ttttttttgta gctacgtggt tccaaaaaat  240
cgagtagacg gtgtcgcttc cacctcatac tacttcaacc tcaaaccaca catccttacg  300
cgcccgccgg tgtctccgtc gtctcaagtt ctcaacatac ctacacatgt aaccactacc  360
ggtctttgtc atgtttcgaa agaagattac aggtcctcta aagagagga cgcggggtgg  420
cgagaaagct ggggaagaaa aaggctagta catatgattg gtctgtgaac ctgtgaggtg  480
ggtaggtagg taggtggaga ttttttgttaa ctggtgttgt tgacggactc gaacgggggcc  540
gggcgtgtgg tgtggctagc tgtggtggtt tgctcgccag ccagccagcc acacatcagc  600
gagcatgcag agcttaagca tgtatgtacg gatcggcttg cttagcggtt aagggtgtgt  660
ttggtttggc ttttggcttt ggcttttgcc cctaaaagc caaaagccaa ccaagggtgt  720
atttggtttg acttttggct tttggctttt gtcccctaaa agccaaaagc caaacaaagg  780
gttagatcta ggaagcagct tttttctaaaa gctggctttc tcacagtgca aatctgaaag  840
caccccctgaa cctgctttta gtggcttttc gaatggaact gtgaaaacat atatcgaaga  900
acttttaacg acttttagtg gtttccacca aacagtttag cttttttaacg gcttacagcc  960
tacaacagct ttttccacag ctcacagccc acagcaactt ttttcacagc cacagcccaa 1020
ccaaacagac cccaaagggc tgaatccagg aagcagcttt ttctaaaagc cgactttctc 1080
gtagtgtaaa actgaaaaca ccctggacc tgcttttagt ggcttttgga tggaactgtg 1140
aaaacatata tcgaagaact tttaacgact tttagtggtt tccaccaaac gatttctagc 1200
ttttttaacag cacacagcct acaacagctt ttttcacagc tcacagccca caacaacttt 1260
ttctcagcc acaacccaac caaacggacc ctaaggcggc cgagcgagcg caaagcgtcg 1320
tcagctttga ttgccatgcc atctcctgct ccacttgtct ctctggccgt cgtcagccac 1380
catccaacaa ggccggtgct actggcggct cctaggtaga cgacgacgac gacgacacct 1440
ccaccgttcg ccgccgtcca ctcaccaatc aacacgaac gcccaaaaca cacacacacg 1500
cacgctgggg aggaaaaaa aggcagagac atatgcgtgc gtcgctgcat tattgtacgc 1560
gatccaatgg catctctctc actctctctc ctcccttttat taatctggta ctggctagct 1620
ggtccggcga caccgacgtg tcagctccgt cgcgcgcgtc cgtccgtccg ctggagcgga 1680
cacggaccgc ggcgtctgtc gatcgccggc tcgccagc gcagctacct agcacgctca 1740
cgcatgctac actgcctaca cgcacacggc cggcccaaaa gcgttccctg ccgcctgccg 1800
gccggctttt ttattattat tggaacatga ggctatttct cctcccacac ggctacgac 1860
gtgagcacga gtactgggat ccccggatcc gcccctctg tccctgctgc tactccagcc 1920
actgaaatgt tgtcagatga aacagcagag ccgatctccg cacggaaacc catgcacggc 1980
cattcaaatt caggtgccca cgtacgtcag ggtgctgctg ctactactat caagccaata 2040
aaaggatggt aatgagtatg atggtcaata tggtgaaaaa gaaagagtaa 2100
ttaccaattt tttttcaatt caaaaatgta gatgtccgca gcgttattat aaaatgaaag 2160
tacattttga taaaacgaca aattacgatc cgtcgtattt ataggcgaaa gcaataaaca 2220
aattattcta attcggaaat cttttatttcg acgtgtctac attcacgtcc aaatgggggc 2280
ttagatgaga aacttcacga tttggcgcgc caaagcttgg tcgagtggaa gctagctttc 2340
cgatcctacc tgtcacttca tcaaaaggac agtagaaaag gaaggtggct cctacaaatg 2400
ccatcattgc gataaaggaa aggccatcgt tgaagatgcc tctgccgaca gtggtcccaa 2460
agatggaccc ccaccacga ggagcatcgt ggaaaaagaa gacgttccaa ccacgtcttc 2520
aaagcaagtg gattgatgtg atatctccac tgacgtaagg gatgacgcac aatcccacta 2580
tccttcgcaa gacccttcct ctatataagg aagttcattt catttggaga ggacacgctg 2640
acaagctgac tctagcagat cctctagaac catcttccac acactcaagc cacactattg 2700
gagaacacac agggacaaca caccataaga tccaagggag gcctccgccg ccgcggtaa 2760
ccacccgcc cctctcctct ttctttctcc gtttttttt ccgtctccgt ctcgatcttt 2820
ggccttggta gtttgggtgg gcgagaggcg gcttcgtgcg cgcccagatc ggtgcgcggg 2880
aggggcggga tctcgcggct ggggctctcg ccggcgtgga tccggccggg atctcgcggg 2940
gaatggggct ctcggatgta gatctgcgat ccgccgttgt tgggggagat gatgggggt 3000
ttaaaatttc cgccgtgcta aacaagatca ggaagagggg aaaagggcac tatggttttat 3060
atttttatat atttctgctg cttcgtcagg cttagatgtg ctagatcttt cttctctctt 3120
tttgtgggta gaatttgaat ccctcagcat tgttcatcgg tagttttttct tttcatgatt 3180
tgtgacaaat gcagcctcgt gcggagcttt tttgtaggta gaagtgatca accatggaca 3240
acaacccaaa catcaacgag tgcatcccgt acaactgcct cagcaaccct gaggtcgagg 3300
tgctcggcgg tgagcgcatc gagaccggtt acaccccccat ctctccctca 3360
cgcagttcct gctcagcgag ttcgtgccag gcgctggctt cgtcctgggc ctcgtggaca 3420
tcatctgggg catctttggc cctctcccagt gggacgcctt cctggtgcaa atcgagcagc 3480
tcatcaacca gaggatcgag gagttcgcca ggaaccaggc catcagccgc ctggagggcc 3540
tcagcaacct taccaaatc tacgctgaga gcttccgcga gtgggaggcc gacccactga 3600
acccagctct ccgcgaggag atgcgcatcc agttcaacga tgaacagc gcctgactga 3660
ccgccatccc actcttcgcc gtccagaact accaagtccc gctcctgtcc gtgtacgtcc 3720
aggccgccaa cctgcacctc agcgtgctga gggacgtcag cgtgttggc cagaggtggg 3780
gcttcgacgc cgccaccatc aacagccgct acaacgacct caccaggctg atcggcaact 3840
acaccgacca cgctgtccgc tggtacaaca ctggcctgga gcgcgtctgg ggcccctgatt 3900
ctagaggctac aactagttca ggcggcgact gccctacct gtcctggaca 3960
ttgtgtccct cttcccgaac tacgactccc gcacctaccc gatccgcacc gtgtccaac 4020
tgacccgcga aatctacacc aaccccgtcc tggagaactt cgacggtagc ttcagggca 4080
gcgcccaggg catcgagggc tccatcagga gcccacacct gatggacatc ctcaacagca 4140
tcactatcta caccgatgcc caccgcgcg agtactactg gtccggccac cagatcatgg 4200
cctccccggt cggcttcagc ggccccgagt ttacccttcc tctctacggc acgatgggca 4260
```

```
acgccgctcc acaacaacgc atcgtcgctc agctgggcca gggcgtctac cgcaccctga 4320
gctccaccct gtaccgcagg cccttcaaca tcggtatcaa caaccagcag ctgtccgtcc 4380
tggatggcac tgagttcgcc tacggcacct cctccaacct gccctccgct gtctaccgca 4440
agagcggcac ggtggattcc ctggacgaga tcccaccaca gaacaacaat gtgccccca  4500
ggcagggttt ttcccacagg ctcagccacg tgtccatgtt ccgctccggc ttcagcaact 4560
cgtccgtgag catcatcaga gctcctatgt tctcttggat acaccgtagt gctgagttca 4620
acaacatcat tgcatccgac agcattactc aaataccctt ggtgaaagca catacacttc 4680
agtcaggtac tactgttgtc agaggtccag ggtttacagg aggagacatt cttcgtcgca 4740
caagtggagg acccttgct tacactattg ttaacatcaa tggccaattg ccccaaaggt  4800
atcgtgcaag aatccgctat gcctctacta caaatctcag gatctacgtg actgttgcag 4860
gtgaaaggat ctttgctggt cagttcaaca agactatgga taccggtgac cctttgacat 4920
tccaatcttt tagctacgca actatcaaca cagcttttac attcccaatg agccagagta 4980
gcttcacagt aggtgctgac acttcagct cagggaatga agtttacatc gacaggtttg  5040
aattgattcc agttactgca accctgcagg ctgagtacaa ccttgagaga gcccagaagg 5100
ctgtgaacgc cctctttacc tccaccaatc agcttggctt gaaaactaac gttactgact 5160
atcacattga ccaagtgtcc aacttggtca cctaccttag cgatgagttc tgcctcgacg 5220
agaagcgtga actctccgag aaagttaaac acgccaagcg tctcagcgac gagaggaatc 5280
tcttgcaaga ctccaacttc aaagacatca acaggcagcg aaacgtggt tggggtggaa  5340
gcaccgggat caccatccaa ggaggcgacg atgtgttcaa ggagaactac gtcaccctct 5400
ccggaacttt cgacgagtgc taccctacct acttgtacca gaagatcgat gagtccaaac 5460
tcaaagcctt caccaggtat caacttagag gctacatcga agacagccaa gaccttgaaa 5520
tctactcgat caggtacaat gccaagcacg agaccgtgaa tgtcccaggt actgttccc  5580
tctggccact ttctgcccaa tctcccattg ggaagtgtgg agagcctaac agatgcgctc 5640
cacaccttga gtggaatcct gacttggact gctcctgcag ggatggcgag aagtgtgccc 5700
accattctca tcacttctcc ttggacatcg atgtgggatg tactgacctg aatgaggacc 5760
tcggagtctg ggtcatcttc aagatcaaga cccaagacgg acacgcaaga cttggcaacc 5820
ttgagtttct cgaagagaaa ccattggtcg gtgaagctct cgctcgtgtg aagagagcag 5880
agaagaagtg gagggacaaa cgtgagaaac tcgaatggga aactaacatc gtttacaagg 5940
aggccaaaga gtccgtggat gctttgttcg tgaactccca atatgatcag ttgcaagccg 6000
acaccaacat cgccatgatc cacgccgcag acaaacgtgt gcacagcatc cgtgaggctt 6060
acttgcctga gttgtccgtg atccctggtg tgaacgctgc catcttcgag gaacttgagg 6120
gacgtatctt taccgcattc tccttgtacg atgccagaaa cgtcatcaag aacggtgact 6180
tcaacaatgg cctcagctgc tggaatgtga aggtcatgt ggacgtggag aacagaaca  6240
atcagcgttc cgtcctggtt gtgcctgagt gggaagctga agtgtcccaa gaggtagag  6300
tctgtccagg tagaggctac attctccgtg tgaccgctta caaggaggga tacggtagga 6360
gttgcgtgac catccacgag atcgagaaca acaccgacga gcttaagttc tccaactgcg 6420
tcgaggaaga aatctatccc aacaacaccg ttacttgcaa cgactacact gtgaatcagg 6480
aagagtacgg aggtgcctac actagccgta acagaggtta caacgaagct ccttccgttc 6540
ctgctgacta tgcctccgtg tacgaggaga aatcctacac agatgccgag cgtgagaacc 6600
cttgcgagtt caacagaggt tacagggact acacaccact tccagttggc tatgttacca 6660
aggagcttga gtactttcct gagaccgaca agtgtggat cgagatcggt gaaaccgagg  6720
gaaccttcat cgtggacagc gtggagcttc tcttgatgga ggaataatga gatctatcga 6780
ttctagaagg cctgaattct gcatgcgttt ggacttgaca tcattcaggt tggagccaat 6840
ttggttgatg tgtgtgcgag ttcttgcgag tctgatgaga catctctgta ttgtgtttct 6900
ttccccagtg ttttctgtac ttgtgtaatc ggctaatcgc caacagattc ggcgatgaat 6960
aaatgagaaa taaattgttc tgattttgag tgcaaaaaaa aaggaattag atctgtgtgt 7020
gttttttgga tccccggggc ggccgcgtta acaagcttgg agctcaggatt tagcagcatt 7080
ccagattggg ttcaatcaac aaggtacgag ccatatcact ttattcaaat tggtatcgcc 7140
aaaaccaaga aggaactccc atcctcaaag gtttgtaagg aagaattctc agtccaaagc 7200
ctcaacaagg tcagggtaca gagtctccaa accattagcc aaaagctaca ggagatcaat 7260
gaagaatctt caatcaaagt aaactactgt tccagcaata gcatcatggt cagtaagttt 7320
cagaaaaaga catccaccga agacttaaag ttagtgggca tctttgaaag taatcttgtc 7380
aacatcgagc agctggcttg tggggaccag acaaaaaagg aatggtgcag aattgttagg 7440
cgcacctacc aaaagcatct ttgcctttat tgcaaagata agcagattc ctctagtaca  7500
agtggggaac aaaataacgt ggaaaagagc tgtcctgaca gcccactcac taatgcgtat 7560
gacgaacgca gtgacgacca caaagaattc ccctctatat aagaaggcat tcattcccat 7620
ttgaaggatc atcagatact caaccaatcc ttctaggatc taccgtcttc ggtacgcgct 7680
cactccgccc tctgcctttg ttactgccac gtttctctga atgctctctt gtgtggtgat 7740
tgctgagagt ggtttagctg gatctagaat tacactctga aatcgtgttc tgcctgtgct 7800
gattacttgc cgtcctttgt agcagcaaaa tataggagaca tggtagtacg aaacaagaat 7860
agaacctaca cagcaaatacg agaaatgtgt aatttggtgc ttagcggtat ttatttaagc 7920
acatgttggt gttatagggc acttggattc agaagtttgc tgttaattta ggcacaggct 7980
tcatactaca tgggtcaata gtataggat tcatattata ggcgatacta taataatttg  8040
ttcgtctgca gagcttatta tttgccaaaa ttagatattc ctattctgtt tttgtttctg 8100
tgctgttaaa ttgttaacgc ctgaaggaat aaatataaat gacgaaattt tgatgtttat 8160
ctctgctcct ttattgtgac cataagtcaa gatcagatgc acttgtttta aatattgttg 8220
tctgaagaaa taagtactga cagtattttg atgcattgat ctgcttgttt gttgtaacaa 8280
aatttaaaaa taaagagttt ccttttgtt gctctcctta cctcctgatg gtatctagta 8340
tctaccaact gacactatat tgcttctctt tacatacgtg tcttgctcga tgccttctct 8400
ctagtgttga ccagtgttac tcacatagtc tttgctcatt tcattgtaat gcagatacca 8460
agcggcctct agaggatcag catggcgccc accgtgatga tggcctcgtc ggccaccgcc 8520
gtcgctccgt tccaggggct caagtccacc gccagcctcc ccgtgcccg ccgctcctcc  8580
agaagcctcg gcaacgtcag caacggcgga aggatccggt gcatgcaggt aacaaatgca 8640
tcctagctag tagttctttg cattgcagca gctgcagcta ggcgagttagt aataggaagg 8700
gaactgatga tccatgcatg gactgatgtg tgttgcccat cccatcccat ttcccaaccc 8760
caaacgaacc aaaacacacg tactacgtgc aggtgtggcc ggcctacggc aacaagaagt 8820
tcgagacgct gtcgtacctg ccgccgctgt cgaccggcgg gcgcatccgc tgcatgcagg 8880
ccatggacaa ctccgtcctg aactctggtc gcaccaccat ctgcgacgcc tacaacgtcg 8940
cggcgcatga tccattcagc ttccagcaca agagcctcga cactgttcag aaggagtgga 9000
```

```
cggagtggaa gaagaacaac cacagcctgt acctggaccc catcgtcggc acggtggcca  9060
gcttccttct caagaaggtc ggctctctcg tcgggaagcg catcctctcg gaactccgca  9120
acctgatctt tccatctggc tccaccaacc tcatgcaaga catcctcagg gagaccgaga  9180
agtttctcaa ccagcgcctc aacactgata cccttgctcg cgtcaacgct gagctgacgg  9240
gtctgcaagc aaacgtggag gagttcaacc gccaagtgca caacttcctc aaccccaacc  9300
gcaatgcggt gcctctgtcc atcacttctt ccgtgaacac catgcaacaa ctgttcctca  9360
accgcttgcc tcagttccag atgcaaggct accagctgct cctgctgcca ctcttttgctc  9420
aggctgccaa cctgcacctc tccttcattc gtgacgtgat cctcaacgct gacgagtggg  9480
gcatctctgc agccacgctg aggacctacc gcgactacct gaagaactac accagggact  9540
actccaacta ttgcatcaac acctaccagt cggccttcaa gggcctcaat acgaaggcttc  9600
acgacatgct ggagttcagg acctacatgt tcctgaacgt gttcgagtac gtcagcatct  9660
ggtcgctctt caagtaccag agcctgctgg tgtccagcgg cgccaacctc tacgccagcg  9720
gctctggtcc ccaacaaact cagagcttca ccagccagga ctggccattc ctgtattcgt  9780
tgttccaagt caactccaac tacgtcctca acggcttctc tggtgctcgc ctctccaaca  9840
ccttccccaa cattgttggc ctccccggct ccaccacaac tcatgctctg cttgctgcca  9900
gagtgaacta ctccggcggc atctcgagcg gcgacattgg tgcatcgccg ttcaaccaga  9960
acttcaactg ctccaccttc ctgccgccgc tgctcacccc gttcgtgagg tcctggctcg 10020
acagcggctc cgaccgcgag ggcgtggcca ccgtcaccaa ctggcaaacc gagtccttcg 10080
agaccaccct tggcctccgg agcggcgcct tcacggcgcg tggaaattct aactacttcc 10140
ccgactactt catcaggaac atctctggtg ttcctctcgt cgtccgcaac gaggacctcc 10200
gccgtccact gcactacaac gagatcagga acatcgcctc tccgtccggg acgcccggag 10260
gtgcaagggc gtacatggtg agcgtccata acaggaagaa caacatccgc gctgtgcatg 10320
agaacgctc catgatccac ctggcgccca atgattacac cggcttcacc atctctccaa 10380
tccacgccac ccaagtgaac aaccagacac gcaccttcat ctccgagaag ttcggcaacc 10440
agggcgactc cctgaggttc gagcagaaca acaccaccgc caggtacacc ctgcgcggca 10500
acggcaacag ctacaacctg tacctgcgcg tcagctccat tggcaactcc accatcaggg 10560
tcaccatcaa cggggagggtg tacacagcca ccaatgtgaa cacgacgacc aacaatgatg 10620
gcgtcaacga caacggcgcc cgcttcagcg acatcaacat tggcaacgtg gtggccagca 10680
gcaactccga cgtcccgctg gacatcaacg tgaccctgaa ctctggcacc cagttcgacc 10740
tcatgaacat catgctggtg ccaactaaca tctcgccgct gtactgatag gagctctgat 10800
ccccatggga attcccgatc gttcaaacat ttggcaataa agtttcttaa gattgaatcc 10860
tgttgccggt cttgcgatga ttatcatata atttctgttg aattacgtta agcatgtaat 10920
aattaacatg taatgcatga cgttatttat gagatgggtt tttatgatta gagtcccgca 10980
attatacatt taatacgcga tagaaaacaa aatatagcgc gcaaactagg ataaattatc 11040
gcgcgcggtg tcatctatgt tactagatcg gggatatccc cggggcggcc gcggggaatt 11100
cggtaccaag ctttggcgcg ccaaatcgtg aagtttctca tctaagcccc catttggacg 11160
tgaatgtaga cacgtcgaaa taagattttc cgaattagaa taatttgttt attgctttcg 11220
cctataaata cgacggatcg taatttgtcg ttttatcaaa atgtactttc atttttataat 11280
aacgctgcgg acatctacat ttttgaattg aaaaaaaatt ggtaattact ctttcttttt 11340
ctccatattg accatcatac tcattgcatc cccggaaatt atgttttttt aaaaaccacg 11400
gtattataga taccgtgtta ttttttgagt attggaaatt tcatttcaac ccaaagtttc 11460
ttcatggcac atctagcttt tgcctaatac catgtagggc tacatcttaa aaatctatac 11520
tactatatta aagctgcagg ggtagcctgt ctccacctgg ttctgcctcg agccaatcta 11580
aaccgtccat ctatatccat caaatcagca ccgtccggtc cgtgcgcacc tcctctcccg 11640
ctattcagtt gcatacttgc agcaggttct ccctcctcac catttcctct gcctcctctc 11700
tcgctcactg gtcagattca tcctgcctct cccgcatgcg ctccctcccc atgcccgtc  11760
tcgcactatc gccacacctc accgcgggga gacgaagacg ggtgacgcat cctcacctcc 11820
tccgctagtt gtcgctcttc catcctcttc aacaacttct acataggggag aggcggttcc 11880
gcgtcccgac gccgccgctt ctcccctccc catggaggac gagaacatcg acctcggcgg 11940
cgggggcgat gcctccgctc tgcatagagg aggggttgtag tggcaagcag caatgccaac 12000
accgaggcgg gccaagacta ggcaacaata ggacggcacg cccggttgtc agcgaggtgg 12060
cggcatcgtg tgccgctacc gaacaacatc tccggcgctg gagtcggtga gttactgcgc 12120
caccggacg ccctcaatgc actgatatct accccggtctc catcgccgcc cttcctccct 12180
tccctctccc tgtgcctccc tctcttgccc tctcccttcc aactgctccc gccccagccc 12240
tagcccaacc acctccgcg cagggtcacc aa                               12272
```

SEQ ID NO: 31          moltype = DNA   length = 12271
FEATURE                Location/Qualifiers
source                 1..12271
                       mol_type = other DNA
                       organism = synthetic construct
SEQUENCE: 31

```
aatatttaaa aatggaagta atactatatt aaaatgattc atgtggaact cctgcgcttc   60
tttttgaagt ttcaaaaggg agctttcagg gtcgcttaga gtttgtttgg ttggaaatac  120
aagcgaaaag agagctaatg aggggagacat ccatattttc tatggtgttt gaataagagt  180
cacgcgggaa taagatgaac accgaaacaa tttttttgta gctacgtggt tccaaaaaat  240
cgagtagacg gtgtcgcttc cacctcatac tacttcaacc tcaaaccaca catccttacg  300
cgcccgccgg tgtctccgtc gtctcaagtt ctcaacatac ctacacatgt aaccactacc  360
ggtcttttgtc atgttttcgaa agaagattac aggtcctcta gaagagagaa cgcggggtgx  420
cgagaaagct ggggaagaaa aaggctagta catatgattg gtctgtgaac ctgtgaggtg  480
ggtaggtagg taggtggaga ttttttgttaa ctggtgttgt tgacggactc gaacggggcc  540
gggcgtgtgg tgtggctagc tgtggtggtt tgctcgccag ccagccagcc acacatcagc  600
gagcatgcag agcttaagca tgtatgtacg gatcggcttc cttagcggtt aagggtgtgt  660
ttggtttggc ttttggcttt ggcttttgcc ccctaaaagc caaaagcaaa caaaaggt   720
atttggtttg acttttggct tttgcttttt gtccctaaa agccaaaagc caaacaaagg t  780
gttagatcta ggaagcagct ttttctaaaa gctggctttc tcacagtgca aatctgaaag  840
cacccctgaa cctgctttta gtggcttttc gaatggaact gtgaaaacat atatcgaaga  900
acttttaacg acttttagtg gtttccacca aacagtttag cttttttaacg gcttacgcc   960
tacaacagct ttttccacag ctcacagccc acagcaactt ttttcacagc cacagcccaa 1020
```

```
ccaaacagac cccaaagggc tgaatccagg aagcagcttt ttctaaaagc cgactttctc    1080
gtagtgtaaa actgaaaaca cccctggacc tgcttttagt ggcttttgga tggaactgtg    1140
aaaacatata tcgaagaact tttaacgact tttagtggtt tccaccaaac gatttctagc    1200
tttttaacag cacacagcct acaacagctt ttttcacagc tcacagccca caacaacttt    1260
ttctacagcc acaacccaac caaacggacc ctaaggcggc cgagcgagcg caaagcgtcg    1320
tcagctttga ttgccatgcc atctcctgct ccacttgtct ctctggccgt cgtcagccac    1380
catccaacaa ggccggtgct actggcggct cctaggtaga cgacgacgac gacgacacct    1440
ccaccgttcg ccgccgtcca ctcaccaatc aacacggaac gcccaaaaca cacacacacg    1500
cacgctgggg agggaaaaaa aggcagagac atatgcgtgc gtcgctgcat tattgtacgc    1560
gatcgaatgg catctctctc actctctctc ctccctttat taatctggta ctggctagct    1620
ggtccggcga caccgacgtg tcagctccgt cgcgcgcgtc cgtccgtccg ctggagcgga    1680
cacggaccgc ggcgtctgtc gatcgccggc tcgccgcagc gcagctacct agcacgctca    1740
cgcatgctac actgcctaca cgcacacggc cggcccaaaa cgttccctg ccgcctgccg     1800
gccggcttt ttattattat tggaacatga ggctatttct cctcccacac gggctacgac     1860
gtgagcacga gtactgggat ccccggatcc gccctctctg tccctgctgc tactccagcc    1920
actgaaaatgt tgtcagatga aacagcagag ccgatctccg cacggaaacc catgcacggc   1980
cattcaaatt caggtgccca cgtacgtcag ggtgctgctg ctactactat caagccaata    2040
aaaggatggt aatgagtatg atggatatga tggtcaatat ggagaaaaag aaagagtaat    2100
taccaatttt ttttcaattc aaaaatgtag atgtccgcag cgttattata aaatgaaagt    2160
acattttgat aaaacgacaa attacgatcc gtcgtattta taggcgaaag caataaacaa    2220
attattctaa ttcggaaatc tttatttcga cgtgtctaca ttcacgtcca aatgggggct    2280
tagatgagaa acttcacgat ttgcgcgcgc aaagcttggt cgagtggaag ctagcttttcc   2340
gatcctacct gtcacttcat caaaaggaca gtagaaaagg aaggtggctc ctacaaatgc    2400
catcattgcg ataaaggaaa ggccatcgtt gaagatgcct ctgccgacag tggtcccaaa    2460
gatgaccccc cacccacgag gagcatcgtg gaaaaagaag acgttccaac cacgtcttca    2520
aagcaagtgg attgatgtga tatctccact gacgtaaggg atgacgcaca atcccactat    2580
ccttcgcaag acccttcctc tatataagga agttcatttc atttggagag gacacgctga    2640
caagctgact ctagcagatc ctctagaacc atcttccaca cactcaagcc acactattgg    2700
agaacacaca gggacaacac accataagat ccaagggagg cctccgccgc cgccggtaac    2760
cacccogccc ctctcctctt tcttttctccg tttttttttttc cgtctcggtc tcgatctttg  2820
gccttggtag tttgggtggg cgagaggcgg cttcgtgcgc gcccagatcg gtgcgcggga    2880
ggggcgggat ctcgcggctg gggctctcgc cggcgtggat ccggcccgga tctcgcgggg    2940
aatgggggctc tcggatgtag atctgcgatc cgccgttgtt gggggagatg atggggggtt    3000
taaaatttcc gccgtgctaa aacaagatcag gaagagggga aaagggcact atggtttata   3060
tttttatata tttctgctgc ttcgtcaggc ttagatgtgc tagatctttc ttttcttcttt    3120
ttgtgggtag aatttgaatc cctcagcatt gttcatcggt agttttttctt ttcatgatttt   3180
gtgacaaatg cagcctcgtg cggagctttt ttgtaggtag aagtgatcaa ccatggacaa    3240
caaccccaaac atcaacgagt gcatcccgta caactgcctc agcaaccctg aggtcgaggt    3300
gctcggcggt gagcgcatcg agaccggtta caccccccatc gacatctccc tctccctcac    3360
gcagttcctg ctcagcgagt tcgtgccagg cgctggcttc gtcctgggcc tcgtggacat    3420
catctgggc atctttggcc cctcccagtg ggacgccttc ctggtgcaaa tcgagcagct    3480
catcaaccag aggatcgagg agttcgccag gaaccaggcc atcagccgcc tggagggcct    3540
cagcaacctc taccaaatct acgctgagag cttccgcgag tgggaggccg accccactaa    3600
cccagctctc cgcgaggaga tgcgcatcca gttcaacgac atgaacacgc ccctgaccac    3660
cgccatccca ctcttcgccg tccagaacta ccaagtcccg ctcctgtccg tgtacgtcca    3720
ggccgccaac ctgcacctca gcgtgctgag ggacgtcagc gtgtttggcc agaggtgggg    3780
cttcgacgcc gccaccatca acagccgtca caacgacctc accaggctga tcggcaacta    3840
caccgaccac gctgtccgct ggtacaaacac tggcctggag cgcgtctggg gccctgattc    3900
tagagactgg attcgctaca accagttcag gcgcgagctg accctcaccg tcctggacat    3960
tgtgtccctc ttcccgaact acgactcccg cacctacccg atccgcaccg tgtcccaact    4020
gacccgcgaa atctacacca acccccgtcct ggagaacttc gacggtagct tcaggggcag   4080
cgcccagggc atcgagggct ccatcaggag cccacacctg atggacatcc tcaacagcat    4140
cactatctac accgatgccc accgcggcga gtactactgg tccggccacc agatcatggc    4200
ctccccggtc ggcttcagcg gccccgagtt taccttttcct ctctacgcca cgatgggcaa    4260
cgccgctcca caacaacgca tcgtcgctca gctgggccag ggcgtctacc gcaccctgag    4320
ctccaccctg taccgcaggc ccttcaacat cggtatcaac aaccagcagc tgtccgtcct    4380
ggatggcact gagttcgcct acggcacctc ctccaacctg ccctccgctg tctaccgcaa    4440
gagcggcacg gtggattccc tggacgagat cccaccacag aacaacaatg tgcccccccag   4500
gcagggtttt tcccacaggc tcagccacgt gtccatgttc cgctccggct tcagcaactc    4560
gtccgtgagc atcatcagag ctcctatgtt ctcttggata caccgtagtg ctgagttcaa    4620
caacatcatt gcatccgaca gcattactca aataccttg gtgaaagcac atacacttca     4680
gtcaggtact actgttgtca gaggtccagg gtttacagga ggagacattc ttcgtcgcac    4740
aagtggagga ccctttgctt acactattgt taacatcaat ggccaattgc cccaaaggta    4800
tcgtcaagta atccgctatg cctctactac aaatctcaga atctacgtga ctgttgcgga    4860
tgaaaggatc tttgctggtc agttcaacaa gactatggat accggtgacc ctttgacatt    4920
ccaatctttt agctacgcaa ctatcaacac agcttttaca ttcccaatga gccagagtag    4980
cttcacagta ggtgctgaca ctttcagctc agggaatgaa gtttacatcg acaggtttga    5040
attgattcca gttactgcaa cccctcgaggc tgagtacaac cttgagagag cccagaaggc    5100
tgtgaacgcc ctcctttacct ccaccaatca gcttggccta aaaactaacg ttactgacta   5160
tcacattgac caagtgtcca acttggtcac ctaccttagc gatgagttct gcctcgacga    5220
gaagcgtgaa ctctccgaga aagttaaaca cgccaagcgt ctcagcgacg agaggaatct    5280
cttgcaagac tccaacttca aagacatcaa caggcagcca gaacgtggtt ggggtggaag    5340
caccgggatc accatccaag gaggcgacga tgtgttcaag gagaactacg tcaccctctc    5400
cggaactttc gacgagtgct accctaccta cttgtaccag aagatcgatg agtccaaact    5460
caaagccttc accaggtatc aacttagagg ctacatcgaa gacagccaag acctttgaaat   5520
ctactcgatc aggtacaatg ccaagcacga gaccgtgaat gtcccaggta ctggttccct    5580
ctggccactt tctgcccaat ctcccattgg gaagtgtgga gagcctaaca gatgcgctcc    5640
acaccttgag tggaatcctg acttggactg ctcctgcagg gatggcgaga gtgtgcccaa    5700
ccattctcat cacttctcct tggacatcga tgtgggatgt actgacctga atgaggacct    5760
```

```
cggagtctgg gtcatcttca agatcaagac ccaagacgga cacgcaagac ttggcaacct  5820
tgagtttctc gaagagaaac cattggtcgg tgaagctctc gctcgtgtga agagagcaga  5880
gaagaagtgg agggacaaac gtgagaaact cgaatgggaa actaacatcg tttacaagga  5940
ggccaaagag tccgtggatg ctttgttcgt gaactcccaa tatgatcagt tgcaagccga  6000
caccaacatc gccatgatcc acgccgcaga caaacgtgtg cacagcattc gtgaggctta  6060
cttgcctgag ttgtccgtga tccctgtgtg gaacgctgcc atcttcgagg aacttgaggg  6120
acgtatcttt accgcattct ccttgtacga tgccagaaac gtcatcaaga acggtgactt  6180
caacaatggc ctcagctgct ggaatgtgaa aggtcatgtg gacgtggagg aacagaacaa  6240
tcagcgttcc gtcctggttg tgcctgagtg ggaagctgaa gtgtcccaag aggttagagt  6300
ctgtccaggt agaggctaca ttctccgtgt gaccgcttac aaggagggat acggtgaggg  6360
ttgcgtgacc atccacgaga tcgagaacaa caccgacgag cttaagttct ccaactgcgt  6420
cgaggaagaa atctatccca caacaccgt tacttgcaac gactcactg tgaatcagga  6480
agagtacgga ggtgcctaca ctagccgtaa cagaggttac aacgaagctc cttccgttcc  6540
tgctgactat gcctccgtgt acgaggagaa atcctcacaca gatgcgagc gtgagaaccc  6600
ttgcgagttc aacagaggtt acagggacta cacaccactt ccagttggct atgttaccaa  6660
ggagcttgag tactttcctg agaccgacaa agtgtggatc gagatcggtg aaaccgaggg  6720
aaccttcatc gtggacagcg tggagcttct cttgatggag gaataatgag atctatcgat  6780
tctagaaggc ctgaattctg catgcgtttg gacgtatgcc cattcaggtt ggagccaatt  6840
tggttgatgt gtgtgcgagt tcttgcgagt ctgatgagac atctctgtat tgtgtttctt  6900
tccccagtgt tttctgtact tgtgtaatcg gctaatcgcc aacagattcg gcgatgaata  6960
aatgagaaat aaattgttct gattttgagt gcaaaaaaaa aggaattaga tctgtgtgtg  7020
ttttttggat ccccgggggcg gccgcttcaa caagcttagg ctcaggattt agcagcattc  7080
cagattgggat tcaatcaaca aggtacgagc catatcactt tattcaaatt ggtatcgcca  7140
aaaccaagaa ggaactccca tcctcaaagg tttgtaagga agaattctca gtccaaagcc  7200
tcaacaaggt cagggtacag agtctccaaa ccattagcca aaagctacag agatcaatg   7260
aagaatcttc aatcaaagta aactactgtt ccagcacatg catcatggtc agtaagtttc  7320
agaaaaagac atccaccgaa gacttaaagt tagtgggcat cttttgaaagt aatcttgtca  7380
acatcgagca gctggcttgt ggggaccaga caaaaaagga atggtgcaga attgttaggc  7440
gcacctacca aaagcatctt tgcctttatt gcaaagataa agcagattcc tctagtacaa  7500
gtggggaaca aaataacgtg gaaaagagct gtcctgacag cccactcact aatgcgtatg  7560
acgaacgcag tgacgaccac aaaagaattc cctctatata agaaggcatt cattcccatt  7620
tgaaggatca tcagatactc aaccaatcct tctaggatct accgtcttcg gtacgcgctc  7680
actccgcccct ctgcctttgt tactgccacg tttctctgaa tgctctcttg tgtggtgatt  7740
gctgagagtg gtttagctgg atctagaatt acactctgaa atcgtgttct gcctgtgctg  7800
attacttgcc gtcctttgta gcagcaaaat atagggacat ggtagtacga aacgaagata  7860
gaacctacac agcaatacga gaaatgtgta atttggtgct tagcggtatt tatttaagca  7920
catgttggtg ttatagggca cttggattca gaagtttgct gttaattag gcacaggctt  7980
catactacat gggtcaatag tatagggatt catattatag gcgatactat aataatttgt  8040
tcgtctgcag agcttattat ttgccaaaat tagatattcc tattctgttt ttgtttgtat  8100
gctgttaaat tgttaacgcc tgaaggaata aatataaatg acgaaattt gatgtttatc  8160
tctgctcctt tattgtgacc ataagtcaag atcagatgca cttgttaa atattgttgt    8220
ctgaagaaat aagtactgac agtatttga tgcattgatc tgcttgtttg ttgtaacaaa   8280
atttaaaaat aaagagtttc ctttttgttg ctctccttac ctcctgatgg tatctagtat  8340
ctaccaactg acactatatt gcttctcttt acatacgtat cttgctcgat gccttctccc  8400
tagtgttgac cagtgttact cacatagtct ttgctcattt cattgtaatg cagataccaa  8460
gcggcctcta gaggatcagc atggcgccca ccgtgatgat ggcctcgtcg ccaccgccg   8520
tcgctccgtt ccaggggctc aagtccaccg ccagcctccc gctcgccgc cgctcctcca   8580
gaagcctcgg caacgtcagc aacgcggaa ggatccggtg catgcaggta acaaatgcat    8640
cctagctagt agttctttgc attgcagcag ctgcagctag cgagttagta ataggaaggg  8700
aactgatgat ccatgcatgg actgatgtgt gttgcccatc ccatcccatt tccaacccc   8760
aaacgaacca aaacacacgt actacgtgca ggtgtggccg gcctacggca acaagaagtt  8820
cgagacgctg tcgtacctgc cgccgctgtc gaccggcggg cgcatccgct gcatgcaggc  8880
catggacaac tccgtcctga actcggtcg caccaccatc tgcgacgcct acaacgtcgc  8940
ggcgcatgat ccattcagct tccagcacaa gagcctcgac actgttcaga aggagtggac  9000
ggagtggaag aagaacaacc acagcctgta cctggaacgc atgtcggca cggtggccag   9060
cttccttctc aagaaggtcg gctctctcgt cgggaagcgc atcctctcgg aactccgcaa  9120
cctgatcttt ccatctggct ccaccaacct catgcaagac atcctcaggg agaccgagaa  9180
gtttctcaac cagcgcctca acactgatac ccttgctcgc gtcaacgctg agctgacggg  9240
tctgcaagca aacgtggagg agttcaaccg ccaagtggac aacttcctca accccaaccg  9300
caatgcggtg cctctcgtcca tcacttcttc cgtgaacacc atgcaacaac tgttcctcaa  9360
ccgcttgcct cagttccaga tgcaaggcta ccagctgctc ctgctgccac tctttgctca  9420
ggctgccaac ctgcacctct ccttcattcg tgacgtgatc ctcaacgctg acgagtgggg  9480
catctctgca gccacgctga ggacctaccg cgactacctg aagaactaca ccaggggacta  9540
ctccaactat tgcatcaaca cctaccagtc ggccttcaac cggactccaata cgagcttca   9600
cgacatgctg gagttcagga cctacatgtt cctgaacgtg ttcgagtacg tcagcatctg  9660
gtcgctcttc aagtaccaga gcctgctggt gtccagcggc gccaacctct acgccagcgg  9720
ctctggtccc caacaaactc agagcttcac cagccaggac tggccattcc tgtattcgtt  9780
gttccaagtc aactccaact acgtcctcaa cggcttctct ggtgctcgcc tctccaacac  9840
cttccccaac attgttggcc tcccccggctc caccacaact catgctctgc ttgctgccag  9900
agtgaactac tccggcggca tctcgagcgg cgacattggt gcatcgccgt tcaaccagaa  9960
cttcaactgc tccaccttcc tgccgccgct gctcacccg ttcgtgaggt cctggctcga  10020
cagcggctcc gaccgcgagg gcgtggccac cgtcaccaac tggcaaaccg agtccttcga  10080
gaccacccgt ggcctccgga gcggcgcctt cacgcgcgt ggaaattcta actacttccc   10140
cgactacttc atcaggaaca tctctggtgt tcctctcgtc gtccgcaacg aggacctccg  10200
ccgtccactg cactacaacg agatcaggaa catcgcctct ccgtccggga cgccccggagg  10260
tgcaagggcg tacatggtga gcgtcctaa caggaagaac aacatccacg ctgtgcatga   10320
gaacggctcc atgatccacc tggcgcccaa tgattacaacc ggcttcacca tctctccaat  10380
ccacgccacc caagtgaaca accagacacg caccttcatc tccgagaagt tcggcaacca  10440
gggcgactcc ctgaggttcg agcagaacaa caccaccgcc aggtacacc tgcgcggcaa    10500
```

-continued

```
cggcaacagc tacaacctgt acctgcgcgt cagctccatt ggcaactcca ccatcagggt    10560
caccatcaac gggagggtgt acacagccac caatgtgaac acgacgacca acaatgatgg    10620
cgtcaacgac aacggcgccc gcttcagcga catcaacatt ggcaacgtgg tggccagcag    10680
caactccgac gtcccgctgg acatcaacgt gaccctgaac tctggcaccc agttcgacct    10740
catgaacatc atgctggtgc caactaacat ctcgccgctg tactgatagg agctctgatc    10800
cccatgggaa ttcccgatcg ttcaaacatt tggcaataaa gtttcttaag attgaatcct    10860
gttgccggtc ttgcgatgat tatcatataa tttctgttga attacgttaa gcatgtaata    10920
attaacatgt aatgcatgac gttatttatg agatgggttt ttatgattag agtcccgcaa    10980
ttatacattt aatacgcgat agaaaacaaa atatagcgcg caaactagga taaattatcg    11040
cgcgcggtgt catctatgtt actagatcgg ggatatcccc ggggcggccg cggggaattc    11100
ggtaccaagc tttggcgcgc caaatcgtga agtttctcat ctaagccccc atttggacgt    11160
gaatgtagac acgtcgaaat aaagatttcc gaattagaat aatttgttta ttgctttcgc    11220
ctataaatac gacggatcgt aatttgtcgt tttatcaaaa tgtactttca tttttataata   11280
acgctgcgga catctacatt tttgaattga aaaaaaattg gtaattactc tttctttttc    11340
tccatattga ccatcatact cattgcatcc ccggaaatta tgttttttta aaaaccacgg    11400
tattatagat accgtgttat tttttgagta ttggaaattt catttcaacc caaagtttct    11460
tcatggcaca tctagctttt gcctaatacc atgtagggct acatcttaaa aatctatact    11520
actatattaa agctgcaggg gtagcctgtc tccacctggt tctgcctcga gccaatctaa    11580
accgtccatc tatatccatc aaatcagcac cgtccggtcc gtgcgcacct cctctcccgc    11640
tattcagttg catacttgca gcaggttctc cctcctcacc atttcctctg cctcctctct    11700
cgctcactgg tcagattcat cctgcctctc ccgcatgcgc tccctcccca tgcccgtct    11760
cgcactatcg ccacacctca ccgcggggag acgaagacgg tggacgcatc ctcacctcct    11820
ccgctagttg tcgctcttcc atcctcttca acaacttcta catagggaga ggcggttcgg    11880
cgtcccgacg ccgccgcttc tcccctcccc atggaggacg agaacatcga cctcggcggc    11940
gggggcgatg cctccgctct gcatagagga gggttgtagt ggcaagcagc aatgccaaca    12000
ccgaggcggg ccaagactag gcaacaatag gacggcacgc ccggttgtca gcgaggtggc    12060
ggcatcgtgt gccgctaccg aacaacatct ccggcgctgg agtcggtgag ttactgcgcc    12120
acccggacgc cctcaatgca ctgatatcta cccggtctcc atcgccgcc ttcctccctt    12180
ccctctccct gtgcctccct ctcttgccct ctcccttcca actgctcccg ccccagccct    12240
agcccaacca cctcccgcgc agggtcacca a                                    12271
```